(12) United States Patent
Robaina et al.

(10) Patent No.: US 12,211,599 B2
(45) Date of Patent: Jan. 28, 2025

(54) MEDICAL ASSISTANT

(71) Applicant: Magic Leap, Inc., Plantation, FL (US)

(72) Inventors: Nastasja U. Robaina, Coconut Grove, FL (US); Nicole Elizabeth Samec, Ft. Lauderdale, FL (US); Mark Baerenrodt, Milbrae, CA (US); Christopher M. Harrises, Nashua, NH (US)

(73) Assignee: Magic Leap, Inc., Plantation, FL (US)

( * ) Notice: Subject to any disclaimer, the term of this patent is extended or adjusted under 35 U.S.C. 154(b) by 0 days.

(21) Appl. No.: 18/770,292

(22) Filed: Jul. 11, 2024

(65) Prior Publication Data

US 2024/0363209 A1 Oct. 31, 2024

Related U.S. Application Data

(63) Continuation of application No. 18/056,164, filed on Nov. 16, 2022, now Pat. No. 12,080,393, which is a
(Continued)

(51) Int. Cl.
*G16H 10/60* (2018.01)
*A61B 3/00* (2006.01)
(Continued)

(52) U.S. Cl.
CPC ........... *G16H 10/60* (2018.01); *A61B 3/0041* (2013.01); *A61B 3/10* (2013.01); *A61B 3/113* (2013.01); *A61B 5/0077* (2013.01); *A61B 5/06* (2013.01); *A61B 5/1171* (2016.02); *A61B 5/1176* (2013.01); *A61B 5/339* (2021.01); *A61B 90/37* (2016.02); *G02B 27/0093* (2013.01); *G06F 16/22* (2019.01); *G06F 16/2379* (2019.01); *G06F 21/32* (2013.01); *G06F 40/205* (2020.01); *G06F 40/289* (2020.01); *G06V 20/20* (2022.01);
(Continued)

(58) Field of Classification Search
None
See application file for complete search history.

(56) References Cited

U.S. PATENT DOCUMENTS

| | | |
|---|---|---|
| 5,291,560 A | 3/1994 | Daugman |
| 7,395,215 B2 | 7/2008 | Grushka |

(Continued)

FOREIGN PATENT DOCUMENTS

| | | |
|---|---|---|
| JP | H11197159 A | 7/1999 |
| JP | 2002140685 A | 5/2002 |

(Continued)

OTHER PUBLICATIONS

KR10-2019-7022814 Notice of Allowance dated Feb. 6, 2024.
(Continued)

*Primary Examiner* — Anne-Marie K Alderson
(74) *Attorney, Agent, or Firm* — Tobias Intellectual Property Law, PLLC

(57) ABSTRACT

A wearable device can present virtual content to the wearer for many applications in a healthcare setting. The wearer may be a patient or a healthcare provider (HCP). Such applications can include, but are not limited to, access, display, and modification of patient medical records and sharing patient medical records among authorized HCPs.

20 Claims, 33 Drawing Sheets

Related U.S. Application Data continuation of application No. 15/865,023, filed on Jan. 8, 2018, now abandoned.

(60) Provisional application No. 62/448,656, filed on Jan. 20, 2017, provisional application No. 62/445,182, filed on Jan. 11, 2017.

(51) Int. Cl.

| | |
|---|---|
| *A61B 3/10* | (2006.01) |
| *A61B 3/113* | (2006.01) |
| *A61B 5/00* | (2006.01) |
| *A61B 5/06* | (2006.01) |
| *A61B 5/1171* | (2016.01) |
| *A61B 5/339* | (2021.01) |
| *A61B 90/00* | (2016.01) |
| *G02B 27/00* | (2006.01) |
| *G06F 16/22* | (2019.01) |
| *G06F 16/23* | (2019.01) |
| *G06F 21/32* | (2013.01) |
| *G06F 40/205* | (2020.01) |
| *G06F 40/289* | (2020.01) |
| *G06V 20/20* | (2022.01) |
| *G10L 15/26* | (2006.01) |
| *G16H 30/40* | (2018.01) |
| *G16H 40/67* | (2018.01) |
| *A61B 17/00* | (2006.01) |
| *A61B 34/20* | (2016.01) |
| *A61B 90/50* | (2016.01) |
| *G02B 27/01* | (2006.01) |
| *G06F 21/62* | (2013.01) |

(52) U.S. Cl.
CPC ............ *G10L 15/26* (2013.01); *G16H 40/67* (2018.01); *A61B 2017/00207* (2013.01); *A61B 2017/00216* (2013.01); *A61B 2034/2048* (2016.02); *A61B 2090/365* (2016.02); *A61B 2090/372* (2016.02); *A61B 2090/502* (2016.02); *G02B 2027/0127* (2013.01); *G02B 2027/0138* (2013.01); *G02B 2027/014* (2013.01); *G02B 2027/0141* (2013.01); *G06F 21/6245* (2013.01); *G06V 2201/034* (2022.01); *G16H 30/40* (2018.01)

(56) References Cited

U.S. PATENT DOCUMENTS

| | | | |
|---|---|---|---|
| 8,950,867 B2 | 2/2015 | Macnamara | |
| 9,215,293 B2 | 12/2015 | Miller | |
| 9,275,079 B2 | 3/2016 | Nalawadi et al. | |
| 9,305,551 B1 | 4/2016 | Johns et al. | |
| 9,310,559 B2 | 4/2016 | Macnamara | |
| 9,348,143 B2 | 5/2016 | Gao et al. | |
| D758,367 S | 6/2016 | Natsume | |
| 9,417,452 B2 | 8/2016 | Schowengerdt et al. | |
| 9,470,906 B2 | 10/2016 | Kaji et al. | |
| 9,538,962 B1* | 1/2017 | Hannaford | G16H 40/63 |
| 9,547,174 B2 | 1/2017 | Gao et al. | |
| 9,671,566 B2 | 6/2017 | Abovitz et al. | |
| 9,740,006 B2 | 8/2017 | Gao | |
| 9,791,700 B2 | 10/2017 | Schowengerdt | |
| 9,851,563 B2 | 12/2017 | Gao et al. | |
| 9,857,591 B2 | 1/2018 | Welch et al. | |
| 9,874,749 B2 | 1/2018 | Bradski et al. | |
| 10,013,808 B2 | 7/2018 | Jones et al. | |
| 2006/0028436 A1 | 2/2006 | Armstrong | |
| 2006/0109237 A1 | 5/2006 | Morita et al. | |
| 2007/0081123 A1 | 4/2007 | Lewis | |
| 2007/0173265 A1 | 7/2007 | Gum | |
| 2007/0238981 A1 | 10/2007 | Zhu et al. | |
| 2007/0282195 A1* | 12/2007 | Masini | A61B 34/74 600/407 |
| 2009/0054084 A1 | 2/2009 | Buhrke et al. | |
| 2009/0103785 A1 | 4/2009 | Pedroza | |
| 2009/0160854 A1 | 6/2009 | Stoval, III et al. | |
| 2009/0299924 A1 | 12/2009 | Bauer et al. | |
| 2010/0049664 A1 | 2/2010 | Kuo | |
| 2010/0286490 A1 | 11/2010 | Koverzin | |
| 2011/0029320 A1 | 2/2011 | Jamali et al. | |
| 2012/0038637 A1 | 2/2012 | Marks | |
| 2012/0127062 A1 | 5/2012 | Bar-Zeev et al. | |
| 2012/0162549 A1 | 6/2012 | Gao et al. | |
| 2013/0036134 A1* | 2/2013 | Neven | G06V 40/172 707/769 |
| 2013/0082922 A1 | 4/2013 | Miller | |
| 2013/0117377 A1 | 5/2013 | Miller | |
| 2013/0125027 A1 | 5/2013 | Abovitz | |
| 2013/0174213 A1 | 7/2013 | Liu et al. | |
| 2013/0208014 A1 | 8/2013 | Fleck et al. | |
| 2013/0208234 A1 | 8/2013 | Lewis | |
| 2013/0242262 A1 | 9/2013 | Lewis | |
| 2014/0003762 A1 | 1/2014 | Macnamara | |
| 2014/0071539 A1 | 3/2014 | Gao | |
| 2014/0081659 A1 | 3/2014 | Nawana et al. | |
| 2014/0177023 A1 | 6/2014 | Gao et al. | |
| 2014/0218468 A1 | 8/2014 | Gao et al. | |
| 2014/0222462 A1 | 8/2014 | Shakil et al. | |
| 2014/0267420 A1 | 9/2014 | Schowengerdt et al. | |
| 2014/0306866 A1 | 10/2014 | Miller et al. | |
| 2015/0016777 A1* | 1/2015 | Abovitz | G02B 27/0093 385/37 |
| 2015/0088546 A1* | 3/2015 | Balram | G16H 10/60 705/3 |
| 2015/0088547 A1 | 3/2015 | Balram et al. | |
| 2015/0099458 A1 | 4/2015 | Weisner et al. | |
| 2015/0103306 A1 | 4/2015 | Kaji et al. | |
| 2015/0120321 A1 | 4/2015 | David et al. | |
| 2015/0156028 A1 | 6/2015 | Ballard et al. | |
| 2015/0173846 A1 | 6/2015 | Schneider et al. | |
| 2015/0178939 A1 | 6/2015 | Bradski et al. | |
| 2015/0205126 A1 | 7/2015 | Schowengerdt | |
| 2015/0221105 A1 | 8/2015 | Tripathi et al. | |
| 2015/0222883 A1 | 8/2015 | Welch | |
| 2015/0222884 A1 | 8/2015 | Cheng | |
| 2015/0268415 A1 | 9/2015 | Schowengerdt et al. | |
| 2015/0294089 A1 | 10/2015 | Nichols | |
| 2015/0302652 A1 | 10/2015 | Miller et al. | |
| 2015/0309263 A2 | 10/2015 | Abovitz et al. | |
| 2015/0326570 A1 | 11/2015 | Publicover et al. | |
| 2015/0346490 A1 | 12/2015 | TeKolste et al. | |
| 2015/0346495 A1 | 12/2015 | Welch et al. | |
| 2016/0011419 A1 | 1/2016 | Gao | |
| 2016/0015470 A1 | 1/2016 | Border | |
| 2016/0026253 A1 | 1/2016 | Bradski et al. | |
| 2016/0116739 A1 | 4/2016 | TeKolste et al. | |
| 2016/0148052 A1 | 5/2016 | Tsuda et al. | |
| 2016/0191887 A1 | 6/2016 | Casas | |
| 2016/0249989 A1 | 9/2016 | Devam et al. | |
| 2016/0270656 A1 | 9/2016 | Samec et al. | |
| 2016/0287337 A1 | 10/2016 | Aram et al. | |
| 2016/0366084 A1 | 12/2016 | Malahy | |
| 2017/0021273 A1 | 1/2017 | Rios | |
| 2017/0056115 A1 | 3/2017 | Corndorf et al. | |
| 2017/0086926 A1 | 3/2017 | Amling | |
| 2017/0227581 A1 | 8/2017 | Knierim et al. | |
| 2017/0243157 A1 | 8/2017 | Piron et al. | |
| 2017/0323062 A1* | 11/2017 | Djajadiningrat | G06F 16/3326 |
| 2018/0032130 A1 | 2/2018 | Meglan | |
| 2018/0082476 A1 | 3/2018 | Kline et al. | |
| 2018/0197624 A1 | 7/2018 | Robaina et al. | |
| 2023/0075466 A1 | 3/2023 | Robaina et al. | |

FOREIGN PATENT DOCUMENTS

| | | |
|---|---|---|
| JP | H0966056 B | 11/2005 |
| JP | 2007094943 A | 4/2007 |
| JP | 2009529951 A | 8/2009 |
| JP | 2009279193 A | 12/2009 |

(56) References Cited

FOREIGN PATENT DOCUMENTS

| | | |
|---|---|---|
| JP | 2014071663 A | 4/2014 |
| JP | 2015019678 A | 2/2015 |
| JP | 2015062118 A | 4/2015 |
| JP | 2015118448 A | 6/2015 |
| KR | 20100000857 A | 1/2010 |
| KR | 20100014065 A | 2/2010 |
| KR | 20110042277 A | 4/2011 |
| KR | 20140112207 A | 9/2014 |
| KR | 20150090991 A | 8/2015 |
| WO | 2015081313 A2 | 6/2015 |
| WO | 2015116805 A1 | 8/2015 |
| WO | 2015161307 A1 | 10/2015 |
| WO | 2016023097 A1 | 2/2016 |
| WO | 2016078919 A1 | 5/2016 |
| WO | 2018067515 A1 | 4/2018 |

OTHER PUBLICATIONS

KR10-2019-7022814 Office Action dated Aug. 17, 2023.
KR10-2019-7022814 Office Action dated Feb. 13, 2023.
U.S. Appl. No. 12/080,393, filed Sep. 3, 2024, Robaina et al.
ARToolKit: https://web.archive.org/web/20051013062315/http://www.hitl.washington.edu:80/artoolkit/documentation/hardware.htm, archived Oct. 13, 2005.
Azuma, "A Survey of Augmented Reality," Teleoperators and Virtual Environments 6, 4 (Aug. 1997), pp. 355-385. https://web.archive.org/web/20010604100006/http://www.cs.unc.edu/ azuma/ARpresence.pdf.
Azuma, "Predictive Tracking for Augmented Realty," TR95-007, Department of Computer Science, UNC-Chapel Hill, NC, Feb. 1995.
Bimber, et al., "Spatial Augmented Reality—Merging Real and Virtual Worlds," 2005 https://web.media.mit.edu/raskar/book/BimberRaskarAugmentedRealityBook.pdf.
EP18738589.3 Examination Report dated Oct. 26, 2023.
Garrido-Jurado, S., et al.; Automatic generation and detection of highly reliable fiducial markers under occlusion; Pattern Recognition 47 (2014) 2280-2292 (Year: 2014).
IL267995 Office Action dated Oct. 25, 2023.
International Preliminary Report for PCT Application No. PCT/US2018/012816, issued Jul. 16, 2019.
International Search Report and Written Opinion in corresponding International Patent Application No. PCT/US2018/012816, dated Mar. 6, 2018, in 12 pages.
Jacob, "Eye Tracking in Advanced Interface Design," Human-Computer Interaction Lab Naval Research Laboratory, Washington, D.C. / paper/ in Virtual Environments and Advanced Interface Design, ed. by W. Barfield and T.A. Furness, pp. 258-288, Oxford University Press, New York (1995).
JP2022-179491 Office Action mailed Dec. 1, 2023.
Nishikawa, et al., "Mutual View Sharing System for Real-Time Tele-Communication," The Transactions of the Institute of Electronics, Information, and Communication Engineers, Feb. 1, 2005, J88-D-I No. 2, pp. 292-304.
Tanriverdi and Jacob, "Interacting With Eye Movements in Virtual Environments," Department of Electrical Engineering and Computer Science, Tufts University, Medford, MA—paper/Proc. AMC CHI 2000 Human Factors in Computing Systems Conference, pp. 265-272, Addison-Wesley/ACM Press (2000).
Shuhaiber JH, "Augmented Reality in Surgery." Arch. Surg. 2004; 139(2): 170-174. Feb. 2004.

\* cited by examiner

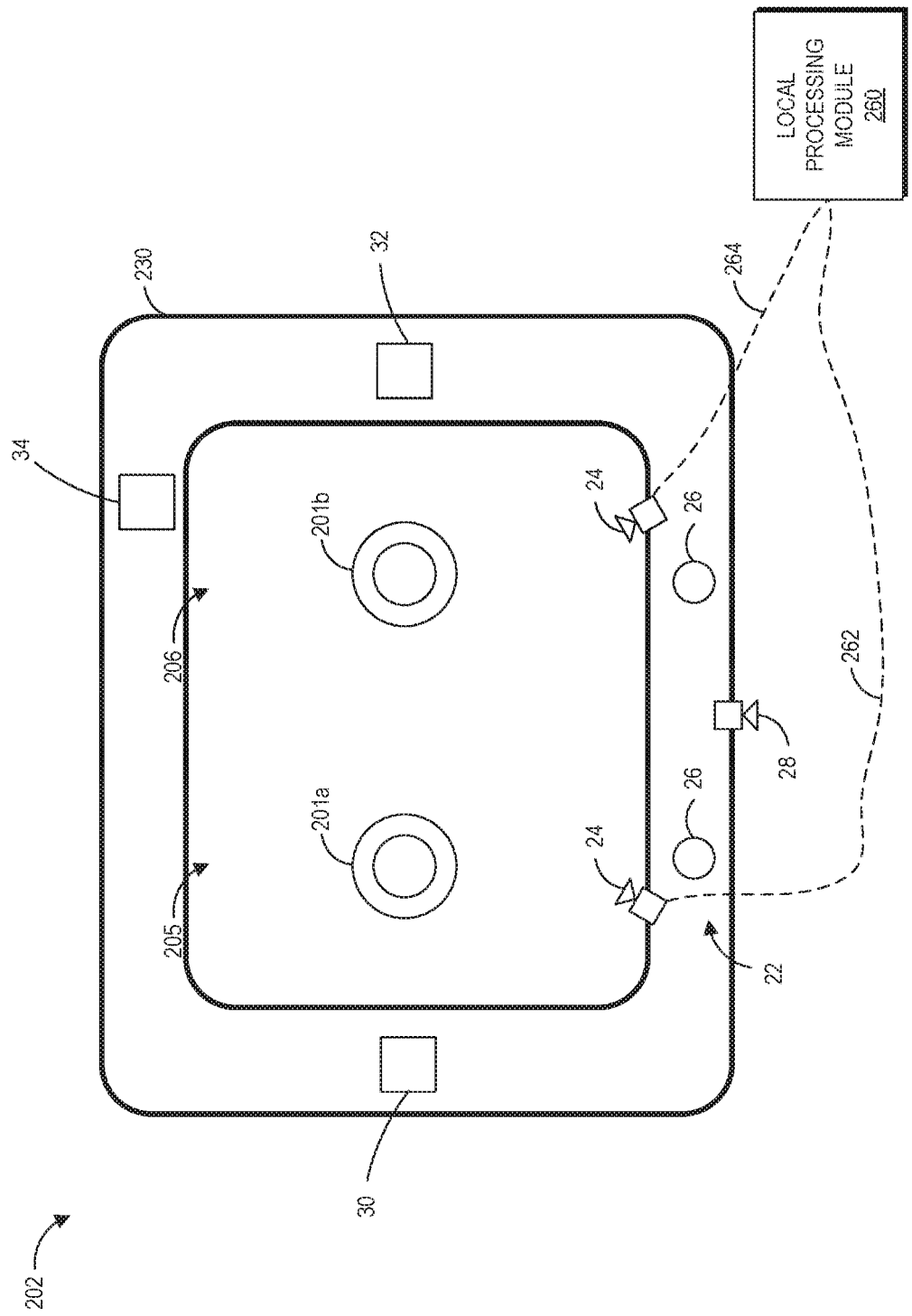

MEDICAL ASSISTANT

PRIORITY CLAIM

This application is a continuation of U.S. patent application Ser. No. 18/056,164 filed on Nov. 16, 2022, titled "MEDICAL ASSISTANT,", which is a continuation of U.S. patent application Ser. No. 15/865,023 filed on Jan. 8, 2018, titled "MEDICAL ASSISTANT," which claims the benefit of priority under 35 U.S.C. § 119 (e) to U.S. Provisional Application No. 62/445,182, filed on Jan. 11, 2017, titled "MEDICAL ASSISTANT," and to U.S. Provisional Application No. 62/448,656, filed on Jan. 20, 2017, titled "MEDICAL ASSISTANT." The entire disclosure of each of the above-listed applications is hereby incorporated by reference into this application.

FIELD

The present disclosure relates to virtual reality and augmented reality imaging and visualization systems in a healthcare setting.

BACKGROUND

Modern computing and display technologies have facilitated the development of systems for so called "virtual reality" "augmented reality" or "mixed reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user; an mixed reality, or "MR", related to merging real and virtual worlds to produce new environments where physical and virtual objects co-exist and interact in real time. As it turns out, the human visual perception system is very complex, and producing a VR, AR, or MR technology that facilitates a comfortable, natural-feeling, rich presentation of virtual image elements amongst other virtual or real-world imagery elements is challenging. Systems and methods disclosed herein address various challenges related to VR, AR and MR technology.

SUMMARY

A wearable device can present virtual content to a wearer for many applications in a healthcare setting. The wearer may be a patient or a healthcare provider (HCP). Such applications can include, but are not limited to, access, display, and modification of patient medical records and sharing patient medical records among authorized HCPs. The patient medical records can be stored in the centralized location and owned by the patient, rather than by various HCP organizations (e.g., hospitals, clinics, doctors' offices) whose services the patient may use. The wearable device can access and display portions of the patient's medical record to authorized HCPs. Because the patient's medical record is centrally stored and modified whenever the patient has a procedure or treatment, the medical record can remain substantially complete. During a medical procedure or treatment, the wearable device can display to an attending HCP virtual content associated with the patient or the patient's medical record. The HCP can use the wearable device to update the patient's medical record to account for the results of a procedure or treatment. The HCP can use the wearable device to share some or all of the patient's medical record with other authorized HCPs. An outward-facing camera of the wearable device can image and track medical instruments used during a medical procedure. The wearable device can image portions of the patient during a procedure. If a medical instrument were to be left inside the patient's body, or the HCP were to depart from the authorized medical procedure or protocol, the wearable device can display an alert to the HCP so that the instrument can be removed from the patient's body or to follow the authorized procedure or protocol.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIG. 2B shows a schematic view of an example of various components of a wearable system comprising environmental sensors.

Figure 1A:
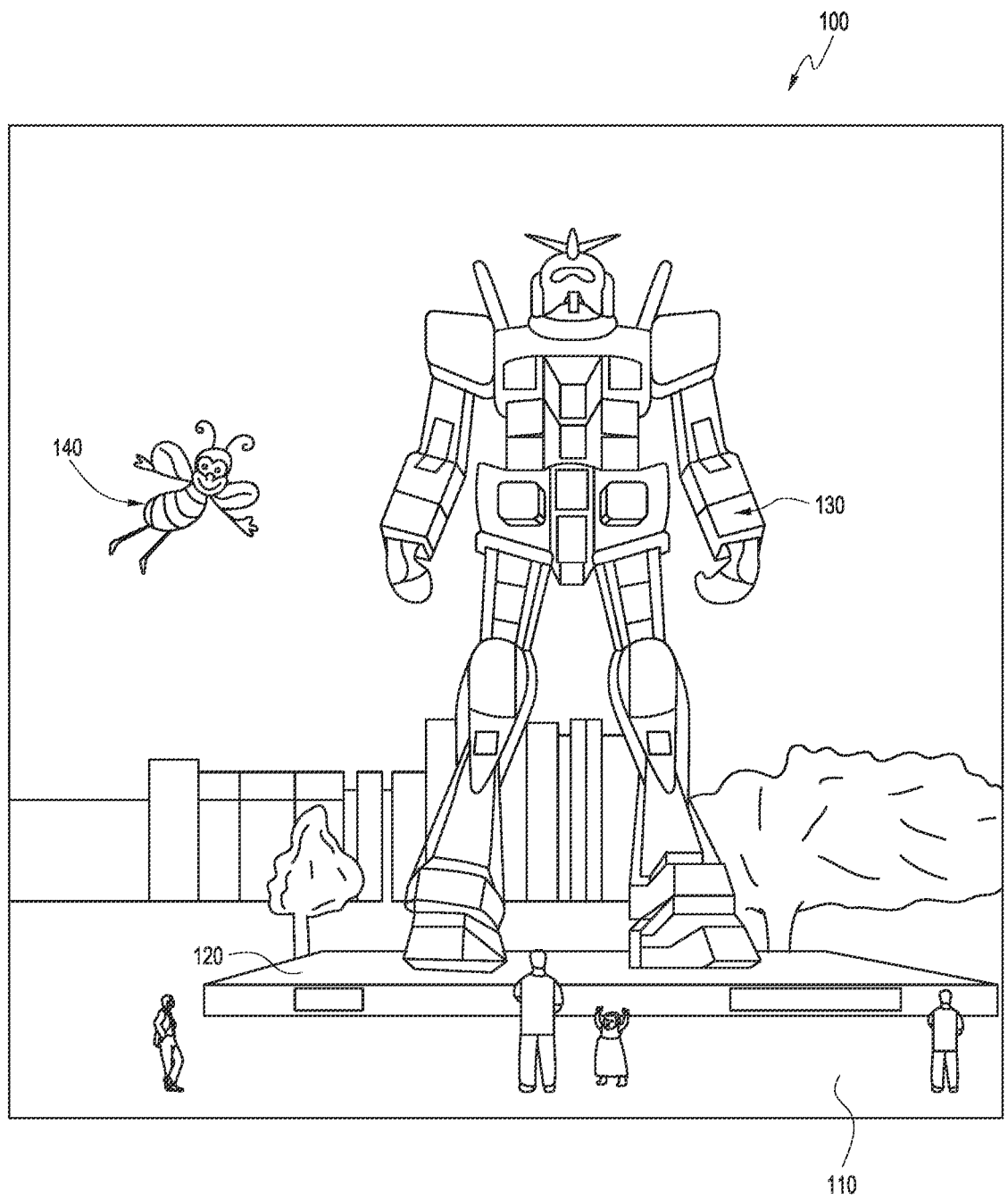
FIG. 1A depicts an illustration of a mixed reality scenario with certain virtual reality objects, and certain physical objects viewed by a person.

Throughout the drawings, reference numbers may be re-used to indicate correspondence between referenced elements. The drawings are provided to illustrate example embodiments described herein and are not intended to limit the scope of the disclosure.

DETAILED DESCRIPTION

Overview

Wearable devices that can present virtual content to the wearer can have a number of applications in a healthcare setting. Such applications can include, but are not limited to, accessing, displaying, and modifying of patient medical records and sharing patient medical records among authorized healthcare providers (HCPs). The patient medical records can be stored in the centralized location and owned by the patient, rather than by various HCP organizations (e.g., hospitals, clinics, doctor's offices) whose services the patient may use. The wearable device can access and display to authorized personnel portions of the patient's medical record. Because the patient's medical record is centrally stored and modified whenever the patient has a procedure or treatment, the medical record can remain substantially complete (as compared to the currently common piecemeal scenario where each HCP organization that treats the patient stores and modifies its own medical record associated with the patient). Additionally, because the patient's medical record is stored and updated substantially in real-time whenever the patient has a procedure or treatment, the medical record can remain substantially unbiased, accurate, and objective (as compared to the currently common scenario where each HCP stores and updates the patient's record sometime after he treats the patient and he may include subjective information in the medical record due to inaccurate memories.)

During a medical procedure or treatment, the wearable device can display to an attending HCP virtual content associated with the patient or the patient's medical record. The HCP can use the wearable device to update the patient's medical record to account for the results of the procedure or treatment. The HCP can use the wearable device to share some or all of the patient's medical record with other authorized HCPs (e.g., a surgeon can share the medical record with the pathologist during an operation on the patient). A danger to a patient during a medical operation is the possibility of a surgeon leaving a foreign object (e.g., a medical instrument such as, e.g., a scalpel) inside the patient's body. An outward-facing camera of the wearable device can image medical instruments used during the operation, and the wearable device can track the location of the medical instruments. If a foreign object were to be left inside the patient's body, the wearable system can display an alert to the surgeon so that the foreign object can be removed from the patient's body before the operation is completed.

These and other advantageous applications of wearable systems in healthcare settings will be described below.

Examples of a 3D Display

A wearable system (also referred to herein as an augmented reality (AR) system) can be configured to present 2D or 3D virtual images to a user. The images may be still images, frames of a video, or a video, in combination or the like. At least a portion of the wearable system can be implemented on a wearable device that can present a VR, AR, or MR environment, alone or in combination, for user interaction. The wearable device can be used interchangeably as an AR device (ARD). Further, for the purpose of the present disclosure, the term "AR" is used interchangeably with the term "MR".

FIG. 1A depicts an illustration of a mixed reality scenario with certain virtual reality objects, and certain physical objects viewed by a person. In FIG. 1A, an MR scene 100 is depicted wherein a user of an MR technology sees a real-world park-like setting 110 featuring people, trees, buildings in the background, and a concrete platform 120. In addition to these items, the user of the MR technology also perceives that he "sees" a robot statue 130 standing upon the real-world platform 120, and a cartoon-like avatar character 140 flying by which seems to be a personification of a bumble bee, even though these elements do not exist in the real world.

In order for the 3D display to produce a true sensation of depth, and more specifically, a simulated sensation of surface depth, it is desirable for each point in the display's visual field to generate the accommodative response corresponding to its virtual depth. If the accommodative response to a display point does not correspond to the virtual depth of that point, as determined by the binocular depth cues of convergence and stereopsis, the human eye may experience an accommodation conflict, resulting in unstable imaging, harmful eye strain, headaches, and, in the absence of accommodation information, almost a complete lack of surface depth.

Figure 1B:
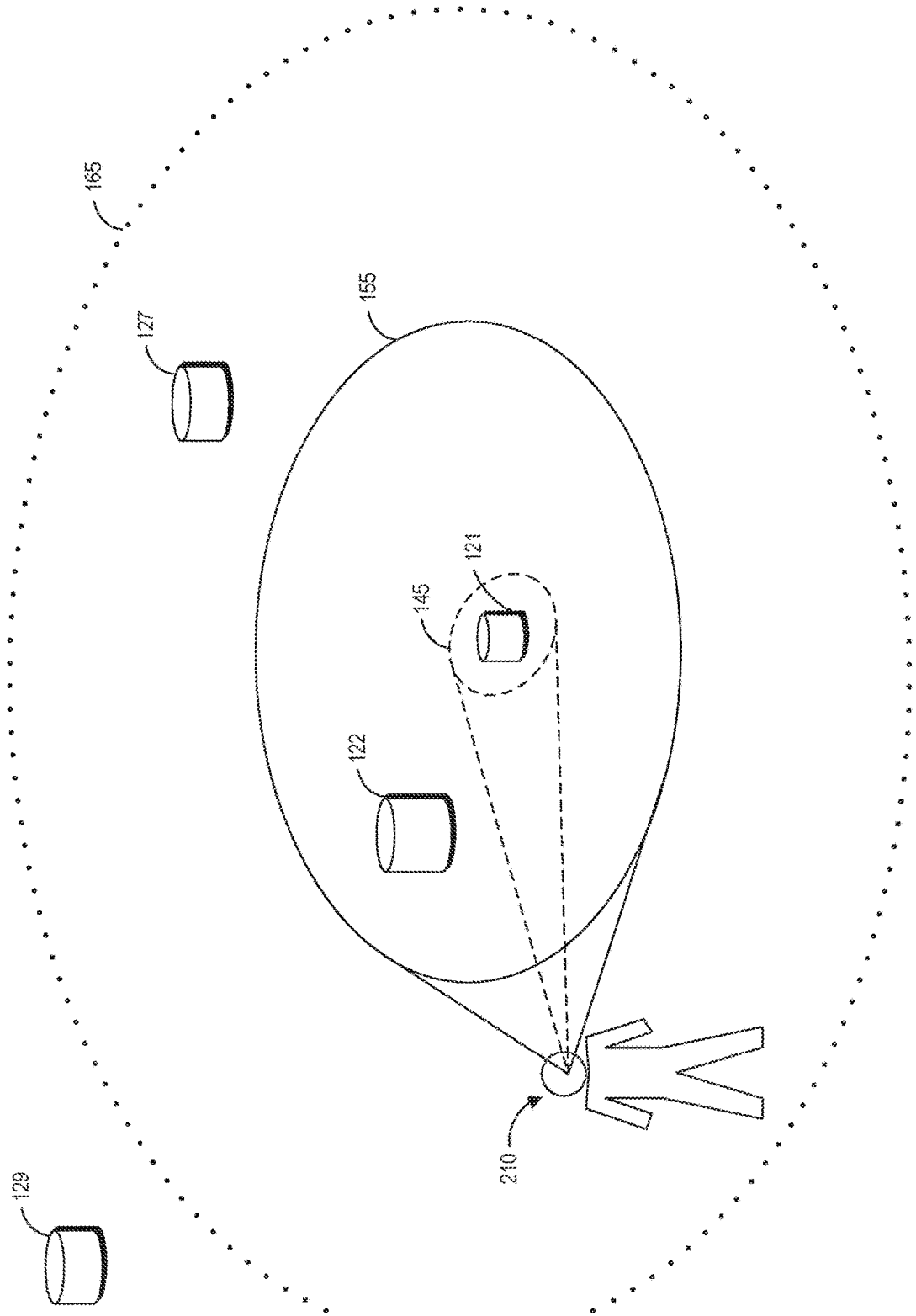
FIG. 1B illustrates a field of view and a field of regard for a wearer of a wearable system.

FIG. 1B illustrates a person's field of view (FOV) and field of regard (FOR). The FOV comprises a portion of an environment of the user that is perceived at a given time by the user. This field of view can change as the person moves about, moves their head, or moves their eyes or gaze.

The FOR comprises a portion of the environment around the user that is capable of being perceived by the user via the wearable system. Accordingly, for a user wearing a head-mounted augmented reality device, the field of regard may include substantially all of the $4\pi$ steradian solid angle surrounding the wearer, because the wearer can move his or her body, head, or eyes to perceive substantially any direction in space. In other contexts, the user's movements may be more constricted, and accordingly the user's field of regard may subtend a smaller solid angle. FIG. 1B shows such a field of view 155 including central and peripheral regions. The central field of view will provide a person a corresponding view of objects in a central region of the environmental view. Similarly, the peripheral field of view will provide a person a corresponding view of objects in a peripheral region of the environmental view. In this case, what is considered central and what is considered peripheral is a function of which direction the person is looking, and hence their field of view. The field of view 155 may include objects 121, 122. In this example, the central field of view 145 includes the object 121, while the other object 122 is in the peripheral field of view.

The field of view (FOV) 155 can contain multiple objects (e.g., objects 121, 122). The field of view 155 can depend on the size or optical characteristics of the AR system, for example, clear aperture size of the transparent window or lens of the head mounted display through which light passes from the real world in front of the user to the user's eyes. In some embodiments, as the user's 210 pose changes (e.g., head pose, body pose, and/or eye pose), the field of view 155 can correspondingly change, and the objects within the field of view 155 may also change. As described herein, the wearable system may include sensors such as cameras that monitor or image objects in the field of regard 165 as well as objects in the field of view 155. In some such embodiments, the wearable system may alert the user of unnoticed objects or events occurring in the user's field of view 155 and/or occurring outside the user's field of view but within the field of regard 165. In some embodiments, the AR system can also distinguish between what a user 210 is or is not directing attention to.

The objects in the FOV or the FOR may be virtual or physical objects. The virtual objects may include, for example, operating system objects such as e.g., a terminal for inputting commands, a file manager for accessing files or directories, an icon, a menu, an application for audio or video streaming, a notification from an operating system, and so on. The virtual objects may also include objects in an application such as e.g., avatars, virtual objects in games, or graphics or images, etc. The virtual objects may also include a patient's data (such as physiological data or medical history), as well as the environmental data such as the temperature of an operating room, etc. Some virtual objects can be both an operating system object and an object in an application. The wearable system can add virtual elements to the existing physical objects viewed through the transparent optics of the head mounted display, thereby permitting user interaction with the physical objects. For example, the wearable system may add a virtual menu associated with a medical monitor in the room, where the virtual menu may give the user the option to turn on or adjust medical imaging equipment or dosing controls using the wearable device. Accordingly, the wearable system may present additional virtual image content to the wearer in addition to the object in the environment of the user.

FIG. 1B also shows the field of regard (FOR) 165, which comprises a portion of the environment around a person 210 that is capable of being perceived by the person 210, for example, by turning their head or redirecting their gaze. The center portion of the field of view 155 of a person's 210 eyes may be referred to as the central field of view 145. The region within the field of view 155 but outside the central field of view 145 may be referred to as the peripheral field of view. In FIG. 1B, the field of regard 165 can contain a group of objects (e.g., objects 121, 122, 127) which can be perceived by the user wearing the wearable system.

In some embodiments, objects 129 may be outside the user's visual FOR but may nonetheless potentially be perceived by a sensor (e.g., a camera) on a wearable device (depending on their location and field of view) and information associated with the object 129 displayed for the user 210 or otherwise used by the wearable device. For example, the objects 129 may be behind a wall in a user's environment so that the objects 129 are not visually perceivable by the user. However, the wearable device may include sensors (such as radio frequency, Bluetooth, wireless, or other types of sensors) that can communicate with the objects 129.
Examples of a Wearable System VR, AR, and MR experiences can be provided by display systems having displays in which images corresponding to a plurality of depth planes are provided to a viewer. The images may be different for each depth plane (e.g., provide slightly different presentations of a scene or object) and may be separately focused by the viewer's eyes, thereby helping to provide the user with depth cues based on the accommodation of the eye required to bring into focus different image features for the scene located on different depth planes and/or based on observing different image features on different depth planes being out of focus. As discussed elsewhere herein, such depth cues provide credible perceptions of depth.

Figure 2A:
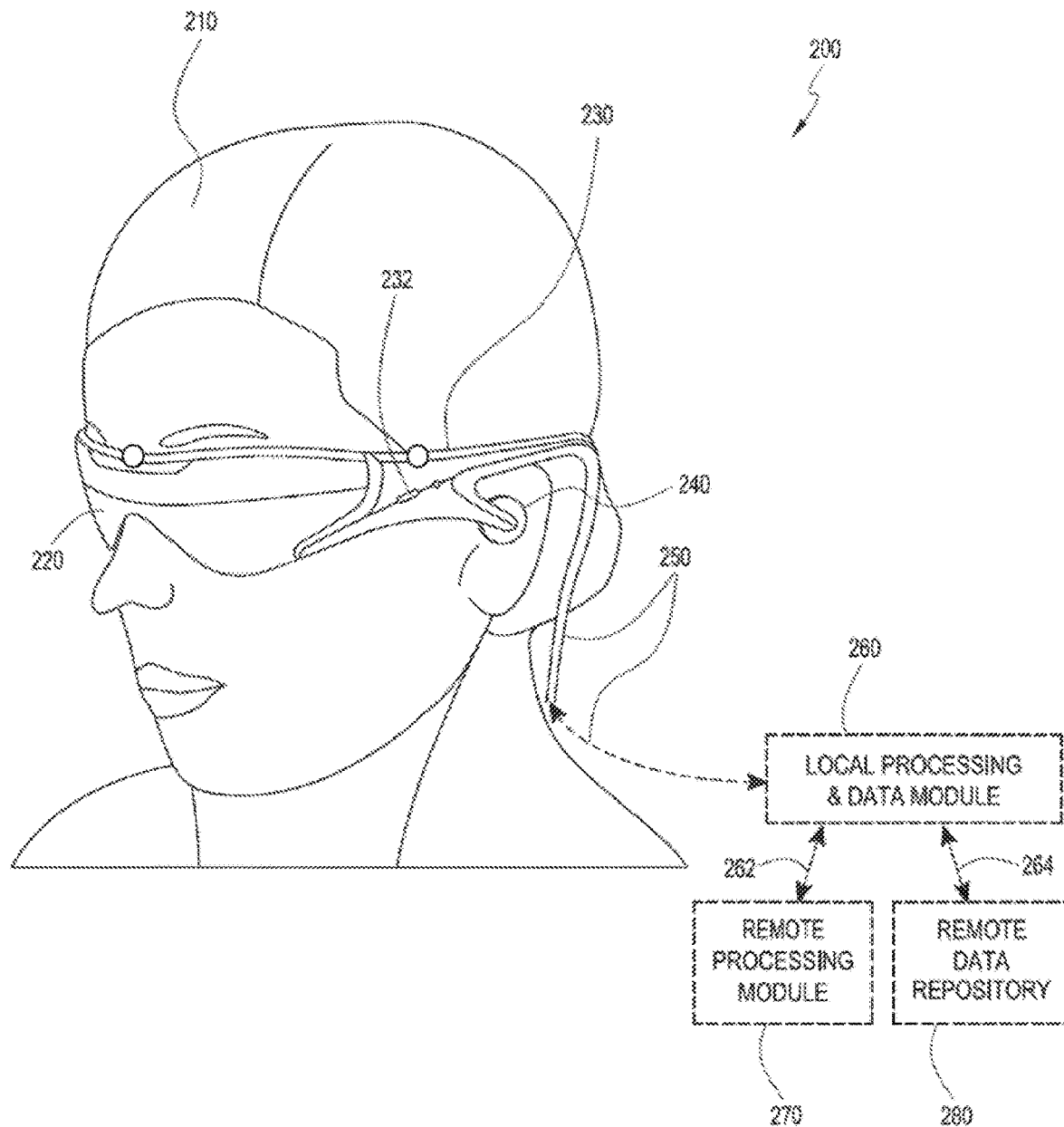
FIG. 2A schematically illustrates an example of a wearable system.

FIG. 2A illustrates an example of wearable system 200 which can be configured to provide an AR/VR/MR scene. The wearable system 200 may be part of a wearable device (such as for that can present a VR, AR, or MR environment, alone or in combination, for user interaction. The wearable system 200 can include a display 220, and various mechanical and electronic modules and systems to support the functioning of display 220. The display 220 may be coupled to a frame 230, which is wearable by a user, wearer, or viewer 210. The display 220 can be positioned in front of the eyes of the user 210. The display 220 can present AR/VR/MR content to a user. The display 220 can comprise a head mounted display (HMD) that is worn on the head of the user. In FIG. 2A, a speaker 240 is coupled to the frame 230 and positioned adjacent the ear canal of the user (in some embodiments, another speaker, not shown, is positioned adjacent the other ear canal of the user to provide for stereo/shapeable sound control).

As further described with reference to FIGS. 12-26, the wearable system 200 can be configured to allow a user to interact with virtual and physical objects. As an example, a doctor can wear an ARD which can present virtual content such as a virtual representation of a patient's medical record or physiological data (e.g., an electrocardiogram) to the doctor while the doctor is examining or performing a procedure or operation on the patient. The virtual content may be presented based on the user's interaction with physical objects in the doctor's environment. For example, while a doctor is performing a surgery on a patient, the wearable system can display virtual information related to surgical equipment used by the doctor, for example, to track the location or status of surgical instruments used by the doctor (or surgical team).

The wearable system 200 can also include an outward-facing imaging system 464 (shown in FIG. 4) which observes the world in the environment around the user. The wearable system 200 can also include an inward-facing imaging system 462 (shown in FIG. 4) which can track the eye movements of the user. The inward-facing imaging system may track either one eye's movements or both eyes' movements. The inward-facing imaging system may be attached to the frame 230 and may be in electrical communication with the processing modules 260 and/or 270, which may process image information acquired by the inward-facing imaging system to determine, e.g., the pupil diameters and/or orientations of the eyes or eye pose of the user 210.

As an example, the wearable system 200 can use the outward-facing imaging system 464 and/or the inward-facing imaging system 462 to acquire images of a pose of the user. The images may be still images, animation, frames of a video, or a video, in combination or the like. The pose of the user may include head pose, eye pose, hand gestures, foot pose, or other body poses. One or more poses may be used to activate or to turn off voice recordings of a patient's visit. For example, the doctor may use a certain hand gesture to indicate whether to start dictating the diagnosis of the patient.

The wearable system 200 can also include an audio sensor (e.g., a microphone 232). The microphone 232 may be an environmental sensor as further described with reference to FIG. 2B. The microphone may be (fixedly or removably) attached to the frame 230, display 220 (or other components of the wearable system 200), removably attached to the user 210, fixedly or removably to a physical object (such as a medical equipment) or another person (such as, e.g., a patient of the user). The microphone 232 may be used to receive audio data of a user of the wearable system 200 or sounds in the user's environment (such as when a patient of the user is talking). The audio data received by the microphone 232 may be used to activate or turn off the dictation features described herein. For example, the wearable system 200 can detect a keyword which can trigger the wearable system 200 to record the audio received by the microphone 232. In some embodiments, one or more other audio sensors, not shown, are positioned to provide stereo sound reception. Stereo sound reception can be used to determine the location of a sound source. The wearable system 200 can perform voice or speech recognition on the audio stream.

The display 220 can be operatively coupled 250, such as by a wired lead or wireless connectivity, to a local data processing module 260 which may be mounted in a variety of configurations, such as fixedly attached to the frame 230, fixedly attached to a helmet or hat worn by the user, embedded in headphones, or otherwise removably attached to the user 210 (e.g., in a backpack-style configuration, in a belt-coupling style configuration).

The local processing and data module 260 may comprise a hardware processor, as well as digital memory, such as non-volatile memory (e.g., flash memory), both of which may be utilized to assist in the processing, caching, and storage of data. The data may include data a) captured from environmental sensors (which may be, e.g., operatively coupled to the frame 230 or otherwise attached to the user 210); and/or b) acquired and/or processed using remote processing module 270 and/or remote data repository 280, possibly for passage to the display 220 after such processing or retrieval. The local processing and data module 260 may be operatively coupled by communication links 262 and/or 264, such as via wired or wireless communication links, to the remote processing module 270 and/or remote data repository 280 such that these remote modules are available as resources to the local processing and data module 260. In addition, remote processing module 280 and remote data repository 280 may be operatively coupled to each other.

In some embodiments, the remote processing module 270 may comprise one or more processors configured to analyze and process data and/or image information. In some embodiments, the remote data repository 280 may comprise a digital data storage facility, which may be available through the internet or other networking configuration in a "cloud" resource configuration. In some embodiments, all data is stored and all computations are performed in the local processing and data module 260, allowing fully autonomous use from a remote module.

The remote data repository 280 can be configured to store various data. For example, the remote data repository 280 can store a map of an environment (such as, e.g., a map of a clinic or an operation room). As further described with reference to FIGS. 9 and 12, the map may be generated based on data collected by multiple wearable systems over time. The map of an environment may be passed from one wearable system to another. For example, the map of the operating room may be shared between the surgeon and nurses in a surgery. The remote data repository 280 can also store medical records. These medical records may be owned by a patient, rather than being owned by the particular HCP that performs an examination or operation on the patient. Thus, the patient advantageously can control the access to the patient's sensitive patient information contained in the patient's medical record. During a patient's visit to a hospital, the patient's doctor may wear a wearable device while examining the patient. The wearable device can present the medical records on a 3D user interface. The wearable device can also be configured to allow the patient's doctor to add to the existing medical records. For example, the wearable device can allow the doctor to take a picture of the patient, to put virtual flags around a tumor, to input diagnosis using voice control, and so on. The added information may also be stored to the remote data repository 280. In some embodiments, a portion of the medical records or the map may be stored in the local processing and data module 260.

Example Environmental Sensors

The wearable system 200 can include the environmental sensors to detect objects, stimuli, people, animals, locations, or other aspects of the world around the user. The environmental sensors may include image capture devices (e.g., cameras, inward-facing imaging system, outward-facing imaging system, etc.), microphones, inertial measurement units (IMUs), accelerometers, compasses, global positioning system (GPS) units, radio devices, gyroscopes, altimeters, barometers, chemical sensors, humidity sensors, temperature sensors, external microphones, light sensors (e.g., light meters), timing devices (e.g., clocks or calendars), or any combination or subcombination thereof. In some embodiments, the environmental sensors may also include a variety of physiological sensors. These sensors can measure or estimate the user's physiological parameters such as heart rate, respiratory rate, galvanic skin response, blood pressure, encephalographic state, and so on. Environmental sensors may further include emissions devices configured to receive signals such as laser, visible light, invisible wavelengths of light, or sound (e.g., audible sound, ultrasound, or other frequencies). In some embodiments, one or more environmental sensors (e.g., cameras or light sensors) may be configured to measure the ambient light (e.g., luminance) of the environment (e.g., to capture the lighting conditions of the environment). Physical contact sensors, such as strain gauges, curb feelers, or the like, may also be included as environmental sensors.

FIG. 2B shows a schematic view of an example of various components of a wearable system comprising environmental sensors. In some embodiments, the display system 202 may be part of the wearable system 200 illustrated in FIG. 2. The display system 202 may be a mixed reality display system in some implementations. The system 202 can include various environmental sensors, e.g., sensors 24, 28, 30, 32, and 34. An environmental sensor may be configured to detect data regarding the user of the wearable system (also referred to as a user sensor) or be configured to collect data regarding the user's environment (also referred to as an external sensor). For example, a physiological sensor may be an embodiment of a user sensor while a barometer may be an external sensor. In some situations, a sensor may be both a user sensor and an external sensor. For example, an outward-facing imaging system may acquire an image of the user's environment as well as an image of the user when the user is in front of a reflective surface (such as, e.g., a mirror). As another example, a microphone may serve as both the user sensor and the external sensor because the microphone can acquire sound from the user and from the environment. In the example illustrated in FIG. 2B, the sensors 24, 28, 30, and 32 may be user sensors while the sensor 34 may be an external sensor.

As illustrated, the display system 202 may include various user sensors. The display system 202 may include a viewer imaging system 22. The viewer imaging system 22 may be an embodiment of the inward-facing imaging system 462 and/or the outward facing imaging system 464 described in FIG. 4. The viewer imaging system 22 may include cameras 24 (e.g., infrared, UV, and/or visible light cameras) paired with light sources 26 (e.g., infrared light sources) directed at and configured to monitor the user (e.g., the eyes 201*a*, 201*b* and/or surrounding tissues of the user). The cameras 24 and light sources 26 may be operatively coupled to the local processing module 260. Such cameras 24 may be configured to monitor one or more of the orientation, shape, and symmetry of pupils (including pupil sizes) or irises of the respective eyes, and/or tissues surrounding the eye, such as eyelids or eyebrows to conduct the various analyses disclosed herein. In some embodiments, imaging of the iris and/or retina of an eye may be used for secure identification of a user. With continued reference to FIG. 2B, cameras 24 may further be configured to image the retinas of the respective eyes, such as for diagnostic purposes and/or for orientation tracking based on the location of retinal features, such as the fovea or features of the fundus. Iris or retina imaging or scanning may be performed for secure identification of users for, e.g., correctly associating user data with a particular user and/or to present private information to the appropriate user. In some embodiments, in addition to or as an alternative to the cameras 24, one or more cameras 28 may be configured to detect and/or monitor various other aspects of the status of a user. For example, one or more cameras 28 may be inward-facing and configured to monitor the shape, position, movement, color, and/or other properties of features other than the eyes of the user, e.g., one or more facial features (e.g., facial expression, voluntary movement, involuntary tics). In another example, one or more cameras 28 may be downward-facing or outward-facing and configured to monitor the position, movement, and/or other features or properties of the arms, hands, legs, feet, and/or torso of a user, of another person in the user's FOV, objects in the FOV, etc. The cameras 28 may be used to image the environment, and such images can be analyzed by the wearable device to determine whether a triggering event is occurring such that the wearable device may present (or mute) the visual or audible content being presented to the user.

In some embodiments, as disclosed herein, the display system 202 may include a spatial light modulator that variably projects, through a fiber scanner (e.g., the image injection devices in FIGS. 4—420, 422, 424, 426, 428), light beams across the retina of the user to form an image. In some embodiments, the fiber scanner may be used in conjunction with, or in place of, the cameras 24 or 28 to, e.g., track or image the user's eyes. For example, as an alternative to or in addition to the scanning fiber being configured to output light, the health system may have a separate light-receiving device to receive light reflected from the user's eyes, and to collect data associated with that reflected light.

With continued reference to FIG. 2B, the cameras 24, 28 and light sources 26 may be mounted on the frame 230 (shown in FIG. 2A), which may also hold the waveguide stacks 205, 206. In some embodiments, sensors and/or other electronic devices (e.g., the cameras 24, 28 and light sources 26) of the display system 202 may be configured to communicate with the local processing and data module 260 through communication links 262, 264.

In some embodiments, in addition to providing data regarding the user, one or both of the cameras 24 and 28 may be utilized to track the eyes to provide user input. For example, the viewer imaging system 22 may be utilized to select items on virtual menus, and/or provide other input to the display system 202, such as for providing user responses in the various tests and analyses disclosed herein.

In some embodiments, the display system 202 may include motion sensors 32, such as one or more accelerometers, gyros, gesture sensors, gait sensors, balance sensors, and/or IMU sensors. The sensors 30 may include one or more inwardly directed (user directed) microphones configured to detect sounds, and various properties of those sound, including the intensity and type of sounds detected, the presence of multiple signals, and/or signal location.

The sensors 30 are schematically illustrated as being connected to the frame 230. It will be appreciated that this connection may take the form of a physical attachment to the frame 230 and may be anywhere on the frame 230, including the ends of the temples of the frame 230 which extend over the user's ears. For example, the sensors 30 may be mounted at the ends of the temples of the frame 230, at a point of contact between the frame 230 and the user. In some other embodiments, the sensors 30 may extend away from the frame 230 to contact the user 210 (shown in FIG. 2A). In yet other embodiments, the sensors 30 may not be physically attached to the frame 230; rather, the sensors 30 may be spaced apart from the frame 230.

In some embodiments, the display system 202 may further include one or more environmental sensors 34 configured to detect objects, stimuli, people, animals, locations, or other aspects of the world around the user. For example, environmental sensors 34 may include one or more cameras, altimeters, barometers, chemical sensors, humidity sensors, temperature sensors, external microphones, light sensors (e.g., light meters), timing devices (e.g., clocks or calendars), or any combination or subcombination thereof. In some embodiments, multiple (e.g., two) microphones may be spaced-apart, to facilitate sound source location determinations. In various embodiments including environment sensing cameras, cameras may be located, for example, facing outward so as to capture images similar to at least a portion of an ordinary field of view of a user. Environmental sensors may further include emissions devices configured to receive signals such as laser, visible light, invisible wavelengths of light, sound (e.g., audible sound, ultrasound, or other frequencies). In some embodiments, one or more environmental sensors (e.g., cameras or light sensors) may be configured to measure the ambient light (e.g., luminance)

of the environment (e.g., to capture the lighting conditions of the environment). Physical contact sensors, such as strain gauges, curb feelers, or the like, may also be included as environmental sensors.

In some embodiments, the display system 202 may further be configured to receive other environmental inputs, such as GPS location data, weather data, date and time, or other available environmental data which may be received from the internet, satellite communication, or other suitable wired or wireless data communication method. The processing module 260 may be configured to access further information characterizing a location of the user, such as pollen count, demographics, air pollution, environmental toxins, information from smart thermostats, lifestyle statistics, or proximity to other users, buildings, or a healthcare provider. In some embodiments, information characterizing the location may be accessed using cloud-based or other remote databases. The processing module 70 may be configured to obtain such data and/or to further analyze data from any one or combinations of the environmental sensors.

The display system 202 may be configured to collect and store data obtained through any of the sensors and/or inputs described above for extended periods of time. Data received at the device may be processed and/or stored at the local processing module 260 and/or remotely (e.g., as shown in FIG. 2A, at the remote processing module 270 or emote data repository 280). In some embodiments, additional data, such as date and time, GPS location, or other global data may be received directly at the local processing module 260. Data regarding content being delivered to the user by the system, such as images, other visual content, or auditory content, may be received at the local processing module 260 as well.

Examples of a 3D Display with Depth Planes

The human visual system is complicated and providing a realistic perception of depth is challenging. Without being limited by theory, it is believed that viewers of an object may perceive the object as being three-dimensional due to a combination of vergence and accommodation. Vergence movements (i.e., rolling movements of the pupils toward or away from each other to converge the lines of sight of the eyes to fixate upon an object) of the two eyes relative to each other are closely associated with focusing (or "accommodation") of the lenses of the eyes. Under normal conditions, changing the focus of the lenses of the eyes, or accommodating the eyes, to change focus from one object to another object at a different distance will automatically cause a matching change in vergence to the same distance, under a relationship known as the "accommodation-vergence reflex." Likewise, a change in vergence will trigger a matching change in accommodation, under normal conditions. Display systems that provide a better match between accommodation and vergence may form more realistic and comfortable simulations of three-dimensional imagery.

Figure 3:
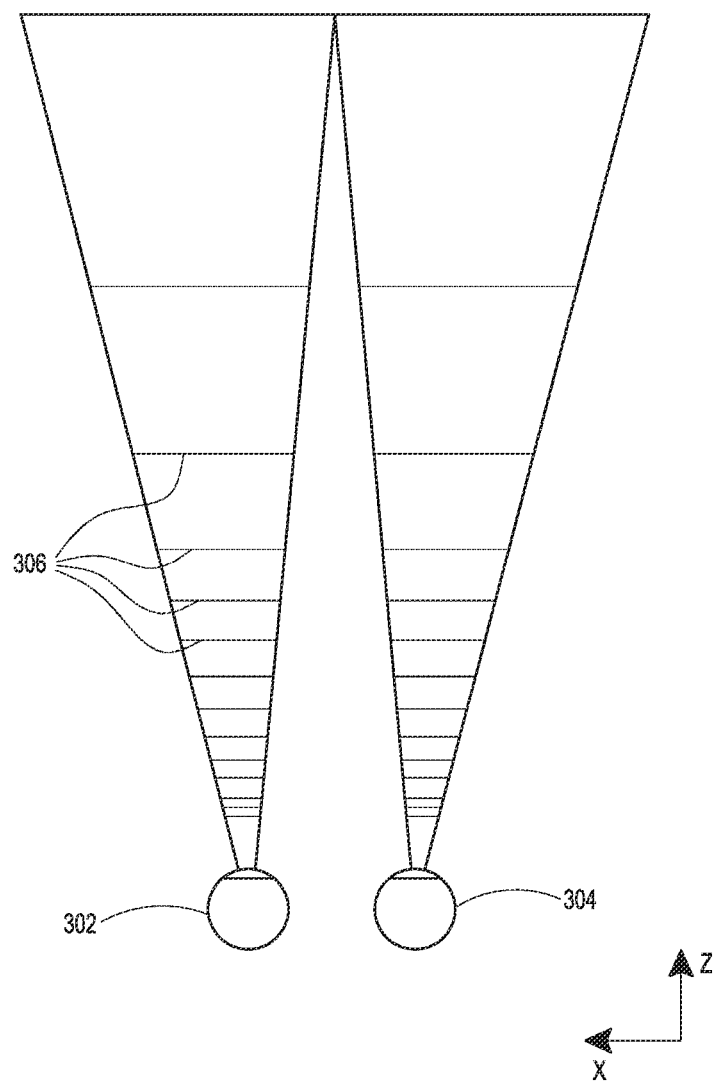
FIG. 3 schematically illustrates aspects of an approach for simulating three-dimensional imagery using multiple depth planes.

FIG. 3 illustrates aspects of an approach for simulating three-dimensional imagery using multiple depth planes. With reference to FIG. 3, objects at various distances from eyes 302 and 304 on the z-axis are accommodated by the eyes 302 and 304 so that those objects are in focus. The eyes 302 and 304 assume particular accommodated states to bring into focus objects at different distances along the z-axis. Consequently, a particular accommodated state may be said to be associated with a particular one of depth planes 306, with has an associated focal distance, such that objects or parts of objects in a particular depth plane are in focus when the eye is in the accommodated state for that depth plane. In some embodiments, three-dimensional imagery may be simulated by providing different presentations of an image for each of the eyes 302 and 304, and also by providing different presentations of the image corresponding to each of the depth planes. While shown as being separate for clarity of illustration, it will be appreciated that the fields of view of the eyes 302 and 304 may overlap, for example, as distance along the z-axis increases. In addition, while shown as flat for ease of illustration, it will be appreciated that the contours of a depth plane may be curved in physical space, such that all features in a depth plane are in focus with the eye in a particular accommodated state. Without being limited by theory, it is believed that the human eye typically can interpret a finite number of depth planes to provide depth perception. Consequently, a highly believable simulation of perceived depth may be achieved by providing, to the eye, different presentations of an image corresponding to each of these limited number of depth planes.

Waveguide Stack Assembly

Figure 4:
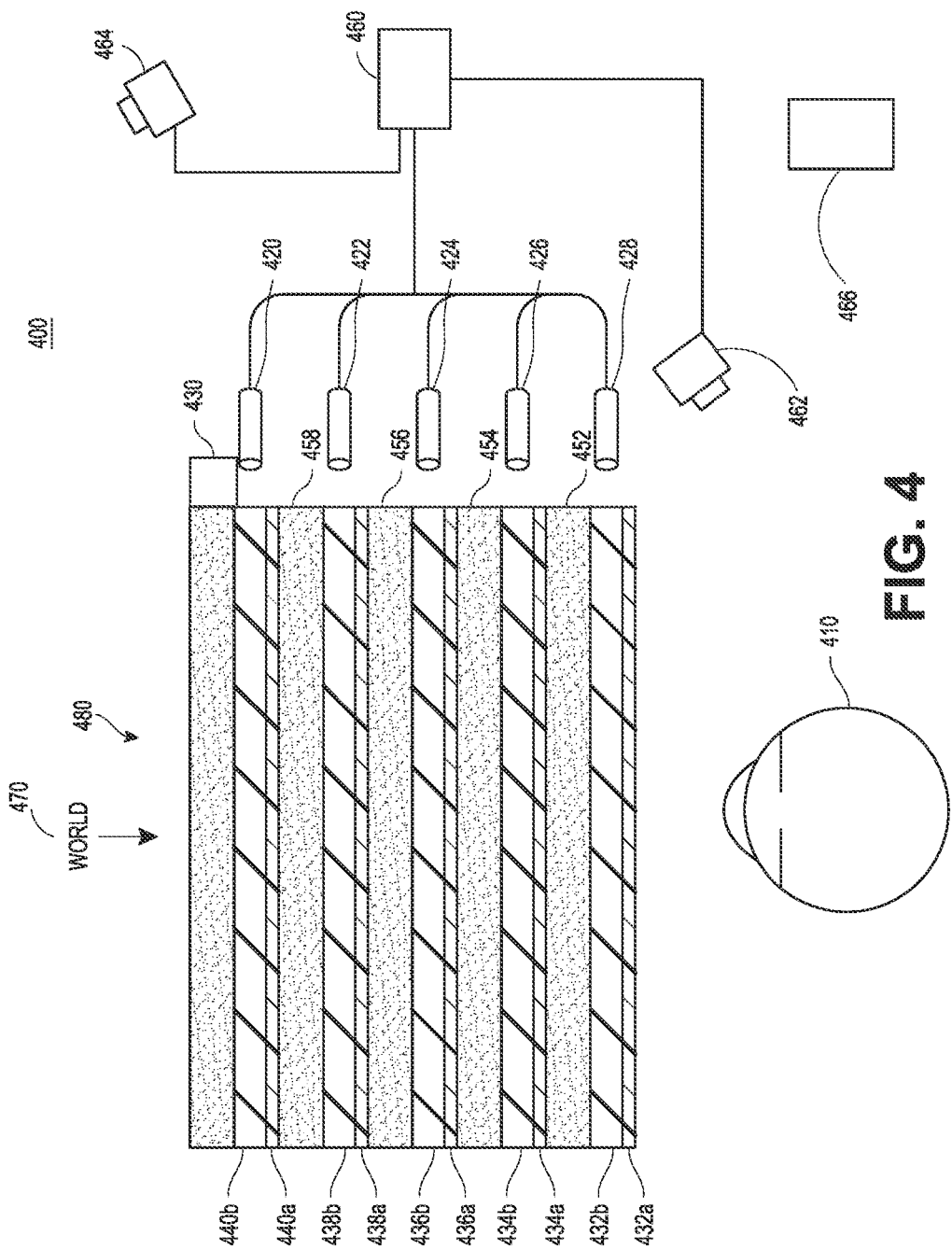
FIG. 4 schematically illustrates an example of a waveguide stack for outputting image information to a user.

FIG. 4 illustrates an example of a waveguide stack for outputting image information to a user. A wearable system 400 includes a stack of waveguides, or stacked waveguide assembly 480 that may be utilized to provide three-dimensional perception to the eye/brain using a plurality of waveguides 432b, 434b, 436b, 438b, 400b. In some embodiments, the wearable system 400 may correspond to wearable system 200 of FIG. 2, with FIG. 4 schematically showing some parts of that wearable system 200 in greater detail. For example, in some embodiments, the waveguide assembly 480 may be integrated into the display 220 of FIG. 2.

With continued reference to FIG. 4, the waveguide assembly 480 may also include a plurality of features 458, 456, 454, 452 between the waveguides. In some embodiments, the features 458, 456, 454, 452 may be lenses. In other embodiments, the features 458, 456, 454, 452 may not be lenses. Rather, they may simply be spacers (e.g., cladding layers and/or structures for forming air gaps).

The waveguides 432b, 434b, 436b, 438b, 440b and/or the plurality of lenses 458, 456, 454, 452 may be configured to send image information to the eye with various levels of wavefront curvature or light ray divergence. Each waveguide level may be associated with a particular depth plane and may be configured to output image information corresponding to that depth plane. Image injection devices 420, 422, 424, 426, 428 may be utilized to inject image information into the waveguides 440b, 438b, 436b, 434b, 432b, each of which may be configured to distribute incoming light across each respective waveguide, for output toward the eye 410. Light exits an output surface of the image injection devices 420, 422, 424, 426, 428 and is injected into a corresponding input edge of the waveguides 440b, 438b, 436b, 434b, 432b. In some embodiments, a single beam of light (e.g., a collimated beam) may be injected into each waveguide to output an entire field of cloned collimated beams that are directed toward the eye 410 at particular angles (and amounts of divergence) corresponding to the depth plane associated with a particular waveguide.

In some embodiments, the image injection devices 420, 422, 424, 426, 428 are discrete displays that each produce image information for injection into a corresponding waveguide 440b, 438b, 436b, 434b, 432b, respectively. In some other embodiments, the image injection devices 420, 422, 424, 426, 428 are the output ends of a single multiplexed display which may, e.g., pipe image information via one or more optical conduits (such as fiber optic cables) to each of the image injection devices 420, 422, 424, 426, 428.

A controller 460 controls the operation of the stacked waveguide assembly 480 and the image injection devices 420, 422, 424, 426, 428. The controller 460 includes programming (e.g., instructions in a non-transitory computer-readable medium) that regulates the timing and provision of image information to the waveguides 440b, 438b, 436b, 434b, 432b. In some embodiments, the controller 460 may be a single integral device, or a distributed system connected by wired or wireless communication channels. The controller 460 may be part of the processing modules 260 and/or 270 (illustrated in FIG. 2) in some embodiments.

The waveguides 440b, 438b, 436b, 434b, 432b may be configured to propagate light within each respective waveguide by total internal reflection (TIR). The waveguides 440b, 438b, 436b, 434b, 432b may each be planar or have another shape (e.g., curved), with major top and bottom surfaces and edges extending between those major top and bottom surfaces. In the illustrated configuration, the waveguides 440b, 438b, 436b, 434b, 432b may each include light extracting optical elements 440a, 438a, 436a, 434a, 432a that are configured to extract light out of a waveguide by redirecting the light, propagating within each respective waveguide, out of the waveguide to output image information to the eye 410. Extracted light may also be referred to as outcoupled light, and light extracting optical elements may also be referred to as outcoupling optical elements. An extracted beam of light is outputted by the waveguide at locations at which the light propagating in the waveguide strikes a light redirecting element. The light extracting optical elements (440a, 438a, 436a, 434a, 432a) may, for example, be reflective and/or diffractive optical features. While illustrated disposed at the bottom major surfaces of the waveguides 440b, 438b, 436b, 434b, 432b for ease of description and drawing clarity, in some embodiments, the light extracting optical elements 440a, 438a, 436a, 434a, 432a may be disposed at the top and/or bottom major surfaces, and/or may be disposed directly in the volume of the waveguides 440b, 438b, 436b, 434b, 432b. In some embodiments, the light extracting optical elements 440a, 438a, 436a, 434a, 432a may be formed in a layer of material that is attached to a transparent substrate to form the waveguides 440b, 438b, 436b, 434b, 432b. In some other embodiments, the waveguides 440b, 438b, 436b, 434b, 432b may be a monolithic piece of material and the light extracting optical elements 440a, 438a, 436a, 434a, 432a may be formed on a surface and/or in the interior of that piece of material.

With continued reference to FIG. 4, as discussed herein, each waveguide 440b, 438b, 436b, 434b, 432b is configured to output light to form an image corresponding to a particular depth plane. For example, the waveguide 432b nearest the eye may be configured to deliver collimated light, as injected into such waveguide 432b, to the eye 410. The collimated light may be representative of the optical infinity focal plane. The next waveguide up 434b may be configured to send out collimated light which passes through the first lens 452 (e.g., a negative lens) before it can reach the eye 410. First lens 452 may be configured to create a slight convex wavefront curvature so that the eye/brain interprets light coming from that next waveguide up 434b as coming from a first focal plane closer inward toward the eye 410 from optical infinity. Similarly, the third up waveguide 436b passes its output light through both the first lens 452 and second lens 454 before reaching the eye 410. The combined optical power of the first and second lenses 452 and 454 may be configured to create another incremental amount of wavefront curvature so that the eye/brain interprets light coming from the third waveguide 436b as coming from a second focal plane that is even closer inward toward the person from optical infinity than was light from the next waveguide up 434b.

The other waveguide layers (e.g., waveguides 438b, 440b) and lenses (e.g., lenses 456, 458) are similarly configured, with the highest waveguide 440b in the stack sending its output through all of the lenses between it and the eye for an aggregate focal power representative of the closest focal plane to the person. To compensate for the stack of lenses 458, 456, 454, 452 when viewing/interpreting light coming from the world 470 on the other side of the stacked waveguide assembly 480, a compensating lens layer 430 may be disposed at the top of the stack to compensate for the aggregate power of the lens stack 458, 456, 454, 452 below. Such a configuration provides as many perceived focal planes as there are available waveguide/lens pairings. Both the light extracting optical elements of the waveguides and the focusing aspects of the lenses may be static (e.g., not dynamic or electro-active). In some alternative embodiments, either or both may be dynamic using electro-active features.

With continued reference to FIG. 4, the light extracting optical elements 440a, 438a, 436a, 434a, 432a may be configured to both redirect light out of their respective waveguides and to output this light with the appropriate amount of divergence or collimation for a particular depth plane associated with the waveguide. As a result, waveguides having different associated depth planes may have different configurations of light extracting optical elements, which output light with a different amount of divergence depending on the associated depth plane. In some embodiments, as discussed herein, the light extracting optical elements 440a, 438a, 436a, 434a, 432a may be volumetric or surface features, which may be configured to output light at specific angles. For example, the light extracting optical elements 440a, 438a, 436a, 434a, 432a may be volume holograms, surface holograms, and/or diffraction gratings. Light extracting optical elements, such as diffraction gratings, are described in U.S. Patent Publication No. 2015/0178939, published Jun. 25, 2015, which is incorporated by reference herein in its entirety.

In some embodiments, the light extracting optical elements 440a, 438a, 436a, 434a, 432a are diffractive features that form a diffraction pattern, or "diffractive optical element" (also referred to herein as a "DOE"). Preferably, the DOE's have a relatively low diffraction efficiency so that only a portion of the light of the beam is deflected away toward the eye 410 with each intersection of the DOE, while the rest continues to move through a waveguide via total internal reflection. The light carrying the image information is thus divided into a number of related exit beams that exit the waveguide at a multiplicity of locations and the result is a fairly uniform pattern of exit emission toward the eye 304 for this particular collimated beam bouncing around within a waveguide.

In some embodiments, one or more DOEs may be switchable between "on" states in which they actively diffract, and "off" states in which they do not significantly diffract. For instance, a switchable DOE may comprise a layer of polymer dispersed liquid crystal, in which microdroplets comprise a diffraction pattern in a host medium, and the refractive index of the microdroplets can be switched to substantially match the refractive index of the host material (in which case the pattern does not appreciably diffract incident light) or the microdroplet can be switched to an index that does not match that of the host medium (in which case the pattern actively diffracts incident light).

In some embodiments, the number and distribution of depth planes and/or depth of field may be varied dynamically based on the pupil sizes and/or orientations of the eyes of the viewer. Depth of field may change inversely with a viewer's pupil size. As a result, as the sizes of the pupils of the viewer's eyes decrease, the depth of field increases such that one plane not discernible because the location of that plane is beyond the depth of focus of the eye may become discernible and appear more in focus with reduction of pupil size and commensurate increase in depth of field. Likewise, the number of spaced apart depth planes used to present different images to the viewer may be decreased with decreased pupil size. For example, a viewer may not be able to clearly perceive the details of both a first depth plane and a second depth plane at one pupil size without adjusting the accommodation of the eye away from one depth plane and to the other depth plane. These two depth planes may, however, be sufficiently in focus at the same time to the user at another pupil size without changing accommodation.

In some embodiments, the display system may vary the number of waveguides receiving image information based upon determinations of pupil size and/or orientation, or upon receiving electrical signals indicative of particular pupil sizes and/or orientations. For example, if the user's eyes are unable to distinguish between two depth planes associated with two waveguides, then the controller 460 may be configured or programmed to cease providing image information to one of these waveguides. Advantageously, this may reduce the processing burden on the system, thereby increasing the responsiveness of the system. In embodiments in which the DOEs for a waveguide are switchable between on and off states, the DOEs may be switched to the off state when the waveguide does receive image information.

In some embodiments, it may be desirable to have an exit beam meet the condition of having a diameter that is less than the diameter of the eye of a viewer. However, meeting this condition may be challenging in view of the variability in size of the viewer's pupils. In some embodiments, this condition is met over a wide range of pupil sizes by varying the size of the exit beam in response to determinations of the size of the viewer's pupil. For example, as the pupil size decreases, the size of the exit beam may also decrease. In some embodiments, the exit beam size may be varied using a variable aperture.

The wearable system 400 can include an outward-facing imaging system 464 (e.g., a digital camera) that images a portion of the world 470. This portion of the world 470 may be referred to as the field of view (FOV) and the imaging system 464 is sometimes referred to as an FOV camera. The entire region available for viewing or imaging by a viewer may be referred to as the field of regard (FOR). The FOR may include 4π steradians of solid angle surrounding the wearable system 400. In some implementations of the wearable system 400, the FOR may include substantially all of the solid angle around a user of the display system 400, because the user can move their head and eyes to look at objects surrounding the user (in front, in back, above, below, or on the sides of the user). Images obtained from the outward-facing imaging system 464 can be used to track gestures made by the user (e.g., hand or finger gestures), detect objects in the world 470 in front of the user, and so forth.

The wearable system 400 can also include an inward-facing imaging system 466 (e.g., a digital camera), which observes the movements of the user, such as the eye movements and the facial movements. The inward-facing imaging system 466 may be used to capture images of the eye 410 to determine the size and/or orientation of the pupil of the eye 304. The inward-facing imaging system 466 can be used to obtain images for use in determining the direction the user is looking (e.g., eye pose) or for biometric identification of the user (e.g., iris recognition or retinal scanning, etc.). In some embodiments, at least one camera may be utilized for each eye, to separately determine the pupil size and/or eye pose of each eye independently, thereby allowing the presentation of image information to each eye to be dynamically tailored to that eye. In some other embodiments, the pupil diameter and/or orientation of only a single eye 410 (e.g., using only a single camera per pair of eyes) is determined and assumed to be similar for both eyes of the user. The images obtained by the inward-facing imaging system 466 may be analyzed to determine the user's eye pose and/or mood, which can be used by the wearable system 400 to decide which audio or visual content should be presented to the user. The wearable system 400 may also determine head pose (e.g., head position or head orientation) using sensors such as IMUs, accelerometers, gyroscopes, etc.

The wearable system 400 can include a user input device 466 by which the user can input commands to the controller 460 to interact with the wearable system 400. For example, the user input device 466 can include a trackpad, a touchscreen, a joystick, a multiple degree-of-freedom (DOF) controller, a capacitive sensing device, a game controller, a keyboard, a mouse, a directional pad (D-pad), a wand, a haptic device, a totem (e.g., functioning as a virtual user input device), and so forth. In some cases, the user may use a finger (e.g., a thumb) to press or swipe on a touch-sensitive input device to provide input to the wearable system 400 (e.g., to provide user input to a user interface provided by the wearable system 400). The user input device 466 may be held by the user's hand during the use of the wearable system 400. The user input device 466 can be in wired or wireless communication with the wearable system 400.

Figure 5:
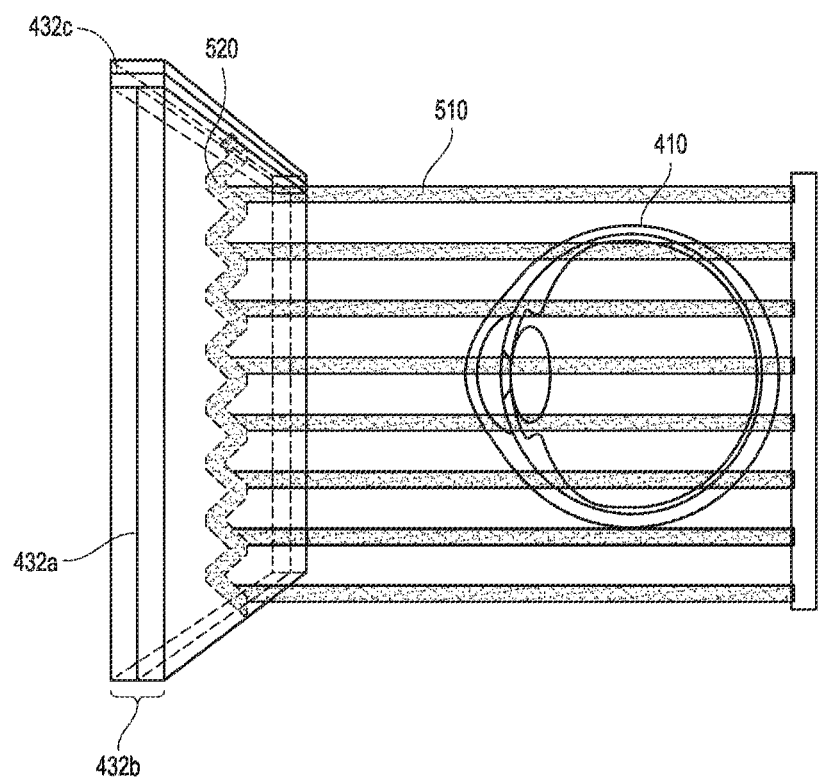
FIG. 5 shows example exit beams that may be outputted by a waveguide.

FIG. 5 shows an example of exit beams outputted by a waveguide. One waveguide is illustrated, but it will be appreciated that other waveguides in the waveguide assembly 480 may function similarly, where the waveguide assembly 480 includes multiple waveguides. Light 520 is injected into the waveguide 432b at the input edge 432c of the waveguide 432b and propagates within the waveguide 432b by TIR. At points where the light 520 impinges on the DOE 432a, a portion of the light exits the waveguide as exit beams 510. The exit beams 510 are illustrated as substantially parallel but they may also be redirected to propagate to the eye 410 at an angle (e.g., forming divergent exit beams), depending on the depth plane associated with the waveguide 432b. It will be appreciated that substantially parallel exit beams may be indicative of a waveguide with light extracting optical elements that outcouple light to form images that appear to be set on a depth plane at a large distance (e.g., optical infinity) from the eye 410. Other waveguides or other sets of light extracting optical elements may output an exit beam pattern that is more divergent, which would require the eye 410 to accommodate to a closer distance to bring it into focus on the retina and would be interpreted by the brain as light from a distance closer to the eye 410 than optical infinity.

Figure 6:
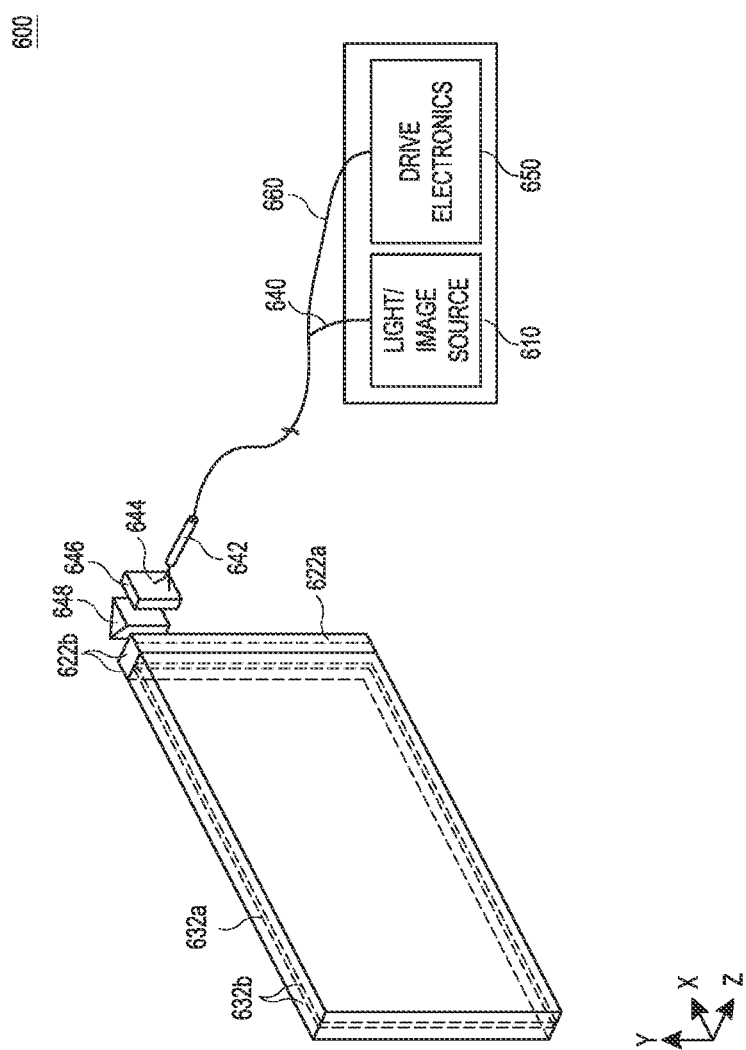
FIG. 6 is a schematic diagram showing an optical system including a waveguide apparatus, an optical coupler subsystem to optically couple light to or from the waveguide apparatus, and a control subsystem, used in the generation of a multi-focal volumetric display, image, or light field.

FIG. 6 is a schematic diagram showing an optical system including a waveguide apparatus, an optical coupler subsystem to optically couple light to or from the waveguide apparatus, and a control subsystem, used in the generation of a multi-focal volumetric display, image, or light field. The optical system can include a waveguide apparatus, an optical coupler subsystem to optically couple light to or from the waveguide apparatus, and a control subsystem. The optical system can be used to generate a multi-focal volumetric, image, or light field. The optical system can include one or more primary planar waveguides 632a (only one is shown in FIG. 6) and one or more DOEs 632b associated with each of at least some of the primary waveguides 632a. The planar waveguides 632b can be similar to the waveguides 432b, 434b, 436b, 438b, 440b discussed with reference to FIG. 4. The optical system may employ a distribution waveguide apparatus to relay light along a first axis (vertical or Y-axis in view of FIG. 6), and expand the light's effective exit pupil along the first axis (e.g., Y-axis). The distribution waveguide apparatus, may, for example include a distribution planar waveguide 622b and at least one DOE 622a (illustrated by double dash-dot line) associated with the distribution planar waveguide 622b. The distribution planar waveguide 622b may be similar or identical in at least some respects to the primary planar waveguide 632b, having a different orientation therefrom. Likewise, at least one DOE 622a may be similar or identical in at least some respects to the DOE 632a. For example, the distribution planar waveguide 622b and/or DOE 622a may be comprised of the same materials as the primary planar waveguide 632b and/or DOE 632a, respectively. Embodiments of the optical display system 600 shown in FIG. 6 can be integrated into the wearable system 200 shown in FIG. 2.

The relayed and exit-pupil expanded light is optically coupled from the distribution waveguide apparatus into the one or more primary planar waveguides 632b. The primary planar waveguide 632b relays light along a second axis, preferably orthogonal to first axis, (e.g., horizontal or X-axis in view of FIG. 6). Notably, the second axis can be a non-orthogonal axis to the first axis. The primary planar waveguide 632b expands the light's effective exit pupil along that second axis (e.g., X-axis). For example, the distribution planar waveguide 622b can relay and expand light along the vertical or Y-axis, and pass that light to the primary planar waveguide 632b which relays and expands light along the horizontal or X-axis.

The optical system may include one or more sources of colored light (e.g., red, green, and blue laser light) 610 which may be optically coupled into a proximal end of a single mode optical fiber 640. A distal end of the optical fiber 640 may be threaded or received through a hollow tube 8 of piezoelectric material. The distal end protrudes from the tube 642 as fixed-free flexible cantilever 644. The piezoelectric tube 642 can be associated with four quadrant electrodes (not illustrated). The electrodes may, for example, be plated on the outside, outer surface or outer periphery or diameter of the tube 642. A core electrode (not illustrated) is also located in a core, center, inner periphery or inner diameter of the tube 642.

Drive electronics 650, for example electrically coupled via wires 660, drive opposing pairs of electrodes to bend the piezoelectric tube 642 in two axes independently. The protruding distal tip of the optical fiber 644 has mechanical modes of resonance. The frequencies of resonance can depend upon a diameter, length, and material properties of the optical fiber 644. By vibrating the piezoelectric tube 8 near a first mode of mechanical resonance of the fiber cantilever 644, the fiber cantilever 644 is caused to vibrate, and can sweep through large deflections.

By stimulating resonant vibration in two axes, the tip of the fiber cantilever 644 is scanned biaxially in an area filling two dimensional (2-D) scan. By modulating an intensity of light source(s) 610 in synchrony with the scan of the fiber cantilever 644, light emerging from the fiber cantilever 644 forms an image. Descriptions of such a set up are provided in U.S. Patent Publication No. 2014/0003762, which is incorporated by reference herein in its entirety.

A component 646 of an optical coupler subsystem collimates the light emerging from the scanning fiber cantilever 644. The collimated light is reflected by mirrored surface 648 into the narrow distribution planar waveguide 622b which contains the at least one diffractive optical element (DOE) 622a. The collimated light propagates vertically (relative to the view of FIG. 6) along the distribution planar waveguide 622b by total internal reflection (TIR), and in doing so repeatedly intersects with the DOE 622a. The DOE 622a preferably has a low diffraction efficiency. This causes a fraction (e.g., 10%) of the light to be diffracted toward an edge of the larger primary planar waveguide 632b at each point of intersection with the DOE 622a, and a fraction of the light to continue on its original trajectory down the length of the distribution planar waveguide 622b via TIR.

At each point of intersection with the DOE 622a, additional light is diffracted toward the entrance of the primary waveguide 632b. By dividing the incoming light into multiple outcoupled sets, the exit pupil of the light is expanded vertically by the DOE 4 in the distribution planar waveguide 622b. This vertically expanded light coupled out of distribution planar waveguide 622b enters the edge of the primary planar waveguide 632b.

Light entering primary waveguide 632b propagates horizontally (relative to the view of FIG. 6) along the primary waveguide 632b via TIR. As the light intersects with DOE 632a at multiple points as it propagates horizontally along at least a portion of the length of the primary waveguide 632b via TIR. The DOE 632a may advantageously be designed or configured to have a phase profile that is a summation of a linear diffraction pattern and a radially symmetric diffractive pattern, to produce both deflection and focusing of the light. The DOE 632a may advantageously have a low diffraction efficiency (e.g., 10%), so that only a portion of the light of the beam is deflected toward the eye of the view with each intersection of the DOE 632a while the rest of the light continues to propagate through the primary waveguide 632b via TIR.

At each point of intersection between the propagating light and the DOE 632a, a fraction of the light is diffracted toward the adjacent face of the primary waveguide 632b allowing the light to escape the TIR, and emerge from the face of the primary waveguide 632b. In some embodiments, the radially symmetric diffraction pattern of the DOE 632a additionally imparts a focus level to the diffracted light, both shaping the light wavefront (e.g., imparting a curvature) of the individual beam as well as steering the beam at an angle that matches the designed focus level.

Accordingly, these different pathways can cause the light to be coupled out of the primary planar waveguide 632b by a multiplicity of DOEs 632a at different angles, focus levels, and/or yielding different fill patterns at the exit pupil. Different fill patterns at the exit pupil can be beneficially used to create a light field display with multiple depth planes. Each layer in the waveguide assembly or a set of layers (e.g., 3 layers) in the stack may be employed to generate a respective color (e.g., red, blue, green). Thus, for example, a first set of three adjacent layers may be employed to respectively produce red, blue and green light at a first focal depth. A second set of three adjacent layers may be employed to respectively produce red, blue and green light at a second focal depth. Multiple sets may be employed to generate a full 3D or 4D color image light field with various focal depths.

Other Components of the Wearable System

In many implementations, the wearable system may include other components in addition or in alternative to the components of the wearable system described above. The wearable system may, for example, include one or more haptic devices or components. The haptic device(s) or component(s) may be operable to provide a tactile sensation to a user. For example, the haptic device(s) or component(s) may provide a tactile sensation of pressure and/or texture when touching virtual content (e.g., virtual objects, virtual tools, other virtual constructs). The tactile sensation may replicate a feel of a physical object which a virtual object represents, or may replicate a feel of an imagined object or character (e.g., a dragon) which the virtual content represents. In some implementations, haptic devices or components may be worn by the user (e.g., a user wearable glove). In some implementations, haptic devices or components may be held by the user.

The wearable system may, for example, include one or more physical objects which are manipulable by the user to allow input or interaction with the AR system. These physical objects may be referred to herein as totems. Some totems may take the form of inanimate objects, such as for example, a piece of metal or plastic, a wall, a surface of table. In certain implementations, the totems may not actually have any physical input structures (e.g., keys, triggers, joystick, trackball, rocker switch). Instead, the totem may simply provide a physical surface, and the AR system may render a user interface so as to appear to a user to be on one or more surfaces of the totem. For example, the AR system may render an image of a computer keyboard and trackpad to appear to reside on one or more surfaces of a totem. For instance, the AR system may render a virtual computer keyboard and virtual trackpad to appear on a surface of a thin rectangular plate of aluminum which serves as a totem. The rectangular plate does not itself have any physical keys or trackpad or sensors. However, the AR system may detect user manipulation or interaction or touches with the rectangular plate as selections or inputs made via the virtual keyboard and/or virtual trackpad. The user input device 466 (shown in FIG. 4) may be an embodiment of a totem may, which may include a trackpad, a touchpad, a trigger, a joystick, a trackball, a rocker switch, a mouse, a keyboard, a multi-degree-of-freedom controller, or another physical input device. A user may use the totem, alone or in combination with poses, to interact with the wearable system and/or other users.

Examples of haptic devices and totems usable with the wearable devices, HMD, ARD, and display systems of the present disclosure are described in U.S. Patent Publication No. 2015/0016777, which is incorporated by reference herein in its entirety.

Example Wearable Systems, Environments, and Interfaces

A wearable system may employ various mapping related techniques in order to achieve high depth of field in the rendered light fields. In mapping out the virtual world, it is advantageous to know all the features and points in the real world to accurately portray virtual objects in relation to the real world. To this end, FOV images captured from users of the wearable system can be added to a world model by including new pictures that convey information about various points and features of the real world. For example, the wearable system can collect a set of map points (such as 2D points or 3D points) and find new map points to render a more accurate version of the world model. The world model of a first user can be communicated (e.g., over a network such as a cloud network) to a second user so that the second user can experience the world surrounding the first user.

Figure 7:
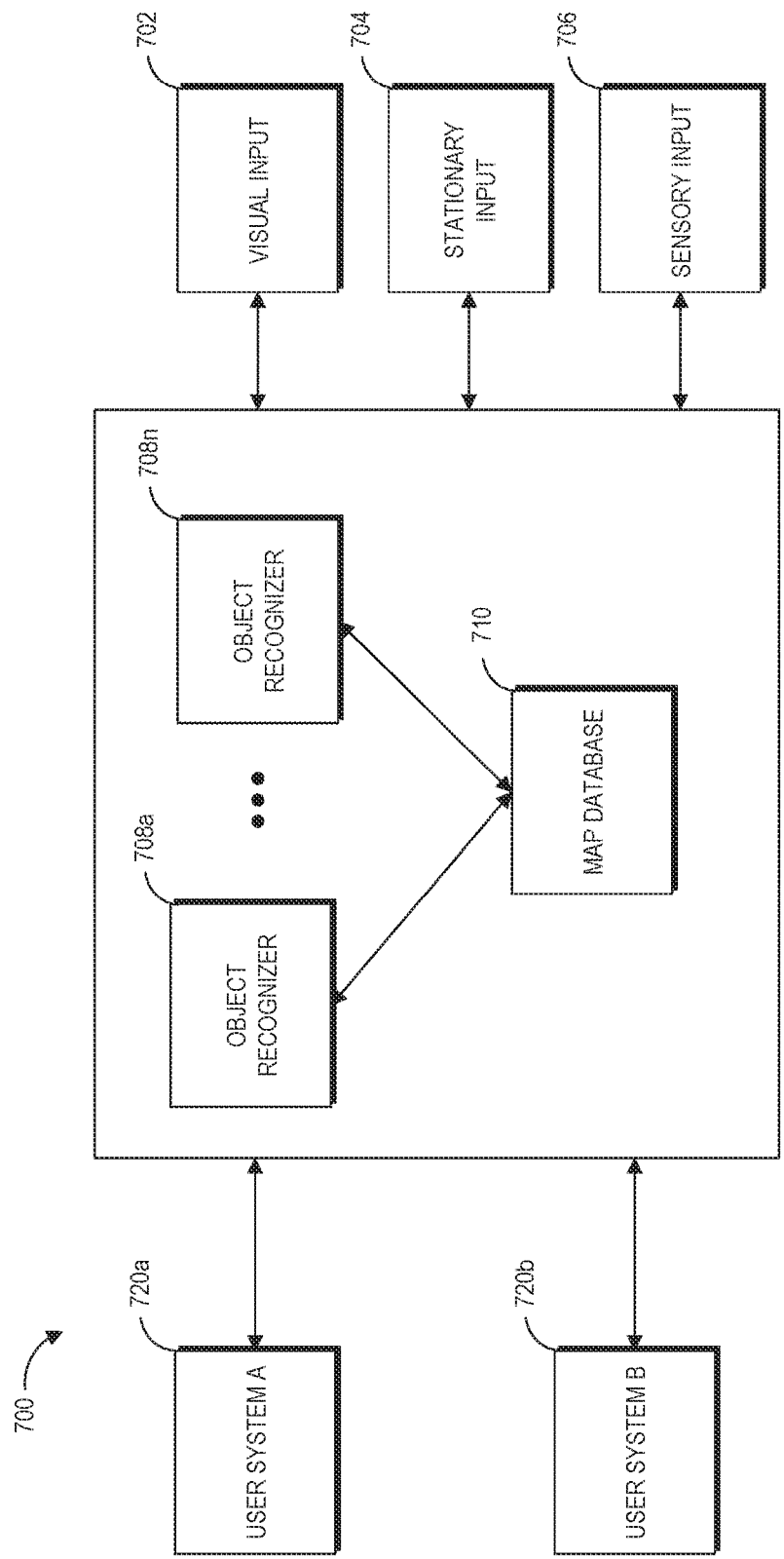
FIG. 7 is a block diagram of an example of a wearable system.

FIG. 7 is a block diagram of an example of an MR environment 700. The MR environment 700 may be configured to receive inputs (e.g., visual input 702 from the user's wearable system, stationary input 704 such as room cameras, sensory input 706 from various sensors, gestures, totems, eye tracking, user input from the user input device 466 etc.) from one or more user wearable systems 720a, 720b (e.g., wearable system 200 or display system 220) or stationary room systems (e.g., room cameras, etc.). The wearable systems 720a, 720b can use various sensors (e.g., accelerometers, gyroscopes, temperature sensors, movement sensors, depth sensors, GPS sensors, inward-facing imaging system, outward-facing imaging system, etc.) to determine the location and various other attributes of the environment of the user. This information may further be supplemented with information from stationary cameras in the room that may provide images or various cues from a different point of view. The image data acquired by the cameras (such as the room cameras or the cameras of the outward-facing imaging system) may be reduced to a set of mapping points.

One or more object recognizers 708 can crawl through the received data (e.g., the collection of points) and recognize and/or map points, tag images, attach semantic information to objects with the help of a map database 710. The map database 710 may comprise various points collected over time and their corresponding objects. The various devices and the map database can be connected to each other through a network (e.g., LAN, WAN, etc.) to access the cloud.

Based on this information and collection of points in the map database, the object recognizers 708a to 708n may recognize objects in an environment. For example, the object recognizers can recognize the patient, body parts of the patient (such as e.g., limbs, torso, head, organs, etc.), medical equipment (such as, e.g., surgical tools or medical devices), as well as other objects in a room (such as, e.g., windows, walls, etc.) or other persons in the room (such as, e.g., attending physicians, nurses, etc.). One or more object recognizers may be specialized for object with certain characteristics. For example, the object recognizer 708a may be used to recognizer faces, while another object recognizer may be used recognize scalpels. In some embodiments, if the object recognizers 708 are unable to identify an object, the object may be marked as unknown.

The object recognitions may be performed using a variety of computer vision techniques. For example, the wearable system can analyze the images acquired by the outward-facing imaging system 464 (shown in FIG. 4) to perform scene reconstruction, event detection, video tracking, object recognition, object pose estimation, learning, indexing, motion estimation, or image restoration, etc. One or more computer vision algorithms may be used to perform these tasks. Non-limiting examples of computer vision algorithms include: Scale-invariant feature transform (SIFT), speeded up robust features (SURF), oriented FAST and rotated BRIEF (ORB), binary robust invariant scalable keypoints (BRISK), fast retina keypoint (FREAK), Viola-Jones algorithm, Eigenfaces approach, Lucas-Kanade algorithm, Horn-Schunk algorithm, Mean-shift algorithm, visual simultaneous location and mapping (vSLAM) techniques, a sequential Bayesian estimator (e.g., Kalman filter, extended Kalman filter, etc.), bundle adjustment, Adaptive thresholding (and other thresholding techniques), Iterative Closest Point (ICP), Semi Global Matching (SGM), Semi Global Block Matching (SGBM), Feature Point Histograms, various machine learning algorithms.

The object recognitions can additionally or alternatively be performed by a variety of machine learning algorithms (such as e.g., support vector machine, k-nearest neighbors algorithm, Naive Bayes, neural network (including convolutional or deep neural networks), or other supervised/unsupervised models, etc.), and so forth. Once trained, the machine learning algorithm can be stored by the wearable device. Some examples of machine learning algorithms can include supervised or non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, a-priori algorithms), artificial neural network algorithms (such as, for example, Perceptron), deep learning algorithms (such as, for example, Deep Boltzmann Machine, or deep neural network), dimensionality reduction algorithms (such as, for example, Principal Component Analysis), ensemble algorithms (such as, for example, Stacked Generalization), and/or other machine learning algorithms. In some embodiments, individual models can be customized for individual data sets. For example, the wearable device can generate or store a base model. The base model may be used as a starting point to generate additional models specific to a data type (e.g., a particular user in the telepresence session), a data set (e.g., a set of additional images obtained of the user in the telepresence session), conditional situations, or other variations. In some embodiments, the wearable device can be configured to utilize a plurality of techniques to generate models for analysis of the aggregated data. Other techniques may include using pre-defined thresholds or data values.

One or more object recognizers 708 can also implement various text recognition algorithms to identify and extract the text from the images. Some example text recognition algorithms include: optical character recognition (OCR) algorithms, deep learning algorithms (such as deep neural networks), pattern matching algorithms, algorithms for preprocessing, etc.

The wearable system can also supplement recognized objects with semantic information to give life to the objects. For example, if the object recognizer recognizes a set of points to be a door, the system may attach some semantic information (e.g., the door has a hinge and has a 90 degree movement about the hinge). If the object recognizer recognizes a set of points to be a mirror, the system may attach semantic information that the mirror has a reflective surface that can reflect images of objects in the room. As another example, the object recognizer may recognize a scalpel as belonging to a set of surgical tools for performing a certain type of surgery, for example, by comparing the recognized scalpel with a database of medical instruments used in that type of surgery. The medical instruments database may be stored locally in a data repository 260 in the surgeon's wearable device or in a remote data repository 264 (e.g., in the cloud, such as data store 1238 described with reference to FIG. 12).

Over time the map database grows as the system (which may reside locally or may be accessible through a wireless network) accumulates more data from the world. Once the objects are recognized, the information may be transmitted to one or more wearable systems. For example, the MR environment 700 may include information about a scene happening in California. The environment 700 may be transmitted to one or more users in New York. Based on data received from an FOV camera and other inputs, the object recognizers and other software components can map the points collected from the various images, recognize objects etc., such that the scene may be accurately "passed over" to a second user, who may be in a different part of the world. The environment 700 may also use a topological map for localization purposes. As another example, the MR environment 700 may be an operating room where the surgeon is performing a surgery on a patient. The MR environment 700 may be shared with persons in the same operating room or outside of the operating room. For example, the surgeon may share the images in his FOV of his ARD with the medical students in a classroom. As another example, the MR environment 700 may be shared with a pathology lab so that the physicians in the pathology lab can place virtual flags around a tumor found by the surgeon in the patient's body.

Figure 8:
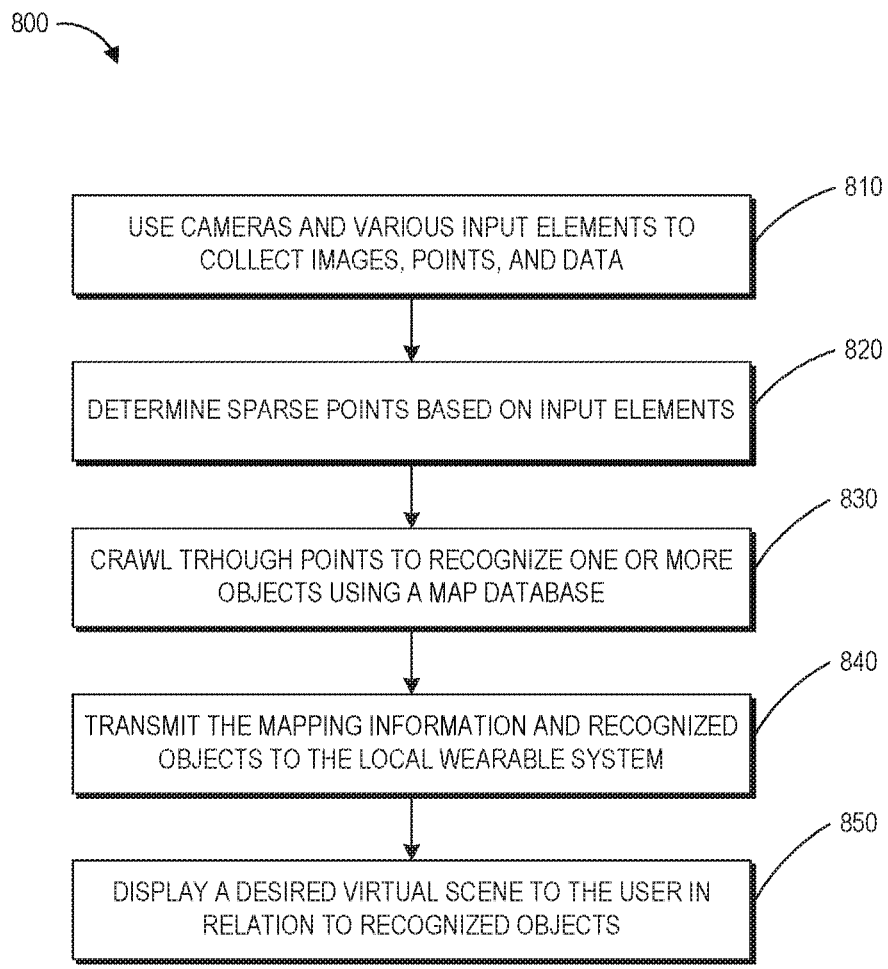
FIG. 8 is a process flow diagram of an example of a method of rendering virtual content in relation to recognized objects.

FIG. 8 is a process flow diagram of an example of a method 800 of rendering virtual content in relation to recognized objects. The method 800 describes how a virtual scene may be represented to a user of the MR system (e.g., a wearable system). The user may be geographically remote from the scene. For example, the user may be New York, but may want to view a scene that is presently going on in California, or may want to go on a walk with a friend who resides in California.

At block 810, the wearable system may receive input from the user and other users regarding the environment of the user. This may be achieved through various input devices, and knowledge already possessed in the map database. The user's FOV camera, sensors, GPS, eye tracking, etc., convey information to the system at block 810. The system may determine sparse points based on this information at block 820. The sparse points may be used in determining pose data (e.g., head pose, eye pose, body pose, and/or hand gestures) that can be used in displaying and understanding the orientation and position of various objects in the user's surroundings. The object recognizers 708a, 708n may crawl through these collected points and recognize one or more objects using a map database at block 830. This information may then be conveyed to the user's individual wearable system at block 840, and the desired virtual scene may be accordingly displayed to the user at block 850. For example, the desired virtual scene (e.g., user in CA) may be displayed at the appropriate orientation, position, etc., in relation to the various objects and other surroundings of the user in New York.

Figure 9:
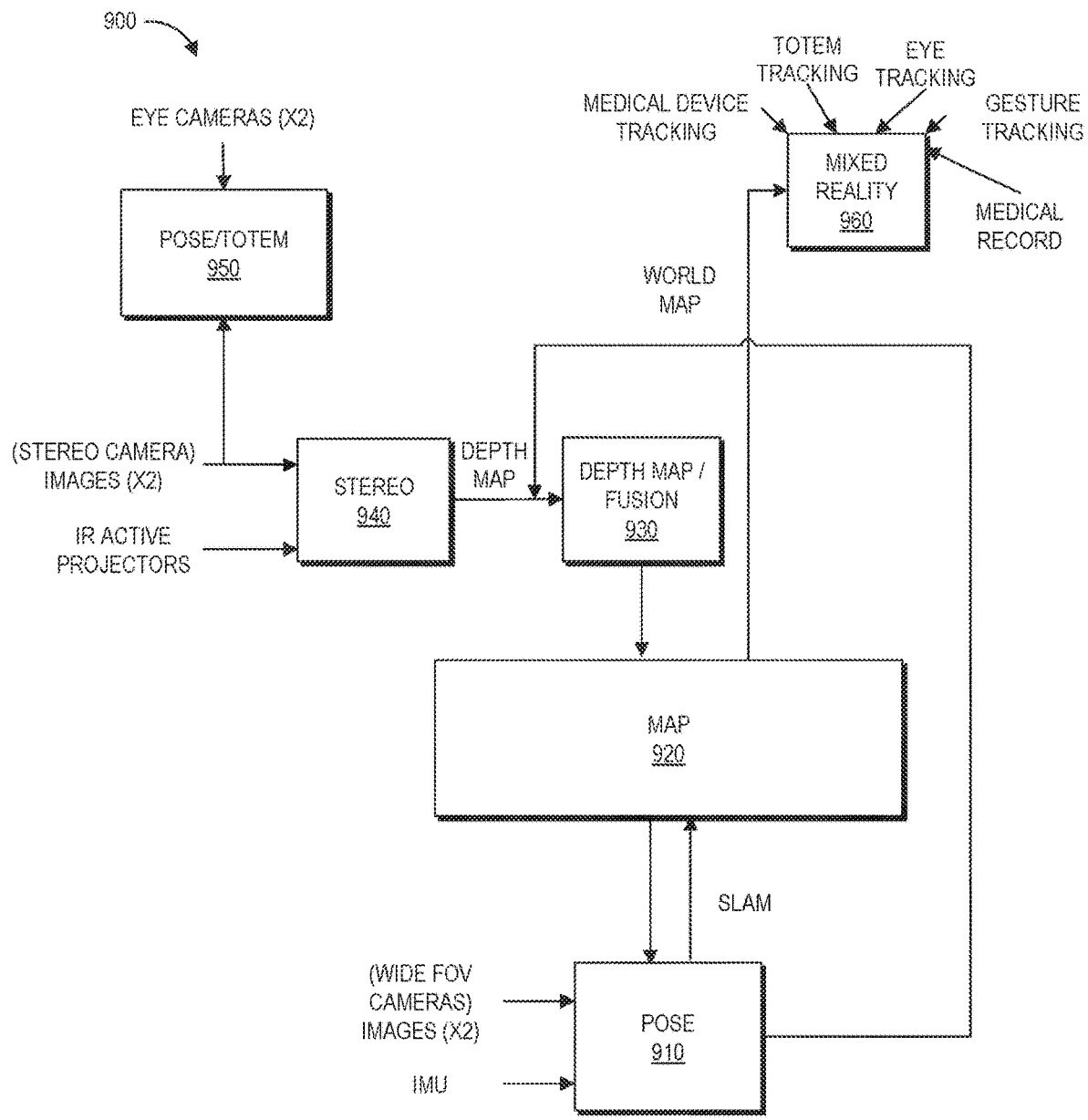
FIG. 9 is a block diagram of another example of a wearable system.

FIG. 9 is a block diagram of another example of a wearable system. In this example, the wearable system 900 comprises a map 920, which may include map data for the world (which may be part of the map database 710). The map may partly reside locally on the wearable system, and may partly reside at networked storage locations accessible by wired or wireless network (e.g., in a cloud system). A pose process 910 may be executed on the wearable computing architecture (e.g., processing module 260 or controller 460) and utilize data from the map to determine position and orientation of the wearable computing hardware or user. Pose data may be computed from data collected on the fly as the user is experiencing the system and operating in the world. The data may comprise images, data from sensors (such as inertial measurement devices, which generally comprise accelerometer and gyroscope components) and surface information pertinent to objects in the real or virtual environment.

A sparse point representation may be the output of a simultaneous localization and mapping (SLAM or V-SLAM, referring to a configuration wherein the input is images/visual only) process. The system can be configured to not only find out where in the world the various components are, but what the world is made of. Pose may be a building block that achieves many goals, including populating the map and using the data from the map.

In one embodiment, a sparse point position may not be completely adequate on its own, and further information may be needed to produce a multifocal AR, VR, or MR experience. Dense representations, generally referring to depth map information, may be utilized to fill this gap at least in part. Such information may be computed from a process referred to as Stereo 940, wherein depth information is determined using a technique such as triangulation or time-of-flight sensing. Image information and active patterns (such as infrared patterns created using active projectors) may serve as input to the Stereo process 940. A significant amount of depth map information may be fused together, and some of this may be summarized with a surface representation. For example, mathematically definable surfaces are efficient (e.g., relative to a large point cloud) and digestible inputs to other processing devices like game engines or medical devices (such as, e.g., medical imaging devices). Thus, the output of the Stereo process (e.g., a depth map) 940 may be combined in the Fusion process 930. Pose may be an input to this Fusion process 930 as well, and the output of Fusion 930 becomes an input to populating the map process 920. Sub-surfaces may connect with each other, such as in topographical mapping, to form larger surfaces, and the map becomes a large hybrid of points and surfaces.

To resolve various aspects in a mixed reality process 960, various inputs may be utilized. For example, in the embodiment depicted in FIG. 9, the location and type of medical devices may tracked and be used as inputs to determine whether the nurse has handed the physician the correct medical devices. As another example, the MR reality process 960 may allow a wearable system to present a medical record (such as the medical history, allergies, treatment recommendations, images (e.g., X-rays, ECGs, MRIs, etc.), audio (e.g., from medical examinations, etc.), etc.) of a patient while the doctor is examining or operating on the patient. The medical record may be stored locally or remotely and accessed for display to the wearer. The world map may include information regarding where the physical and virtual objects are relative to each other. This relative location information may be another valuable input to mixed reality. Pose relative to the world becomes an input as well and plays a key role to almost any interactive system.

Controls or inputs from the user are another input to the wearable system 900. As described herein, user inputs can include visual input, gestures, totems, audio input, sensory input, head or eye pose, etc. In order to move around or play a game, for example, the user may need to instruct the wearable system 900 regarding what he or she wants to do. Beyond just moving oneself in space, there are various forms of user controls that may be utilized. In one embodiment, a totem, user input device, or object such as a toy gun may be held by the user and tracked by the system. The system preferably will be configured to know that the user is holding the item and understand what kind of interaction the user is having with the item (e.g., if the totem or object is a gun, the system may be configured to understand location and orientation, as well as whether the user is clicking a trigger or other sensed button or element which may be equipped with a sensor, such as an IMU, which may assist in determining what is going on, even when such activity is not within the field of view of any of the cameras).

Hand gesture tracking or recognition may also provide input information. The wearable system 900 may be configured to track and interpret hand gestures for button presses, for gesturing left or right, stop, grab, hold, etc. For example, in one configuration, the user may want to flip through emails or a calendar in a non-gaming environment, or do a "fist bump" with another person or player. The wearable system 900 may be configured to leverage a minimum amount of hand gesture, which may or may not be dynamic. For example, the gestures may be simple static gestures like open hand for stop, thumbs up for ok, thumbs down for not ok; or a hand flip right, or left, or up/down for directional commands.

Eye tracking is another input (e.g., tracking where the user is looking to control the display technology to render at a specific depth or range). In one embodiment, vergence of the eyes may be determined using triangulation, and then using a vergence/accommodation model developed for that particular person, accommodation may be determined. Head tracking can be another input (e.g., tracking the direction of the user's head to determine which virtual or physical object the user is looking toward).

With regard to the camera systems, the example wearable system 900 shown in FIG. 9 can include three pairs of cameras: a relative wide FOV or passive SLAM pair of cameras arranged to the sides of the user's face, a different pair of cameras oriented in front of the user to handle the Stereo imaging process 940 and also to capture hand gestures and totem/object tracking 950 in front of the user's face. The cameras in the three pairs of cameras may be a part of the outward-facing imaging system 464 (shown in FIG. 4). The wearable system 900 can include eye tracking cameras (which may be a part of an inward-facing imaging system 462 shown in FIG. 4) oriented toward the eyes of the user in order to triangulate eye vectors and other information. The wearable system 900 may also comprise one or more textured light projectors (such as infrared (IR) projectors) to inject texture into a scene.

Figure 10:
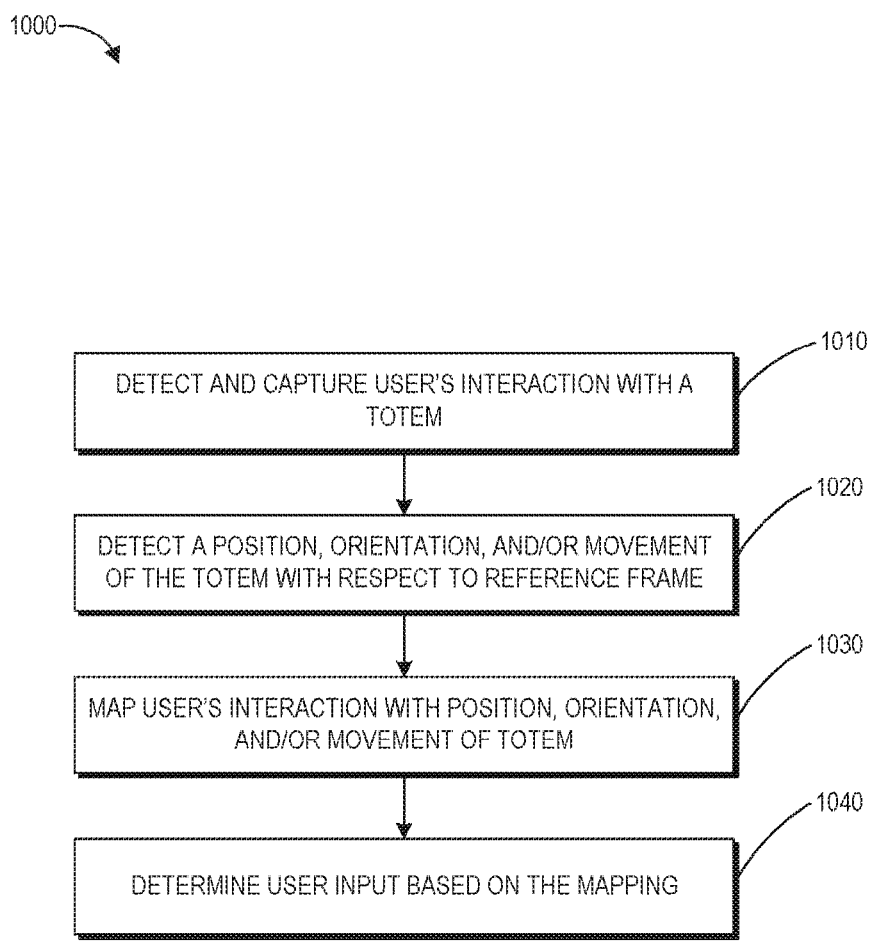
FIG. 10 is a process flow diagram of an example of a method for determining a user input to a wearable system.

FIG. 10 is a process flow diagram of an example of a method 1000 for determining user input to a wearable system. In this example, the user may interact with a totem. The user may have multiple totems. For example, the user may have designated one totem for a social media application, another totem for playing games, etc. At block 1010, the wearable system may detect a motion of a totem. The movement of the totem may be recognized through the user's FOV camera or may be detected through sensors (e.g., haptic glove, image sensors, hand tracking devices, eye-tracking cameras, head pose sensors, etc.).

Based at least partly on the detected gesture, eye pose, head pose, or input through the totem, the wearable system detects a position, orientation, and/or movement of the totem (or the user's eyes or head or gestures) with respect to a reference frame, at block 1020. The reference frame may be a set of map points based on which the wearable system translates the movement of the totem (or the user) to an action or command. At block 1030, the user's interaction with the totem is mapped. Based on the mapping of the user interaction with respect to the reference frame 1020, the system determines the user input at block 1040.

For example, the user may move a totem or physical object back and forth to signify turning a virtual page and moving on to a next page or moving from one user interface (UI) display screen to another UI screen. As another example, the user may move their head or eyes to look at different real or virtual objects in the user's FOR. If the user's gaze at a particular real or virtual object is longer than a threshold time, the real or virtual object may be selected as the user input. In some implementations, the vergence of the user's eyes can be tracked and an accommodation/vergence model can be used to determine the accommodation state of the user's eyes, which provides information on a depth plane on which the user is focusing. In some implementations, the wearable system can use raycasting techniques to determine which real or virtual objects are along the direction of the user's head pose or eye pose. In various implementations, the ray casting techniques can include casting thin, pencil rays with substantially little transverse width or casting rays with substantial transverse width (e.g., cones or frustums).

The user interface may be projected by the display system as described herein (such as the display 220 in FIG. 2). It may also be displayed using a variety of other techniques such as one or more projectors. The projectors may project images onto a physical object such as a canvas or a globe. Interactions with user interface may be tracked using one or more cameras external to the system or part of the system (such as, e.g., using the inward-facing imaging system 462 or the outward-facing imaging system 464).

Figure 11:
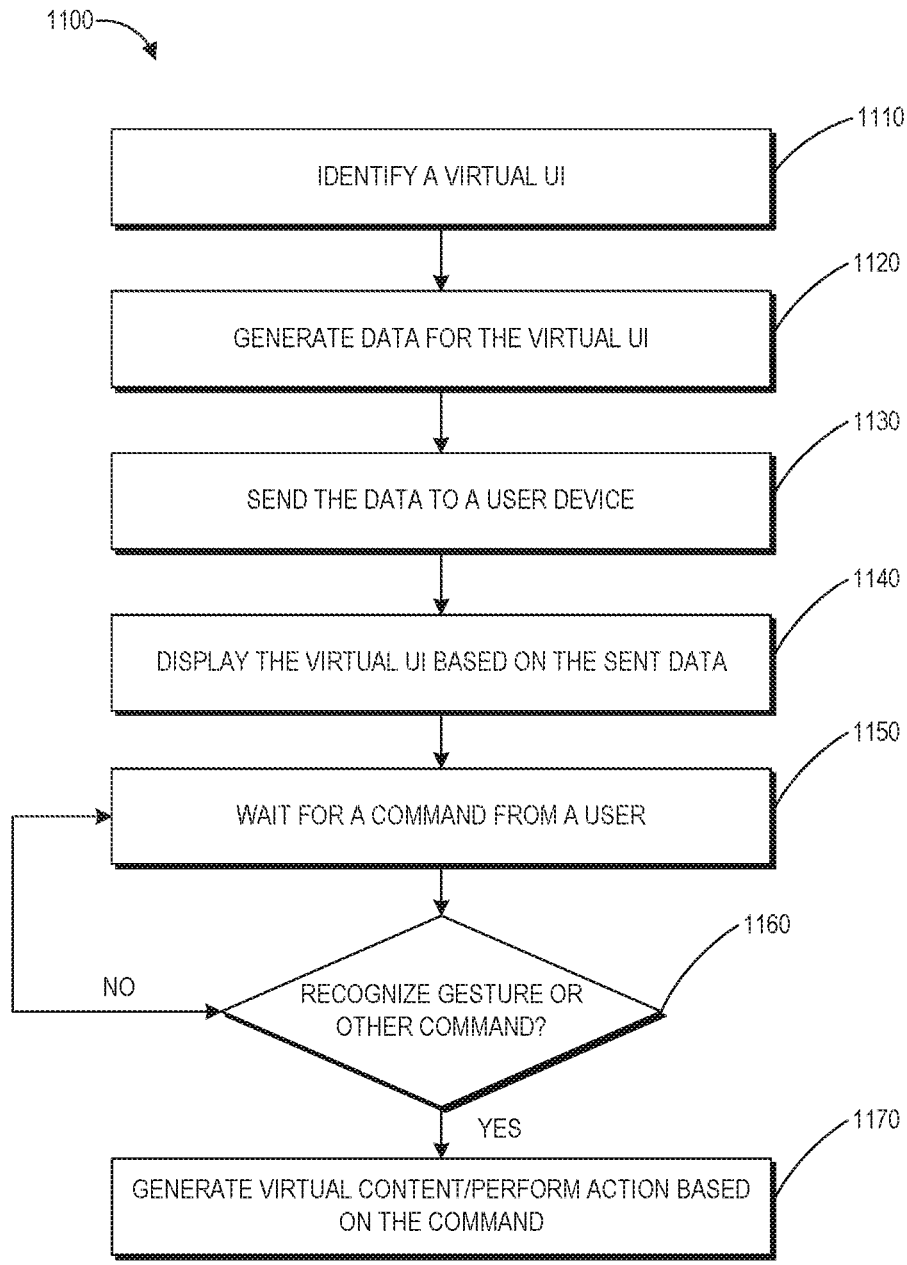
FIG. 11 is a process flow diagram of an example of a method for interacting with a virtual user interface.

FIG. 11 is a process flow diagram of an example of a method 1100 for interacting with a virtual user interface. The method 1100 may be performed by the wearable system described herein.

At block 1110, the wearable system may identify a particular UI. The type of UI may be predetermined by the user. The wearable system may identify that a particular UI needs to be populated based on a user input (e.g., gesture, visual data, audio data, sensory data, direct command, etc.). At block 1120, the wearable system may generate data for the virtual UI. For example, data associated with the confines, general structure, shape of the UI etc., may be generated. In addition, the wearable system may determine map coordinates of the user's physical location so that the wearable system can display the UI in relation to the user's physical location. For example, if the UI is body centric, the wearable system may determine the coordinates of the user's physical stance, head pose, or eye pose such that a ring UI can be displayed around the user or a planar UI can be displayed on a wall or in front of the user. If the UI is hand centric, the map coordinates of the user's hands may be determined. These map points may be derived through data received through the FOV cameras, sensory input, or any other type of collected data.

At block 1130, the wearable system may send the data to the display from the cloud or the data may be sent from a local database to the display components. At block 1140, the UI is displayed to the user based on the sent data. For example, a light field display can project the virtual UI into one or both of the user's eyes. Once the virtual UI has been created, the wearable system may simply wait for a command from the user to generate more virtual content on the virtual UI at block 1150. For example, the UI may be a body centric ring around the user's body. The wearable system may then wait for the command (a gesture, a head or eye movement, input from a user input device, etc.), and if it is recognized (block 1160), virtual content associated with the command may be displayed to the user (block 1170).

Additional examples of AR systems, UI, and user experiences (UX) are described in U.S. Patent Publication No. 2015/0016777, which is incorporated by reference herein in its entirety.

Example Medical Applications of a Head-Mounted Device

The wearable device described herein can be configured to perform various medical applications. As described with reference to FIG. 2A, the wearable device may include an HMD that are configured to present AR/MR/VR content to the wearer of the HMD. The wearable device can provide a customized medical-related application based on the user of the wearable device. For example, the user of the wearable device may be a patient and the wearable device can provide a medical record management system to be used by the patient or authorized HCPs.

Figure 12:
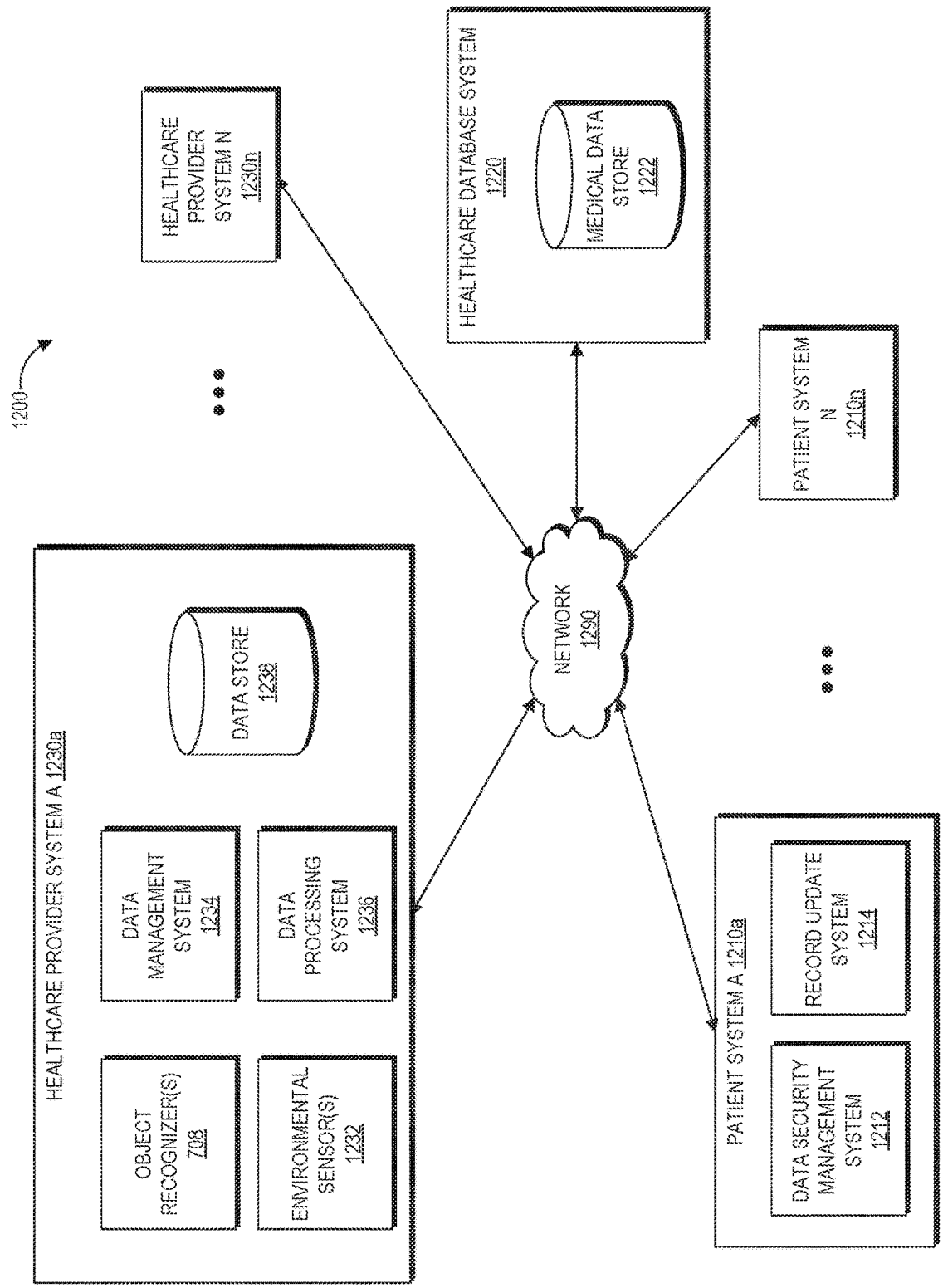
FIG. 12 illustrates an example computing environment in which multiple wearable devices and healthcare provider systems can interact with each other in a healthcare setting to provide for medical record management.

FIG. 12 illustrates an example computing environment in which multiple wearable devices and medical record management systems can interact with each other in a healthcare setting to provide medical record management. The wearable system can include a medical record management system that includes a data security management system 1212 and a record update system 1214 (shown in FIG. 12). As further described with reference to FIGS. 12, 14A, and 14B, the medical record management system can allow a user (e.g., an authorized HCP) to manage his medical records such as, e.g., adding/editing his medical records, inputting his medical history and his family's medical history, setting access privileges (also referred to as permissions) associated with his medical records, and so on. In some embodiments, the medical records are also referred to as virtual medical records.

The medical record management system can also allow the patient to view his medical records. In some embodiments, the medical record management system may allow the patient to manage some parts of his medical records such as, e.g., adding/editing his medical history and his family medical history, setting access privileges associated with his medical records, and so on. The medical record management system can also, in order to preserve the integrity and accuracy of the medical records, prohibit the patient from managing some parts of his medical records such as, e.g., adding/editing doctors' notes, doctors' diagnoses, tests results, and so on. Accordingly, in some embodiments, the system associates different access privileges to different portions of the medical record. For example, the access privileges may include read-only access to some portions of the medical record and edit access to other portions. Different users may have different access privileges to the same portion of the medical record. For example, as described above, the patient may have edit privileges for his medical or family history but read-only privileges for diagnoses, test results, etc., whereas the HCP may have read-only privileges for the patient's family history but edit privileges for the HCP's own notes or diagnosis (but not edit privileges for another HCP's notes or diagnoses).

The user of the wearable device may be a healthcare provider (HCP) who, e.g., accesses the patient's medical record or provides treatment or diagnosis to the patient. The HCP can include various entities. For example, the HCP may be a physician or other authorized party affiliated with the physician. The term physician can include a medical doctor (MD), a doctor of osteopathic medicine (DO), a physician assistant (PA), a nurse, an optometrist (OD), a podiatrist (DPM), a dentist (DDS or DDM), a veterinarian (DVM), an advanced practice medical nurse (APRN), a clinical pharmacist, a medical or nurse practitioner, a medical psychologist, or any other person authorized or licensed to prescribe medications, perform medical procedures, diagnose medical conditions, analyze medical records, etc. An HCP can include a medical receptionist or assistant who accesses, reviews, or enters information in a patient's healthcare record. Additionally or alternatively, depending on the context, the HCP can refer to an entity or organization associated with human HCPs, such as, e.g., a medical clinic, a hospital, an insurance provider, a pharmacy, or other entities that provide medical-related services.

Where the user of the wearable device is an HCP, the wearable device can include a healthcare provider system 1230 (shown in FIG. 12) to allow the user to access the patient's medical records, use the medical records to perform medical exams or operations, update the patient's medical records based on an interaction with the patient, determine whether the HCP is providing the correct care (such as, e.g., operating on the correct limb during a surgery), etc. The wearable device can use other medical information, such as, e.g., which surgical tools should be used in a certain type of surgery, alone or in combination with the patient's medical records, to enhance the quality of care and to reduce the likelihood of medical accidents. For example, the wearable device can track the surgical tools entering into the sterile region to make sure that the correct surgical tools are used or that no foreign objects (e.g., medical instruments such as, e.g., surgical tools) are accidently left inside of the patient's body.

The users of their respective wearable devices can share medical records and collaborate using the wearable devices. For example, based on the access privileges to different parts of his medical record, a patient may edit some parts of his medical records in a healthcare database using his wearable device while being able to read (but not edit) other parts of his medical record. When the patient visits a clinic, the wearable device of a doctor at the clinic can retrieve the patient's disease history and present relevant portions of the disease history in a 2D or 3D user interface to facilitate the doctor's diagnosis, analysis and interactions with the patient. The doctor's wearable device can also record (visually or audibly) the doctor's interaction with the patient, extract relevant information of the patient, and update the patient's medical records based on the relevant information. As another example, the wearable device of a surgeon can capture still or video images, audio, or input from medical devices in the operating room and a surgical site on the patient while the surgeon is performing a surgery on the patient. The wearable device of the surgeon can pass the information of the operating room and the patient to the wearable devices of a group of medical students, which allows the medical students to observe the surgery as it occurs or after the surgery is over.

Example Computing Environments for Interactions Among Users of Wearable Devices in a Medical Environment FIG. 12 illustrates an example computing environment 1200 in which multiple wearable devices can interact with each other in a healthcare setting. The example computing environment 1200 in FIG. 12 includes healthcare provider systems (e.g., healthcare provider system A 1230*a* through healthcare provider system N 1230*n*), patient systems (e.g., patient system A 1210*a* through patient system N 1210*n*), and a healthcare database system 1220. The HCP systems, the patient systems, and the healthcare database system 1220 can communicate with each other using the network 1290. The network 1290 may be a LAN, a WAN, a peer-to-peer network, radio frequency, Bluetooth, Wi-Fi, a cloud based network, or any other type of communication network. In certain implementations, the computing environment 1200 can provide a centralized healthcare database for the users of the wearable devices. The computing environment 1200 can allow users of the wearable devices to input, edit, organize, and access data in the centralized healthcare database.

To simplify discussion and not to limit the present disclosure, FIG. 12 only illustrates in detail one HCP system and one patient system. Other HCP systems may include similar functionalities as the HCP system A 1230*a*. Other patient systems may also include similar functionalities as the patient system A 1210*a*.

Examples of a Healthcare Provider System

At least a portion of the HCP system 1230*a* may be part of a wearable device. The HCP 1230*a* includes one or more object recognizer(s) 708, environmental sensors 1232, a data management system 1234, a data processing system 1236, and a data store 1238. The HCP system 1210*a* may include fewer or more systems and components as described. For example, in some embodiments, the HCP system 1230*a* may not have the data processing system 1236. Rather, the data processing system 1236 may be part of the healthcare database system 1220. In other embodiments, the HCP system 1230*a* may include more systems or functionalities that facilitate the medical care of patients. One or more systems of the HCP system A 1230*a* may be combined or be part of another system. For example, the object recognizer(s) 708 may be part of the data processing system 1236.

Object Recognizers

The object recognizer(s) 708 can be used to recognize objects in the user's environment. As described with reference to FIG. 7, the object recognizer(s) 708 can apply computer vision algorithms (in addition to or in alternative to machine learning algorithms) to identify medical equipment, documents, faces, etc., in the user's environment. The wearable device can also attach semantic information to the objects. As further described with reference to FIG. 25, the wearable device can use an object recognizer to detect or track a surgical instrument or a medical device in a FOV of the wearable device or the user of the wearable device. Additionally, the wearable device can identify a medical device (e.g., an ultrasound probe) and connect to the device via a wired or a wireless network. For example, the wearable device can scan for messages broadcasted by network-enabled medical devices in its vicinity and wirelessly connect to such devices. The wearable device can receive data from the medical device and present information related to the received data to the wearer of the device (e.g., images from an imaging device, sensor data from a probe (e.g., thermometer), and so forth). In some embodiments, the wearable device may provide a user interface (UI) that permits the wearer (e.g., a surgeon) to access or control a medical device. Additionally or alternatively, the wearable device may include a near field communication (NFC) interface that is configured to communicate over a short range (e.g., about 10 cm) with an NFC enabled medical device to exchange information, identify each other, bootstrap to a wireless connection with higher bandwidth, etc. The NFC interface and the NFC enabled medical device may operate in passive or active modes.

The surgical instrument may be associated with semantic information. For example, the semantic information may include indications that the surgical instrument is part of an instrument set used for amputation. The semantic information can also include the functions of the surgical instrument, such as, e.g., stopping blood from spraying, stitching an open wound, etc.

Environmental Sensors

The environmental sensors 1232 can include various sensors described with reference to FIGS. 2A, 2B, and 4. For example, the environmental sensors 1232 may include the user sensors 24, 28, 30, 32, the external sensor 34 described in FIG. 2B, the microphone 232 in FIG. 2A, the sensors in the outward-facing imaging system 464 and the sensors in the inward-facing imaging system 462 in FIG. 4, etc. The environment sensors 1232 can be configured to acquire data of the user's environment and data of the user. For example, the microphone 232 can acquire the audio data associated with the phrases spoken by the HCP or a patient. As another example, the outward-facing imaging system 464 can image the patient or an environment of the user. The data acquired by the one or more environmental sensors 1232 can be communicated to another system (or sensor) such as the object recognizer(s) 708 for identifying physical objects in the user's environment or the data processing system 1236 to extract relevant medical information.

Data Processing System

The HCP system A 1230a can also include a data processing system 1236. The data processing system 1236 can be configured to extract relevant information from data acquired by the environmental sensors 1232, data received from a patient system 1210, or data accessed from the healthcare database system 1220 or the data store 1238. The data processing system 1236 can process audio data (for example acquired from the microphone 232). For example, the data processing system 1236 can parse the audio data to identify the content of the speech by applying various speech recognition algorithms, such as, e.g., hidden Markov models, dynamic time warping (DTW)-based speech recognitions, neural networks, deep learning algorithms such as deep feedforward and recurrent neural networks, end-to-end automatic speech recognitions, machine learning algorithms (described with reference to FIG. 7), or other algorithms that uses acoustic modeling or language modeling, etc. The data processing system 1236 can also apply voice recognition algorithms which can identify the identity of the speaker, such as whether the speaker is a certain patient or the patient's doctor. The data processing system 1236 can use various machine learning algorithms described with reference to FIG. 7 to perform the voice recognition.

The data processing system 1236 can also be configured to process images. For example, the data processing system 1236 can apply one or more computer vision algorithms described with reference to the object recognizer(s) 708 to identify objects or persons in an image. In some embodiments, the object recognizer(s) 708 may be part of the data processing system 1236.

The data processing system 1236 can also perform text recognition. For example, an image may include a scanned copy of the patient's medical history. The data processing system 1236 can extract the text in the image using one or more text recognition algorithms, such as, e.g., character recognition algorithms, deep learning algorithms (such as deep neural networks), pattern matching algorithms, algorithms for pre-processing, etc.

In some embodiments, the data processing system 1236 can extract relevant information from the data acquired by the environmental sensors. For example, an image acquired by the data processing system 1236 may include a face of the nurse and a face of the patient. The data processing system 1236 can use facial recognition techniques to detect the faces in the image. The data processing system 1236 can further identify the face of the patient, for example, based on the previous image of the patient. As another example, the data processing system 1236 can use a machine learning algorithm to detect a keyword spoken by the user and identify the sentence including the keyword.

Some or all of the audio, visual, extracted text, or other information obtained or processed by the wearable device can be stored in the patient's medical record. For example, an audiovisual recording of a doctor's examination of the patient can be stored in the medical record. As another example, the patient may describe medical problems which he is experiencing, the doctor's wearable device may record and process the patient audio data, and store the information related to the medical problems in the patient's medical record or display the information to the doctor (see, e.g., FIG. 15). As yet another example, the HCP's wearable device may detect and record signs (e.g., eye movements, symptoms on the patient's skin, etc.) during the examination.

Although the example computing environment 1200 shows that the data management system 1234 is as part of the HCP system A 1230a, in some embodiments, at least a portion of the data processing system 1236 is part of the healthcare database system 1220.

Data Management System

The data management system 1234 can be configured to update and manage a patient's medical records. In certain implementations, the data management system 1234 can include a 2D or 3D user interface. As described with reference to FIGS. 10 and 11, a user of a wearable device can view the patient's medical records using the 2D or 3D user interface. The user can also edit the medical records using poses or the user input device 466, such as, e.g., head poses, gestures, voice input, totem, etc.

The data management system 1234 can receive data from the data processing system 1236, object recognizer(s) 708, or environmental sensor(s) 1232. The data management system 134 can communicate with the healthcare database system 1220 to update the patient's virtual medical records based on the received data. For example, the data management system 1234 may receive a patient's diagnosis from a doctor. The data management system 1234 can communicate an instruction to the database management system 1220 to add the diagnosis to the patient's medical record.

The data management system 1234 can also manage data sharing with another system, such as a patient system or another healthcare provider system. For example, the HCP system A 1230a may be associated with a surgeon who is performing a surgery in an operating room. The data processing system 1236 can identify people (such as e.g., nurses or other physicians) in the operating room using facial recognition techniques. The data management system 1234 can receive the identities of the people in the operating room from the data processing system 1236. The data management system 1234 can automatically share the one or more virtual items (such as, e.g., the patient's physiological data) on the 2D or 3D user interface of the wearable device of the surgeon with the identified people. The data management system 1234 can also share the images acquired by the outward-facing imaging system 464 of the surgeon's wearable device or other information (e.g., audio) collected by the surgeon's wearable device with the wearable devices of the identified people in the operating room.

Although the data management system 1234 in FIG. 12 is illustrated as part of the HCP system A 1230a, in some embodiments, at least a portion of the data management system 1234 is part of the healthcare database system 1220.

Data Store

The data store 1238 can be configured to store various algorithms (e.g., as implemented by computer executable codes), such as computer vision algorithms, speech recognition algorithms, voice recognition algorithms, text recognition algorithms, machine learning algorithms, etc. As described with reference to the data processing system 1236, these algorithms may be applied by the data processing system 1236 to process data acquired by the environmental sensor(s) 1232. In certain embodiments, the data store 1238 may include a copy of a patient's virtual medical record. For example, due to large file sizes, the HCP system A 1230*a* can preload a portion of the patient's prior medical images in the data store 1238 before the patient's scheduled time for visiting the HCP. When the patient visits the HCP, the HCP can view the virtual medical records preloaded to the data store 1238 to avoid delays for retrieving images from a remote location, such as the medical data store 1222.

The data store 1238 can also store data acquired or generated by other systems of the HCP provider system A 1230*a*. For example, the data store 1238 can store data acquired by the environmental sensor(s) 1232 while a patient is interacting with an HCP. The data store 1238 can also store data associated with the data processing system 1236. For example, the data processing system 1236 can generate a transcript of a conversion between the patient and an HCP and communicate the transcript for storage by the data store 1238. The data store 1238 can also store patient data acquired by the patient's wearable device. The patient data can be analyzed using various machine learning algorithms for determining the patient's habits, gait, physiological information such as heart rate, blood pressure, etc. The patient data can also be used to perform eye tracking or head pose tracking as described with reference to FIGS. 2A, 2B, and 4.

A portion of the data stored by the data store 1238 may be communicated to the healthcare database system 1220. For example, the transcript of the conversation between the patient and the HCP can be added to the patient's virtual medical record stored in the medical data store 1222 of the healthcare database system 1220. As another example, the patient data (e.g., as acquired by the patient's wearable device) can auto populate into a patient data management system (which may be part of the healthcare database system 1220 or the healthcare provider system(s) 1230) for later analysis or review by the patient or an HCP. As described herein, the access privilege to patient data can be customized such that the patient owns access to all of his or her own personal data and can select who to share it with and how much is shared.

Examples of a Patient System

The patient system A 1210*a* includes a data security management system 1212 and a record update system 1214. The patient system A 1210*a* may include fewer or more systems and components as described. For example, the patient system A 1210*a* can include a local data store, or a remote data store (e.g., a cloud-based data store) for storing data acquired or generated by the patient system A 1210*a*. In other embodiments, the patient system A 1210*a* may include more systems and/or functionalities that facilitate the medical care of patients. One or more systems of the patient system A 1210*a* may be combined or be part of another system. For example, a portion of the record update system 1214 may be part of the healthcare database system 1220.

The patient system A 1210*a* may be part of an wearable device associated with a patient. Although not shown in FIG. 12, the patient system A 1210*a* can also include environmental sensors for acquiring information of the patient and the patient's environment. The patient system A 1210*a* can also include a 3D user interface configured to allow user interactions with physical objects or virtual objects via the user input device 466 or poses.

Data Security Management System

Patient medical record information is highly personal and confidential to a particular patient. A patient may wish to share only a portion of such information with certain HCPs. For example, a patient may wish to permit a receptionist at a doctor's office to access only patient name, address, and appointment information to schedule an office visit whereas the patient may wish to permit a treating physician access to only the information pertaining to the physician's specialty (e.g., a cardiologist would be permitted access to records related to the patient's heart and body functions but not information related to the patient's visit with a psychologist). Embodiments of the data security management systems described herein can be used to preserve confidentiality of patient medical records (e.g., as required by state or federal licensing laws such as HIPAA) and to permit access to only portions of the medical record on a need-to-know basis.

The data security management system 1212 can be configured to allow a patient to manage access privileges associated with his medical records. The patient can specify the access privileges via the 3D user interface. Access privileges may be used to determine whether the virtual medical record (or a portion of the virtual medical record) may be viewed, edited, added, or deleted by an account of a user. The user may be an entity such as, e.g., an HCP, a medical insurance provider, a patient's family member, a patient, etc. For example, the patient can add, delete, or edit healthcare providers to whom the patient wants to give permission for accessing the patient's virtual medical records.

The access privileges can also involve whether the account has authorizations to manage the access privileges of another device or account (also referred to herein as delegate access). For example, a patient may give his primary care physician permissions to the patient's full medical record. The physician in turn can allow his nurse to view a portion of the patient's medical record (such as the patient's address and medical insurance information). The access privileges can be associated with a time limit which indicates how long a user has permission to access the patient's medical records. The patient may edit the time limit. The patient may receive a notification when a user's access privilege is about to expire. The patient can decide whether to extend the time limit or update the access privilege of that user. For example, a patient's primary care physician may have permissions to access the patient's medical record for a period of five years. The patient may receive a notification asking whether the patient wants to extend the physician's access privilege at the end of the five-year period. If the patient has stopped seeing the physician, the patient can choose not to extend the physician's five-year access privilege and the physician may no longer have access to the patient's medical record. As another example, a patient may give an orthopedist an access privilege for treating his broken ankle. The access privilege may last from a first appointment to a final appointment. At the final appointment, if the orthopedist informs the patient that he needs more time to treat the patient's broken ankle, the patient can extend the time limit associated with the orthopedist's access privilege for another time period. Otherwise, the time limit will end, and the orthopedist's access privilege to the patient's medical file will expire. Accordingly, access privileges can include a time limit or an action limit (e.g., successful completion of the medical procedure).

In some embodiments, a patient may receive a notification when an entity delegates access to another entity. For example, the patient's primary HCP can refer the patient to a secondary HCP, who might be a specialist. The primary HCP may delegate its access privilege of the patient's medical record to the secondary HCP. The data security management system 1212 may receive a notification from the primary HCP or from the healthcare database system 1220 indicating that the secondary HCP now has access to the patient's record. The patient can overwrite the primary HCP's delegation. For example, the primary HCP may initially allow the secondary HCP to access the patient's full medical record. But the patient may edit this delegation by specifying that the secondary HCP only has access to a portion of his virtual medical records. As another example, the patient can revoke the access privileges of the secondary HCP unless the secondary HCP meets certain criteria. In certain implementations, the patient can specify that an HCP may need to seek the patient's approval if the HCP wants to delegate access to a certain entity. For example, a patient may require a hospital to inform the patient or obtain the patient's approval if the hospital delegates access to a pharmaceutical representative.

Various levels of access privileges may be attached to virtual medical records. For example, the levels of access privileges may include a first level of access privilege and a second level of access privilege. The first level of access privilege may include permissions to view, edit, add, and delete the patient's entire medical record but the first level of access privilege may not include the permission to delegate access. The second level of access privilege may include permission to view the patient's entire medical record.

Different entities may have different levels of access privileges. The wearable device (of a patient or an HCP) or the healthcare database system 1220 may store a hierarchy of access privileges. As an example, the level access privilege of a doctor may be higher than that of a nurse, which is in turn higher than the access privilege of a receptionist who schedules office visits. Accordingly, the doctor may be able to view more information of a patient's virtual medical record than the nurse. As an example, the doctor may be able to view the images obtained from a patient's MRI exam as well as the date of the MRI exam. But the nurse may only be able to view the date of the MRI exam because the date of the MRI exam may have sufficient information for the nurse to schedule the patient's next visit. And the receptionist may only be able to view the patient's name, contact information, and office visit schedule.

The levels of access privileges may be associated with one or more access criteria. The access criteria may be based on characteristics of virtual medical records. The characteristics of the virtual medical records may include a type, content, date, entities which created the medical record, etc. For example, the patient may only allow an entity to edit his medical records in the past 12 months. As another example, the patient may only allow his insurance provider to view the records associated with the patient's surgery at a certain hospital. As yet another example, the patient may set a portion of the medical record as private (which, for example, only the patient himself has access) if the portion includes certain words. In certain implementations, the access privilege may automatically be attached if the characteristics of the virtual medical record meet a certain access criterion. For example, where the patient allows an HCP to access his medical records created within the past 12 months, a new medical image associated with the patient's exam today may be automatically become accessible to the HCP.

Additionally or alternatively, the access criteria may also be based on the characteristics of an entity, such as, e.g., a type of an entity (e.g., a hospital v. a pharmaceutical sales representative), a location of the entity (e.g., whether the entity is outside or inside a certain geographical region), etc. For example, once the patient grants permissions to the HCP for accessing the patient's medical record, the HCP can in turn allow another entity to view the medical records created by the HCP itself. In some embodiments, a wearable device of an authorized user can monitor the user's activities to determine whether to continue to display the virtual medical records. For example, the wearable device can automatically save the medical records and stop displaying the records after the wearable device detects that the user no longer wears the wearable device. This advantageously can prevent an unauthorized person from wearing the wearable device and viewing the patient's medical records. For example, the wearable device can use the eye-tracking camera to image the wearer's eye (or eyes) and compare an iris or retinal scan with a database of authorized users of the wearable device to determine that the patient (and not a third party) is wearing the wearable device. If the third party is wearing the wearable device, the wearable device can stop displaying the medical record, prevent access to the medical record, communicate an alert that there may be unauthorized attempted access to the medical record, etc.

Although in the examples, the access privilege of a virtual medical record are associated with a user, the access privileges may also be associated with a computing device. For example, a computer in an exam room may have a different level of access privilege than a computer in a doctor's office. The computer in the exam room may only be able to access information of the patient's previous exams while the computer in the doctor's office may have access to the patient's family medical history as well as the patient's previous exams.

Record Update System

A patient can interact with his medical records using the record update system 1214. The record update system 1214 may be configured to include functionalities performed similar to the data processing system 1236 and the data management system 1234. For example, the record update system 1214 can transcribe the user's conversation with his doctor and communicate the transcribed conversation for storage by the medical data store 1222. As another example, the patient can input, via the 3D user interface of his wearable device, his medical histories. The record update system 1214 can add the inputted medical histories to the patient's virtual medical records stored in the healthcare database system 1220. In some embodiments, before the patient's medical records are submitted to an insurance company for reimbursement, the medical records can be reviewed or approved by an HCP. The HCP can review, update, or approve the medical records using the HCP system 1230.

Examples of a Healthcare Database System

The healthcare database system 1220 can be configured to store and manage medical related data such as, e.g., virtual medical records of patients as well as information related to medical exams/procedures (e.g., processes of performing a certain medical exam, medical equipment/instruments required in a medical exam or surgery, etc.). The healthcare database system 1220 may be implemented as part of one or more servers. In some embodiments, the healthcare database system 1220 includes a centralized healthcare database for users of the wearable devices. For example, the healthcare database system 1220 can include a medical data store 1222 for storing the patients' virtual medical records. Advantageously, in some embodiments, the virtual medical records are owned by a patient (rather than an HCP). Accordingly, the patient can control who accesses or modifies his medical record and can ensure that his medical record is complete, because any updates made by an HCP will be to the patient's medical record rather than to a separate, HCP-owned record. As further described with reference to FIGS. 14A and 14B, the patient can manage levels of access privileges associated with his virtual medical records.

The healthcare database system 1220 can include control instructions for adding, editing, accessing, or organizing virtual medical records. For example, the database system 1220 can receive an input from a user of a wearable device. The user may be an HCP or a patient. The input may include an update (such as, e.g., by adding, deleting, editing) to a virtual record. In response to the input, the healthcare database system 1220 can identify the virtual record that needs to be updated and implement the update accordingly. As another example, the healthcare database system 1220 can receive an access privilege setting from a patient system 1210. The healthcare database system 1220 can automatically attach the access privilege setting to the patient's medical records. As yet another example, the healthcare database system 1220 can receive a request from an HCP system 1230 to retrieve a virtual medical record. The healthcare database system 1220 can identify the virtual medical record based on the request and return the virtual medical record to the HCP system 1230. In some embodiments, the healthcare database system 1220 checks whether the HCP system 1230 meets a required level of access privilege associated with the virtual medical record. The healthcare database system 1220 can return the virtual medical record if the HCP system 1230 meets the required level of access privilege. In certain implementations, if the HCP system 1230 does not meet the required level of access privilege, the healthcare database system 1220 may return only the portion of the virtual medical record that is accessible by the HCP system 1230. For example, the HCP system 1230 may request all information associated with a patient's exam. However, the HCP system 1230 may only be allowed to view the exam date and location but not allowed to view the images of the exam. Accordingly, the healthcare database system 1220 may return only the date and location of the exam to the HCP system 1230 while not providing the images of the exam to the HCP system 1230.

The healthcare database system 1220 can also organize data stored in the medical data store 1222, or data stores associated with the HCP systems 1230 or patient systems 1210. Data can be organized in a variety of ways. For example, data may be organized based on patients, HCPs, medical settings, types of procedure, user access permissions/privacy settings, locations, action items associated with the data, etc., alone or in combination.

As an example of organizing data based on patients or HCPs, virtual medical records of the same patient or the same HCP may be grouped together. As an example of organizing data based on medical settings, data associated with radiology may be stored together while data associated with surgeries may be compiled together. As an example of organizing data based on the types of procedure, medical records of patients having cardiovascular surgeries may be organized together.

The healthcare database system 1220 can also manage data based on user access permissions/privacy settings. For example, the data marked as private by the patient may be segregated from the rest of the data. The healthcare database system 120 can also implement extra security features (such as, e.g., extra layers of password authentication, or requiring authentication by biometric information (e.g., iris or retinal security features)) in order to access the data that are marked as private.

Additionally or alternatively, the healthcare database system 1220 can manage the data based on time or location (e.g., based on location information obtained by GPS sensors in the wearable device). The location may be the place where the data is acquired, the position of the patient, etc. For example, the healthcare database system 1220 may include distributed data storage and the healthcare database system 1220 can store the data close to the geographical location of where the data is acquired. As an example, a patient may receive an X-ray in a hospital in southern California. The healthcare database 1220 can store the information associated with the X-ray in a data store in California even though the patient may live outside of California. The healthcare database system 1220 can also organize data based on location of the patient. In the X-ray example, assuming the patient lives in New York, the healthcare database system 1220 may store the data associated with the X-ray at a data store close to New York rather than at a data store in California.

The action items associated with data may include whether any follow-ups are needed, where and who will perform the follow-up, what types of follow-ups are needed, etc. The action items associated with data may additionally or alternatively include notifications (e.g., alerts, reminders, etc.) to the user relating to follow-ups, etc. For example, during a patient's visit of his primary care physician, the primary care physician may refer the patient to see a specialist. Accordingly, the action item of the patient's virtual medical record may include scheduling an exam with a specialist located in a certain hospital. The healthcare database system 1220 can group data based on the action items. For example, information of all patients requiring an imaging exam at a certain hospital may be compiled together by the healthcare database system 1220.

In some embodiments, the healthcare database system 1220 may include at least a portion of the data processing system 1236, the data management system 1234, the data security management system 1212, or the record update system 1214, etc. For example, the wearable device of a HCP may record a conversation between the HCP and a patient. The wearable device can communicate the recorded conversation to the healthcare database system 1220. The healthcare database system 1220 may use its data processing system to analyze the recorded conversation.

Example Processes for Interacting with a Healthcare Database

FIGS. 13A, 13B, 13C, and 13D illustrate example processes for interacting with a healthcare database system. The example processes in FIGS. 13A-13D may be performed by the healthcare database system 1220 shown in FIG. 12 or by a wearable device.

Figure 13A:
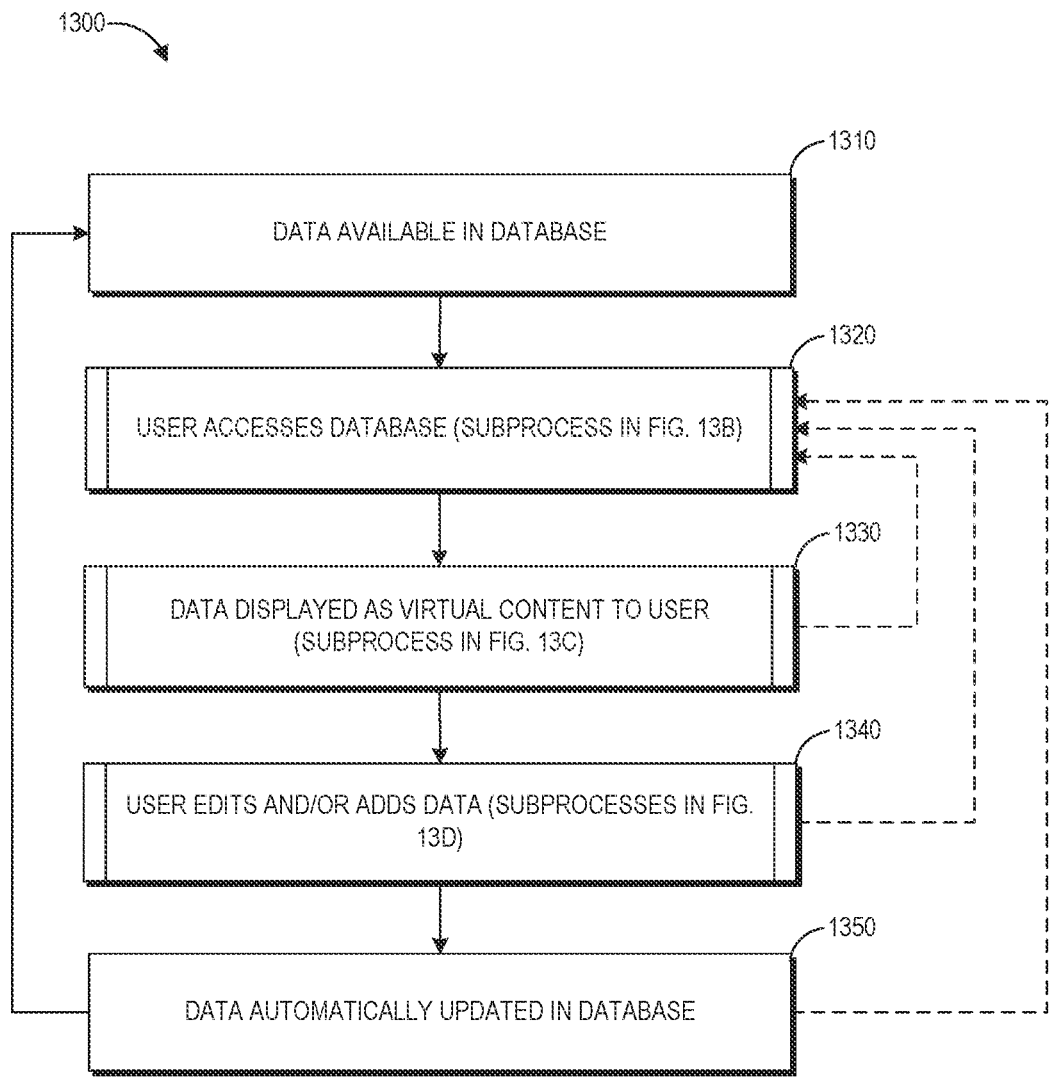
FIGS. 13A, 13B, 13C, and 13D illustrate example processes for interacting with a healthcare database system.

At block 1310 of the example process 1300 in FIG. 13A, the healthcare database system or the wearable device can manage medical related data, such as, e.g., controlling the storage of the medical related data in one or more data stores.

At block 1320, a user of an wearable device may want to access the data and send a request to the healthcare database system for accessing the data. The healthcare database system can receive a request to access the data from the wearable device. The healthcare database system can parse the wearable device's request and determine whether the request meets the required access privilege associated with the data. The access privileges may determine whether the user of the wearable device can edit, add, or view the data.

At block 1330, the wearable device can display virtual content. The wearable device can receive the request from the healthcare database system. The wearable device can display the requested data as virtual content in the 3D user interface of the wearable device. In some embodiments, the wearable device may have permissions to view only a portion of the data. As a result, the wearable device may present only the portion of the data which it has the permission on the 3D user interface.

At block 1340, the user of the wearable device can edit data in the healthcare database system or add data to the healthcare database system. In some embodiments, the wearable device may communicate with the health database system to verify whether the user has required access privileges before permitting the users to perform the operations in block 1340. In some implementations, if the user does not have editing access privileges for the data, blocks 1340 and 1350 are optional and may be skipped by the method.

At block 1350, the healthcare database system can automatically update its data. For example, wearable device can send an input received from a user. The input may include a new virtual medical record or an update to an existing virtual medical record. The healthcare database system can receive an input from the wearable device. The healthcare database can automatically initiate storage of the new virtual medical record or to update the exiting virtual medical record. Optionally, at blocks 1330, 1340, or 1350, the healthcare database system may return to the block 1320 to determine whether the user is still authorized to access the data. If authorized, the method continues with the subsequent blocks described above, but if not authorized, the method can terminate (e.g., the method can cease displaying the virtual content to the user).

Figure 13B:
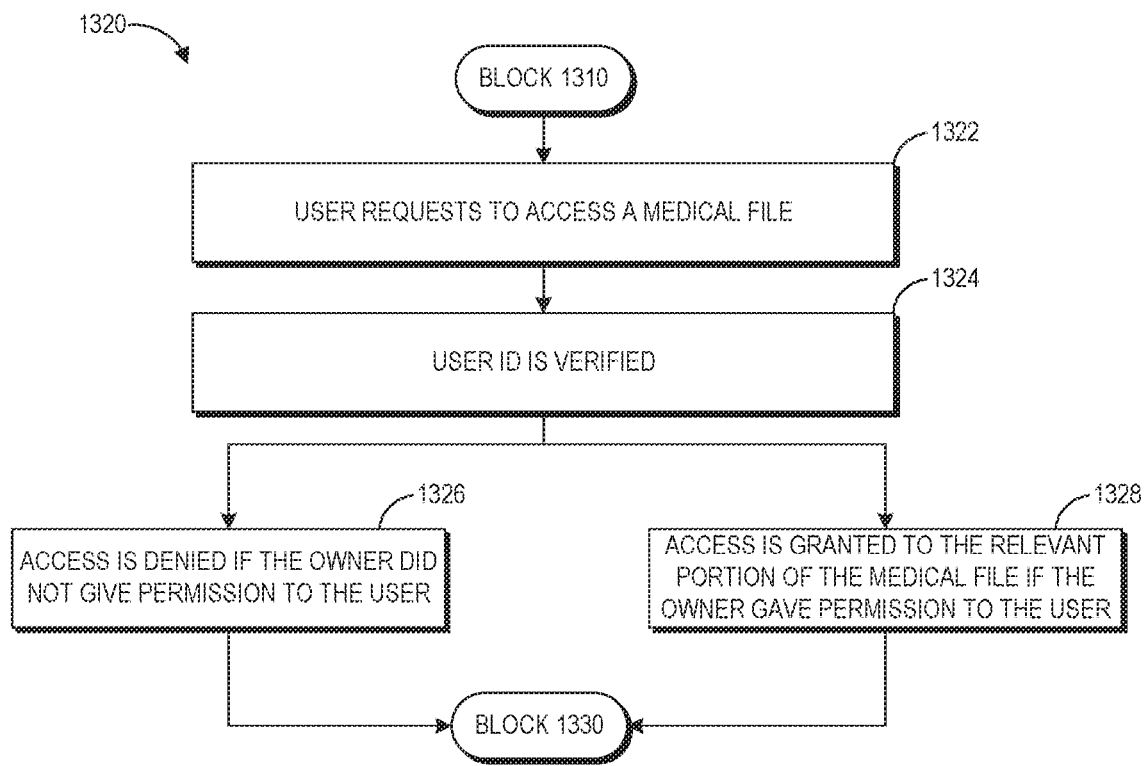

FIG. 13B illustrates an example subprocess for block 1320 in FIG. 13A. At block 1322, the user requests access to a medical file. The medical file may be stored in the medical data store of the healthcare database system. The user's wearable device may send a request for accessing the medical file to the user's healthcare database system.

At block 1324, the healthcare database system or the user's wearable device can verify the user's identity by techniques described with reference to FIG. 14A. As further described with reference to FIGS. 14A and 14B, the user's identity can be verified based on the user input (such as e.g., username and password) or the user's biometric information. In some embodiments, the healthcare database system or the wearable device can determine an owner or patient identifier (ID) associated with the requested medical file. The healthcare database system or wearable device can use the owner or patient ID to retrieve the access privileges associated with the medical file. As an example, a patient may set his medical records to be viewable by all hospitals. As another example, the patient may set his medical records to be viewable by any HCP in an emergency situation. Accordingly, if the user of the wearable device is a doctor in a hospital, the wearable device may grant access to the doctor.

At block 1326, the healthcare database system can deny the user's access if the owner of the medical file has not given the user access. The owner of the medical file may be the patient associated with the medical file. At block 1328, the healthcare database system can grant access to the relevant portion of the medical file if the owner has given the permission to the user. For example, although a nurse at a clinic may have access to all medical records of the patient, the wearable device of the nurse may only display the patient's name, address, and social security number for a nurse to book the next appointment for the patient because the nurse does not need other information such as the images from previous medical exams to book the appointment.

Figure 13C:
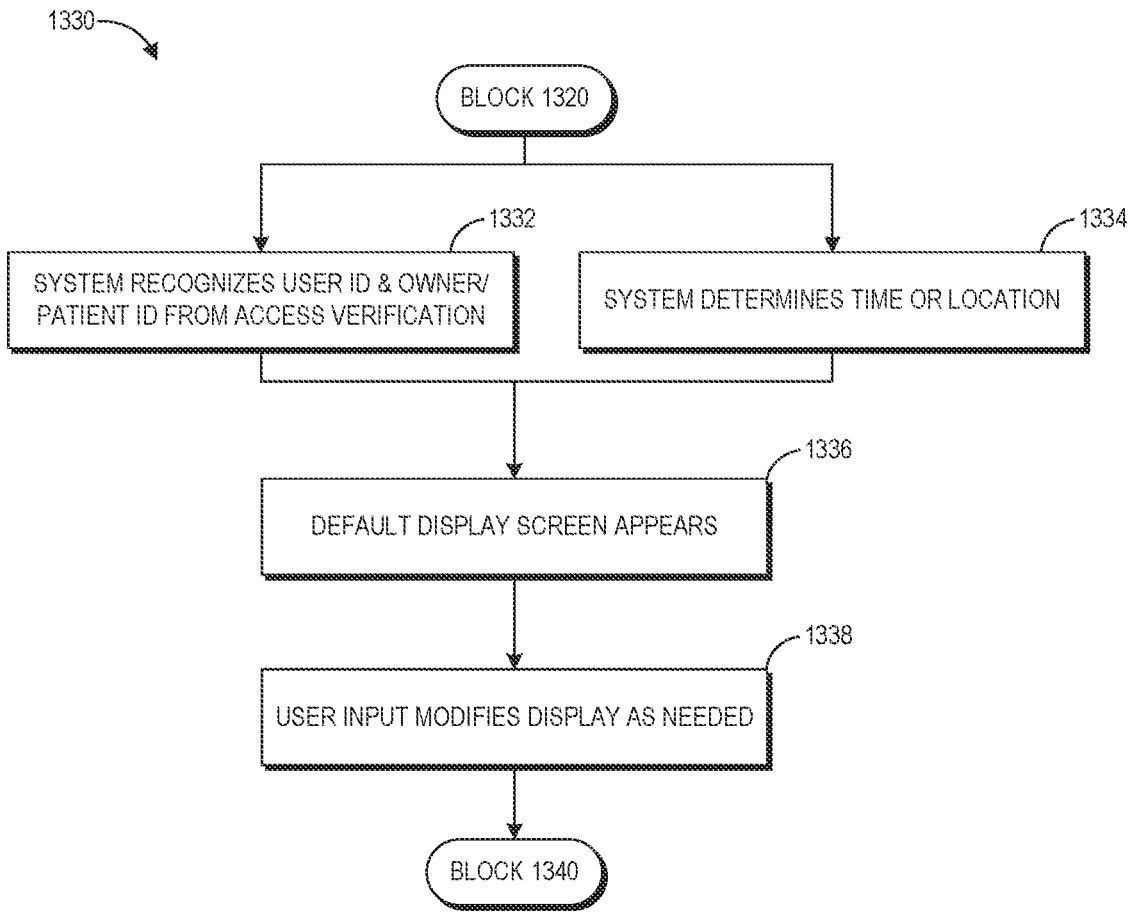

FIG. 13C illustrates an example subprocess for block 1330 in FIG. 13A. At block 1332, the wearable device can determine the user ID and the owner/patient ID from access verification (described with reference to the subprocess 1320 in FIG. 13B).

At block 1334, the system can determine the time or location. For example, the wearable device can use data from its environmental sensors to determine the current location of the user. Block 1334 can be performed in addition to or in alternative to block 1332.

At block 1336, a default display screen appears. The default display screen can present information associated with a user (such as, e.g., the user's scheduled appointments) or a patient of the user (such as, e.g., the patient's medical records). As further described with reference to FIGS. 21-24, the wearable device can present the display screen based on contextual information. For example, the wearable device can present the display screen based on medical file requested or based on the user's location. As an example, the wearable device can display medical images in different depth planes of the display system described in FIG. 2A. The most recent images may be presented at the depth plane that appear to be closest to the user while the earlier images may be presented at a depth plane farther away from the user.

At block 1338, the user can modify the display as needed. For example, the user can move the earlier images to a closer depth plane using poses or the user input device 466.

Figure 13D:
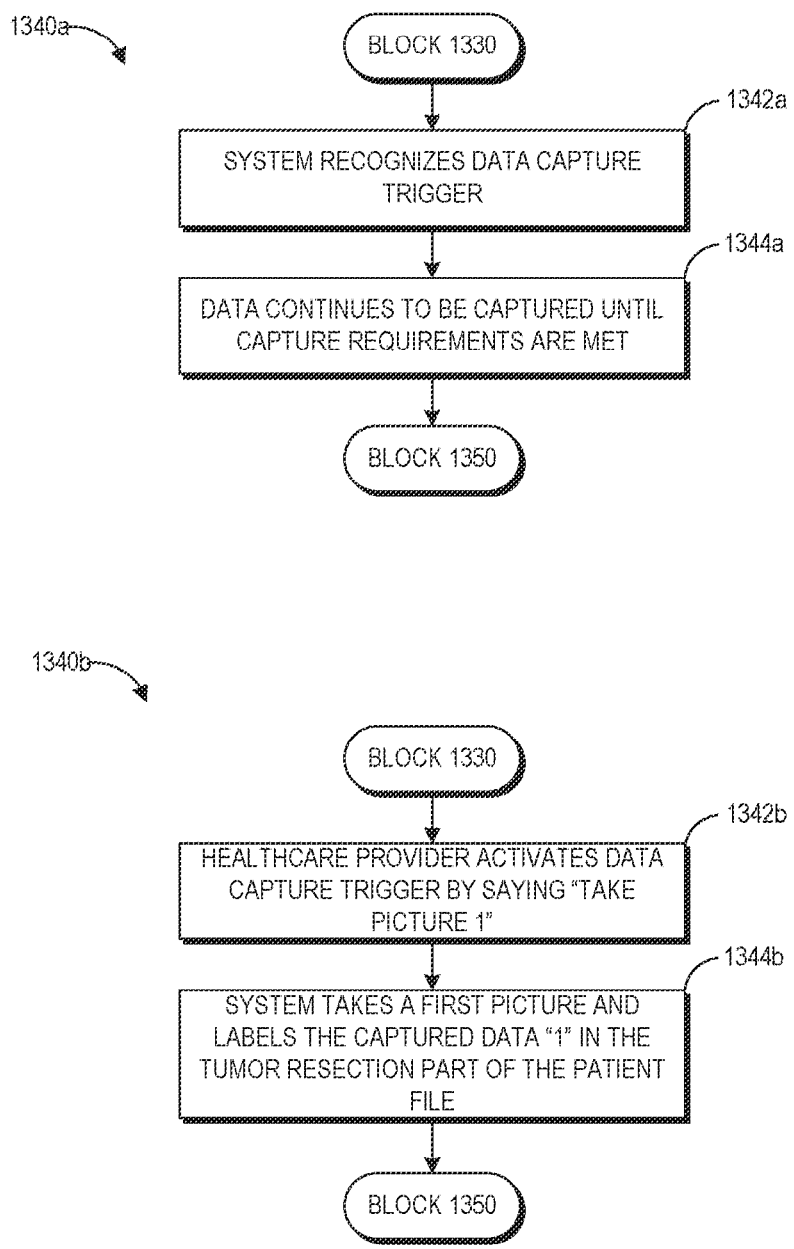

FIG. 13D illustrates example subprocesses 1340*a* and 1340*b* for block 1340 in FIG. 13A. The wearable device can monitor its environment using one or more environmental sensors. For example the wearable device's microphone may be continuously acquiring audio data in the environment while the user is wearing the wearable device.

At block 1342*a* of the subprocess 1340*a*, the wearable device can recognize a data capture trigger. As further described with reference to the initiation conditions in FIG. 15, the data capture trigger may be a keyword, a gesture, an object or an input from a user input device. The trigger can cause the wearable device to start capturing the data with one or more environmental sensors.

At block 1344*a*, the wearable device can continuously capture the data until capture requirements are met. Example capture requirements are described with reference to termination conditions in FIG. 16.

As another example of a subprocess for block 1340 in FIG. 13A, at block 1342*b*, the healthcare provider can activate a data capture trigger by saying, e.g., "take picture 1". In this example, the healthcare provider is the user of the wearable device and the trigger comprises the keyword "take picture 1."

At block 1344*b*, the wearable system (e.g., the healthcare provider's wearable device) can take a first picture based on the trigger. Since the trigger involves picture number 1, the wearable device can label the picture taken by the wearable device as number 1. In addition, because the picture includes a tumor of the patient, the wearable device can analyze the picture (using the object recognizers 708 for example) and identify the tumor in the picture. Accordingly, the wearable device can automatically send an instruction to the healthcare database system to place the picture in the tumor resection part of the patient's file. The wearable device may also send other information (e.g., the time when the picture was taken, the location where the picture was taken, the user who took the picture, etc.) to the healthcare database system. The data capture may be complete when the single image is taken.

Examples of Accessing a Virtual Medical Record Based on an Access Privilege

A virtual medical record can be associated with an access privilege. As described with reference to FIG. 12, the patient can set an access privilege for his medical related data using the data security management system 1232. The patient and a designated person with permission from the user can access and grant permissions to others for accessing all or a portion of the patient's virtual medical records.

Figure 14A:
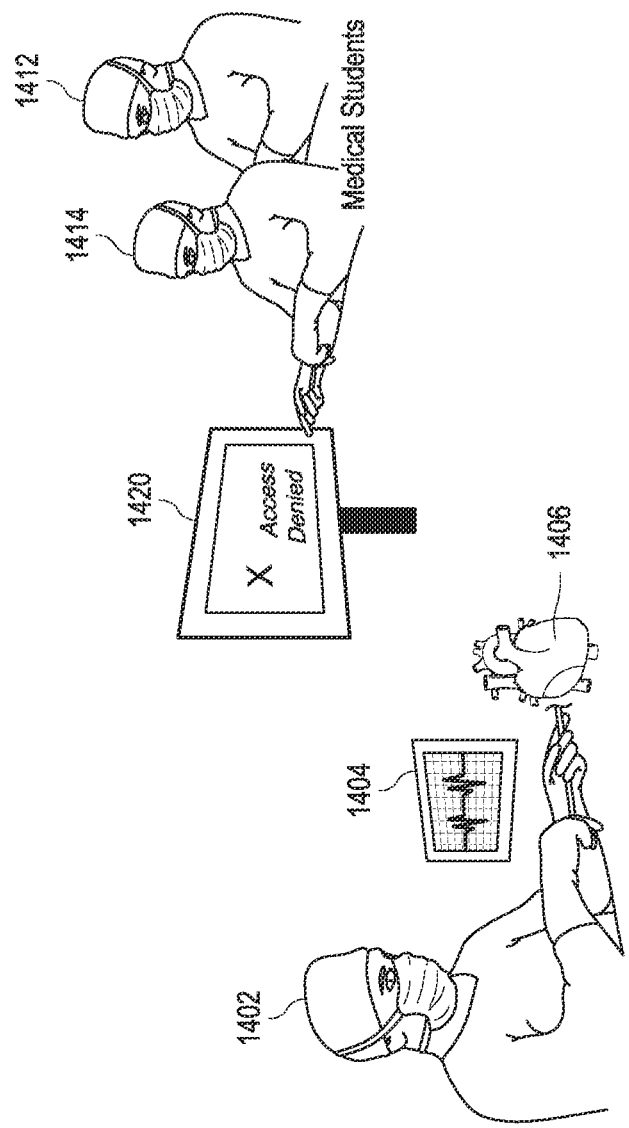
FIG. 14A illustrates an example of accessing a virtual medical record based on an access privilege associated with the virtual medical record.

FIG. 14A illustrates an example of accessing a virtual medical record based on an access privilege associated with the virtual medical record. In FIG. 14A, a surgeon 1402 is operating on a patient's heart 1406 in an operating room. While operating on the patient's heart, the surgeon 1402 can view the patient's physiological data acquired by environmental sensors. The surgeon 1402 can wear a wearable device and can view the patient's physiological data as summarized by the virtual element 1404 shown on the surgeon's wearable device's display.

The surgeon may have two medical students: the student 1412 and the student 1414. However, the students 1412 and 1414 do not have permissions to view the patient's physiological data. When the students try to access the patient's physiological data from a user device (see e.g., user device 1730 in FIG. 17 which may include the wearable device described herein), the user device may receive an indication that the physiological data cannot be viewed. Accordingly, the user device may provide the notification 1420 indicating that the students do not have the permission to access the physiological data. The notification 1420 can be stored in the patient's medical record. The surgeon's wearable device may also provide another notification to the surgeon that the students requested to access the patient's physiological data. In some embodiments, the wearable device of the surgeon or a student can provide a focus indicator near with the notification 1420. The focus indicator can comprise a halo, a color, a perceived size or depth change (e.g., causing a virtual object to appear closer and/or larger when selected), a change in a user interface element (e.g., changing the shape of a cursor from a circle to an escalation mark), a message (with text or graphics), or other audible, tactile, or visual effects which draw the user's attention.

The wearable device of a user requesting the patient's medical related data can verify the user's identity and determine the user's access privilege to a virtual medical record using a variety of techniques. The wearable device can also require its user to provide certain inputs for verification of the user's identity. The inputs may include a password, answers to security questions, etc. The wearable device can authenticate the user based on whether the inputs are correct. The wearable device can also verify a user's identity based on the user's biometric information. For example, wearable device may use face recognition, fingerprints, iris codes, eye colors, retina patterns, etc. to identify the user. The biometric information may also be used as the password associated with a user's account. Advantageously, in some embodiments, the biometric information provides a stronger form authentication and higher level of security for data accessing (than a password in the form of an alphanumeric string) because certain biometric features (such as, e.g., fingerprints, iris patterns, retina patterns) are unique to each person.

Once the user's identity is verified, the wearable device can determine whether user has access to a virtual medical record based on information associated with the user. For example, the user may be associated with an account identifier (ID). The wearable device can communicate with the healthcare database system 1220 to determine whether the account ID is within a list of approved account IDs associated with the patient's data. As another example, the wearable device can use the account ID to access characteristics of the user and determine whether the characteristics of the user satisfy the access criteria set by the patient. In some embodiments, the patient may be associated with a patient ID (also referred to as owner ID). The wearable device of the user can retrieve the access criteria or the list of approved account IDs by querying the healthcare database system 1220 using the patient ID.

As an example of presenting a virtual medical record based on a user's access privilege, the user's wearable device (such as, e.g., an optical sensor of the wearable device) can shine light into an eye of the user to perform retina recognition (also referred to herein as retinal scanning). The wearable device can identify a unique pattern associated the user's retina. The unique pattern may be used to determine the user's identity. For example, the retina pattern can be used as a password. The wearable device can determine whether the identified retina pattern matches the retina pattern associated with the user account ID seeking access to the virtual medical record. In certain implementations, the wearable device can verify a user's ID together with the healthcare database system 1220 (shown in FIG. 12). For example, the wearable device can take an image of the user's eyes. The healthcare database system 1220 can perform retina scanning and authenticate the user's identity based on a retina pattern identified from the retina scanning. In some embodiments, when the user's identity is verified, the user may share a virtual medical record with another user or receive a virtual medical record shared by the other user.

When the wearable device determines that the retina pattern of the user matches the user account ID seeking access to the virtual medical record, the wearable device can determine whether the user has access to the virtual medical record, which portion of the virtual medical record the user has access to, and whether the user can edit the virtual medical record. In addition, the wearable device can determine the user's access privileges of other healthcare related virtual contents, such as a hospital's appointment scheduling system, a status of a current surgery, information associated with medical equipment (e.g., whether the equipment is in use), etc. The wearable device can present to the user only the virtual content that the user has access to. Advantageously, in some embodiments, increased data privacy can be achieved by presenting the virtual content with a wearable device based on the user's level of access privilege. For example, visitors, such as medical sales representatives can be exposed to private patient information while at a clinic or hospital because the private information may be displayed on a computer monitor or be on papers. The wearable device can reduce the need to display information on the computer monitor or on papers by presenting the private information on the head-mounted display. The visitors may not be able to get access to private patient information previously on a paper or a computer monitor unless the visitors have the required level of access privilege. Some embodiments of the wearable device may analyze images of an iris of the wearer to determine an iris code (such as, e.g., the Daugman iris code described in U.S. Pat. No. 5,291,560) and perform account authorization and access to patient medical records, in addition to a retinal scan or as an alternative, using the iris code.

In some embodiments, if the user does not have access to the virtual medical record, the user may request another entity to grant permissions. The other entity may be the owner of the virtual medical record. For example, the user's wearable device can automatically send a request to the wearable device of the patient owning the virtual medical record asking the patient to grant access. The other entity may also include a user who can delegate access.

The level of access privileges associated with an entity may change based on the patient's interactions with the entity. For example, a front desk receptionist in a doctor's office may be in charge of scheduling patients. When a new patient visits the doctor's office, the front desk receptionist may initially have access to the new patient's basic information such as name and date of birth. After the new patient's first consultation with the doctor, the doctor can increase the receptionist's access privilege to allow the receptionist to view more information about the patient, such as, e.g., the patient's diagnosis, treatment, procedure information, etc. The doctor can update the receptionist's access privilege using the doctor's wearable device. For example, the doctor can use the user input device 466 or poses to add the account ID associated with the receptionist wearable device to the list of account IDs associated with a higher level of access privilege. As a result of the increased level of access privilege, the receptionist can obtain more information of the patient to appropriately schedule the patient's next visit. For example, the receptionist can determine the duration and the type of the next appointment based on the doctor's diagnosis. The receptionist can accordingly reserve the appropriate exam room and book the correct time slot for the next appointment. Although the examples of verifying the user's identity and determining the user's access privileges are described with reference to the wearable device of the user, in some embodiments, the healthcare database system 1220 alone or in combination with another user device can also perform the verification and determine the access levels in addition to or in alternative to the wearable device.

Figure 14B:
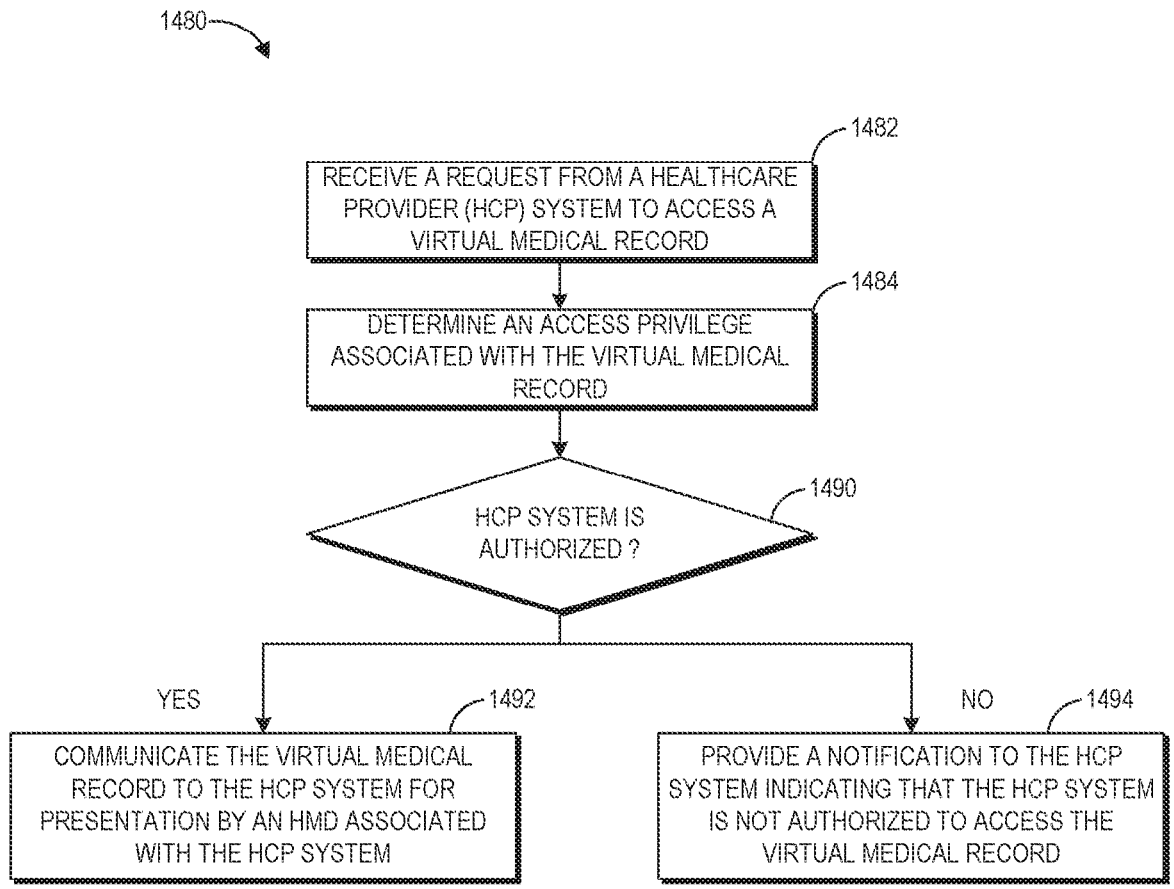
FIG. 14B illustrates a flowchart that shows an example process for accessing a virtual medical record based on an access privilege.

Example Processes of Accessing a Virtual Medical Record Based on an Access Privilege FIG. 14B illustrates a flowchart that shows an example process 1480 for accessing a virtual medical record based on an access privilege. The process 1480 may be performed by the healthcare database system 1220 (shown in FIG. 12).

At block 1482, the healthcare database management system receives a request from an HCP system to access a virtual medical record. The virtual medical record may be owned by the patient associated with the virtual medical record. The virtual medical record may be stored in the medical data store 1222.

At block 1484, the healthcare database management system determines an access privilege associated with the virtual medical record. For example, the healthcare database management system can access the medical data store 1222 to identify the access privilege. In some embodiments, the healthcare database management system 1222 can identify the characteristics of the virtual medical record and determine which level of access privilege should be attached to the virtual medical record based on the access criteria (described in FIG. 12) provided by the user.

At block 1490, the healthcare database system can determine whether the HCP system is authorized to access the virtual medical record. For example, the healthcare database system can verify the identity of the HCP and determine whether the HCP has the access privilege required for retrieving the virtual medical record.

If the HCP system is authorized to access the virtual medical record, at block 1492, the healthcare database system communicates the virtual medial record to a wearable device associated with the HCP for presentation. In some embodiments, the HCP is authorized to access only a portion of the virtual medical record, the healthcare database system may return the portion of the virtual medical record that the HCP system has permissions to access.

If the HCP system is not authorized to access the virtual medical record, at block 1494, the healthcare database system can provide a notification (such as, e.g., the notification 1420 shown in FIG. 14A) indicating that the HCP system is not authorized to access the virtual medical record. In some embodiments, although the HCP system can view the virtual medical record, but the HCP system may not be able to edit the virtual medical record. Accordingly, if the HCP system attempts to modify the virtual medical record, the healthcare database system can also provide a notification to the HCP system indicating that the HCP system is not authorized to modify the virtual medical record. In some embodiments, the healthcare database system can make a note in the medical record that the HCP system has viewed or updated the virtual medical record. The note may also include information regarding where, when, or for how long the HCP system has viewed the virtual medical record. The note may also include the portions that the HCP system has viewed or updated in the virtual medical record. Such notes may be stored in an access log in the medical record or in another database. The access log may have limited edit access privileges so that an unauthorized user cannot edit a patient medical record and then edit the access log to remove any trace of the unauthorized access to cover his tracks.

Examples of Documenting an Interaction Between a Patient and a Healthcare Provider Multiple entities are often involved in a patient's visit of an HCP. For example, during a patient's visit to a clinic, a patient may first fill out an intake form. The nurse may input the patient information into a computer system based on the intake form and retrieve additional information associated with the patient, such as, e.g., the patient's allergies, information of the patient's previous clinic visits, other medical information, etc. The doctor may see the patient and take notes based on the conversations and exams performed on the patient. However, the information obtained by the HCPs may not be complete. For example, the doctor's notes may miss a portion of the conversation with the patient. In addition, there are often delays between when a patient visits a clinic and when the patient's medical record is updated to reflect the information obtained during the patient's visit. The delay may be because the medical record needs to be updated by multiple entities and some entities may only communicate the updates periodically.

To address these problems, a wearable device can be configured to document an interaction between a patient and an HCP, process information acquired during the interaction, and automatically update the patient's medical record in substantially real-time as the patient is interacting with the HCP. The interaction between the patient and the HCP may include a conversation between the patient and the HCP, an exam or operation performed on the patient, information provided by the patient to the HCP (such as, e.g., medical histories), information provided by the HCP to the patient (such as, e.g., a diagnosis), etc., in combination or the like. The wearable device can update the patient's virtual medical records based on information obtained during the interaction between the patient and the HCP. For example, the wearable device can add medical images in an exam, a patient's symptoms (as extracted based on the conversation between the patient and the doctor), or a doctor's notes and diagnosis, etc., to the patient's medical record.

Examples of Recording and Processing an Interaction Between a Patient and an HCP The wearable device can use one or more environmental sensors (described with reference to FIGS. 2A and 2B) to record data of an interaction between a patient and an HCP. Data of the interaction may include audio and visual data.

The wearable device can process the recorded data (such as, e.g., using the local processing module 260, the remote processing module 270, the data processing system 1236) to extract relevant information. The wearable device can use a dictation program (which may implement the various speech recognition techniques described with reference to FIG. 12) to identify words spoken by the patient or the HCP in the recorded conversation. The wearable device can also use one or more object recognizers 708 to identify an object or a person involved in the interaction. For example, the wearable device may automatically detect the patient's face using a facial recognition algorithm. As another example, the wearable device can detect a portion of the user's body (such as a limb with which the patient is experience problems) using a computer vision algorithm. As yet another example, the wearable device can use text recognition techniques to extract texts in the images acquired by the outward-facing imaging system 464.

The wearable device can identify a portion of the record data as the relevant portion. For example, the recorded data may include the entire conversation between the patient and the doctor during a patient's visit. However, the beginning of the conversation may involve exchanges of pleasantries, which is not relevant to diagnosing the patient's disease. The wearable device may be configured to identify which portion of the conversation is not relevant to the descriptions of symptoms or medical information. The wearable device can use various machine learning algorithms to determine which portion is relevant (or irrelevant). For example, the wearable device can apply a machine learning model which is trained to identify certain keywords in the audio data or word descriptions. As another example, the wearable device can apply a computer vision algorithm to identify a portion of an image which includes a relevant object (such as the portion of the patient's body that has a lump). The wearable device can also use the various machine learning algorithms to identify a symptom of the patient (e.g., via the patient's speech or form images of the patient/environment as captured by the outward-facing imaging system 464 of the wearable device). The wearable device can provide a notification regarding the identified symptom to the user. For example, if the user does not notice that the patient winces from pain as the user performs a physical exam on the patient's left leg during the exam (e.g., there is no conversation between the user and the patient mentioning the pain on the patient's left leg), the wearable device can make a note in the medical file or provide a notification (e.g., a visual alert) that there might be tenderness on the patient's left leg.

In certain implementations, the wearable device may be configured not to process the irrelevant portion. For example, the wearable device can identify a portion of the audio data that involves a discussion of the weather. The wearable device may choose not to apply the speech recognition to this portion of audio data. As another example, after the wearable device has transcribed the audio data, the wearable device may mark the portion of the descriptions involving the patient's symptoms as the relevant portion. Based on the transcription, the wearable device can apply a machine learning model to the relevant portion to identify key points in the descriptions of the patient's symptoms. However, the wearable device may be configured not to apply the machine learning model to the discussion of weather.

Figure 15:
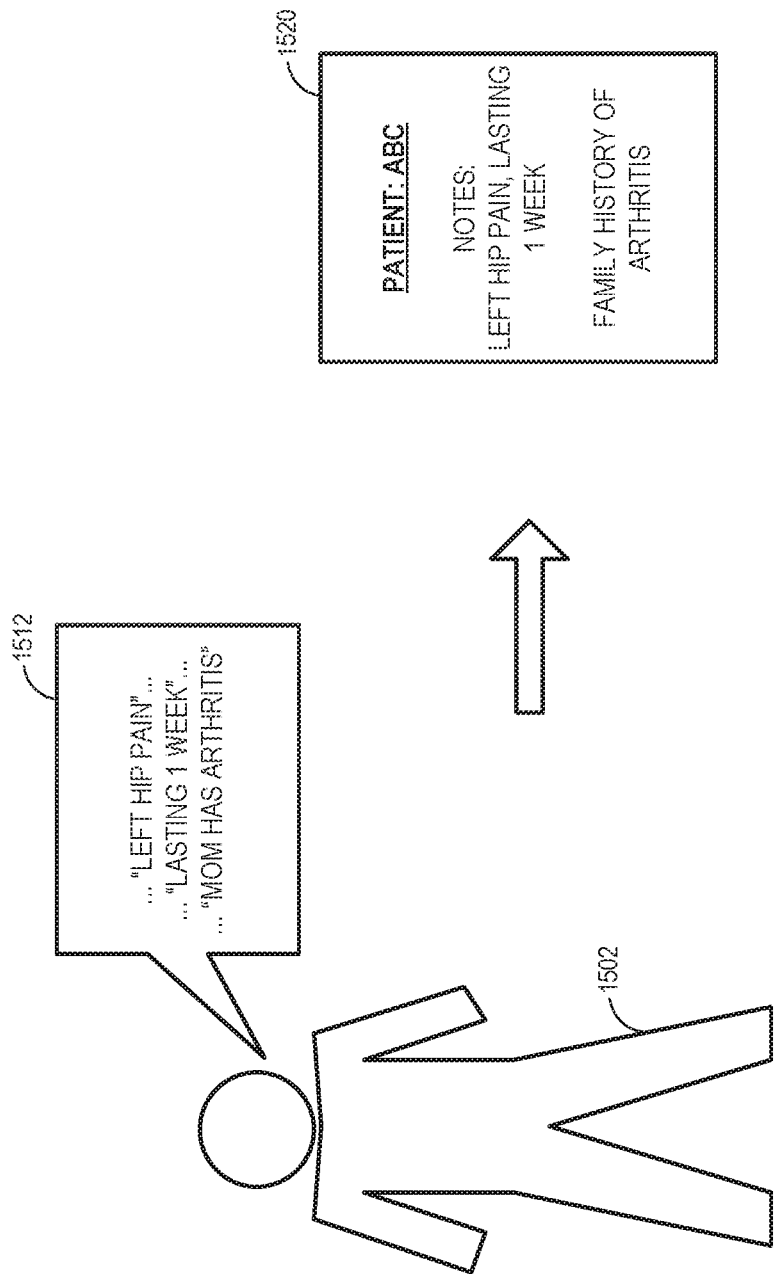
FIG. 15 illustrates an example of recording and processing audio data associated with an interaction between a patient and a healthcare provider.

FIG. 15 illustrates an example of recording and processing audio data associated with an interaction between a patient 1502 and an HCP. The HCP may be a doctor who may wear a wearable device. The wearable device can execute a dictation program in the background. The dictation program may be an embodiment of the data processing system 1236 described in FIG. 12. The dictation program can receive audio data from the microphone 232 of the wearable device. In some implementations, the dictation program can monitor the content of the audio data but only record a portion of the conversation between the patient and the HCP. In other embodiments, the dictation program records the entire conversation. The wearable device can record (e.g., via outward-facing imaging system 464 alone or in combination with the microphone 232) a portion of the interaction between the patient and the HCP. The wearable device can use various techniques to determine which portion of the interaction should be recorded. For example, the wearable device can start recording in response to a determination that an initiation condition is present and stop recording when a termination condition is present. Additionally or alternatively, the wearable device may process images of the patient taken during the procedure (e.g., by the outward-facing imaging system). The images (or the analysis of the images) can be stored in the patient medical record, which can provide for a more inclusive and accurate record of the procedure. For example, the wearable device may analyze the images showing a patient's broken limb (e.g., to determine an angle of the break) or the color of the patient's skin (e.g., to determine presence of a rash or overheating).

Examples of Initiation Conditions and Termination Conditions

The initiation condition and the termination condition may include a keyword, an input from a user input device 466, or a pose (such as, e.g., a head pose, a hand gesture, or another body pose). In some embodiments, the keyword, or the pose may be referred to as activation command. As an example, the keyword may include: "sick," "pain," "hurts," diabetes," "cancer," "stop," "start," etc. The keyword may include default keywords that are pre-programmed into the wearable device, words designated by the user of the wearable device, words identified using a machine learning algorithm, alone or in combination.

The wearable device can detect keywords and apply voice or speech recognition techniques to identify the presence of an initiation condition. An HCP may designate an initiation condition to be certain keywords said by a specific user. For example, a doctor may designate the phrase "start documenting" said by doctor himself as the initiation condition. Accordingly, the doctor's wearable device can start recording the audio data received on the microphone (optionally accompanied by a visual recording obtained by the outward-facing camera) if the wearable device detects that the doctor (and not the nurse) says "start documenting." Likewise, the doctor's wearable device can stop recording the audio (or visual) when the wearable device detects a phrase such as "stop documenting."

In some embodiments, the wearable device can provide context associated with the detected keywords. For example, the local processing and data module 260 of the wearable device may include a buffer. As the wearable device monitors the user's environment, the audio/visual data of the interaction may be temporarily stored in the buffer. Once the wearable device detects the presence of the initiation/termination condition, the wearable device can retrieve (e.g., from the buffer) and analyze the audio/visual data before/after the activation command to provide context for the keyword. As another example, when the wearable device detects the presence of the activation command, the wearable device may initiate storage of a portion of the audio/visual data before and after the activation command. For example, the wearable device can record (or initiate storage) a conversation 2 minutes before the activation command or 5 minutes after the activation command. The recorded conversation may be processed and stored for an HCP's later view. Advantageously, in some embodiments, by recording the audio/visual data before and after the initiation commend, the wearable device can provide the context of the keywords. The HCP can later edit the text if needed, but the context may help the HCP remember what was said by the patient. In addition, to save hardware storage space, the wearable device can later erase or overwrite the audio/visual data that is acquired more than 2 minutes before the activation command or more than 5 minutes after the activation command, for example.

Additionally or alternatively, the doctor's wearable device can record an entire conversation between the doctor and the patient in the wearable device's memory. Once the wearable device detects an initiation condition or termination condition, the wearable device can retrieve and present a context, including some of the conversation before and after the initiation condition or termination condition, to the doctor. The doctor can review or edit the context and determine whether the context should be documented by the wearable device.

In addition to or in alternative to keywords, the presence of an initiation condition or a termination condition may also be detected based on an input from a user input device (see e.g., user input device 466). An HCP can actuate a user input device using a variety of ways, such as, e.g., clicking on a mouse, tapping on a touch pad, swiping on a touch screen, hovering over or touching a capacitive button, pressing a key on a keyboard or a game controller (e.g., a 5-way d-pad), pointing a joystick, wand, or totem toward the object, pressing a button on a remote control, or other interactions with the user input device, etc. As an example, the HCP can use a totem to turn the dictation program on or off. When the wearable device detects that the HCP has pressed a certain button on the totem, the wearable device may start executing the dictation program. When the wearable device later detects that the same button is pressed again, the wearable device my stop the dictation program.

The wearable device can also detect a pose of the HCP to determine whether an initiation condition or a termination condition is present. The wearable device can use data acquired by its environmental sensors to detect the pose of the HCP. For example, the wearable device can use IMUs to determine whether the user's head pose has changed. The wearable device can also apply a computer vision algorithm to the images acquired by the outward-facing imaging system to detect a user's hand gestures. The wearable device can match a detected hand gesture with the gesture associated with the initiation/termination condition. The gesture associated with the initiation/termination condition may be set by the HCP. For example, the healthcare provider may designate "tapping a finger on the left hand" as an initiation condition of recording audio data and "tapping a finger on the right hand" as a termination condition of recording the audio data. The wearable device of the HCP may run the dictation program in the background when the patient is speaking to the HCP. The wearable device may detect, based on the image acquired by the outward-facing imaging system, that the HCP has tapped his right index finger on his left hand. Because this hand gesture is associated with the initiation condition, the wearable device may start recording the audio data using the dictation program as the patient and the HCP converse. When the wearable device detects that the HCP taps one of the fingers of his left hand on his right hand, the wearable device may stop recording the audio data although the dictation program may still be running in the background.

Some patients may feel uncomfortable when someone records the patient's conversation or obviously images the patient. Advantageously, in some embodiments, the initiation condition and the termination condition may be discreet so that the patient will not notice that he is being recorded or imaged. For example, the keywords for the initiation condition may be the phrase "have pain" instead of the phrase "start recording". As another example, the gesture associated with the initiation condition may be tapping a finger twice on the table rather than waving the HCP's arm in front of the HCP's wearable device.

Examples of Recording and Processing Audio Data

As illustrated in FIG. 15, the patient ABC 1502 describes his medical situation 1512 to an HCP (not shown in FIG. 15). The medical situation 1512 may include the patient's symptoms, how long the patient had the symptoms, personal medical history, family medical history, etc. In this example, the patient's symptoms involve left hip pain which has been lasting for a week. In addition, the patient tells the HCP that his mom has arthritis. The dictation program can transcribe the patient's description as the patient speaks. The wearable device of the HCP can generate the virtual item 1520 which summarizes the relevant portions of the patient's description. In some embodiments, the wearable device may use one or more environmental sensors or may communicate with another computing system to acquire additional information that was not provided by the patient's description. For example, the wearable device can apply a facial recognition algorithm to detect the patient's face in the image acquired by the outward-facing imaging system to determine the identity of the patient. The wearable device can use the detected face to query the healthcare database system 1220. If the patient's information is in the healthcare database system 1220, the healthcare database system 1220 can return the patient's name or other information to the wearable device. In this example, the patient's name is ABC. The wearable device can incorporate the information retrieved from the healthcare database system 1220 into the virtual item 1520. In this example, the patient's name is added to the virtual item 1520. In some cases, the patient may wear a wearable device during the examination, and patient information acquired by user sensors on the patient's wearable device may be communicated to the HCP's wearable device or stored in the patient medical record. For example, eye-tracking cameras can determine information about the user's eyes, and physiological sensors on the wearable device can determine information about, e.g., the patient's heart rate, respiration rate, blood pressure, etc.

The virtual item 1520 can be displayed by the wearable device of the HCP. In some situations, the patient 1502 also wears a wearable device. The virtual item 1520 may also be displayed by the patient's wearable device.

The recorded or processed data may be added to the patient's medical records. The wearable device can verify the patient's identity using various identity verification techniques described with reference to FIGS. 12-14B before adding the data to the patient's medical records.

Although the wearable device of the HCP documents the interaction between the patient and the HCP, the wearable device of the patient can also document the interactions alone or in combination with the wearable device of the HCP. For example, patient can dictate his medical situations using a dictation program on his wearable device.

In addition, although this example uses a dictation program, other input technique for documenting the interaction may also be used. For example, the HCP may document the interactions by typing the patient's descriptions using a virtual or physical keyboard of the wearable device. The HCP can also document the interactions by imaging the interactions using the outward-facing imaging system of the HCP's wearable device.

Examples of Recording and Processing Imaging Data

The wearable device of an HCP can obtain an image of the patient using one or more environmental sensors. For example, the wearable device can take a picture or videotape the patient using the outward-facing imaging system 464. Advantageously, in some embodiments, the wearable device can provide a hands-free way of recording and thereby minimize sterility issues. For example, the wearable device can use data acquired by one or more environmental sensors to determine whether the user of the wearable device has entered into an operating room. The wearable device may make the determinations using object recognizers 708 to identify items that are typically present in the operating room or identify a sign which states "operating room". In response to a determination that the user is in the operating room, wearable device can record audio/visual data of a procedure occurring in the operating room. Additionally or alternatively, the wearable device can take pictures or videotape the user's surroundings every few seconds until a termination condition is detected.

As another example, the wearable device of the HCP can start recording images of the patient or a medical procedure on the patient in response to a gesture or a keyword spoken by the HCP. For example, the wearable device may start recording a portion of the procedure upon detection of the phrase "start recording" and stop recording upon detection of the phrase "stop recording" spoken by the doctor. The doctor can also wave his right hand three times in front of the wearable device as an activation command for taking an image of the patient.

By using poses, voice commands, or object recognizers, the wearable device can help an HCP avoid contacting unsterile devices (such as, e.g., personal devices, camera, or smartphones) in a medical procedure/exam. In addition, the wearable device can automatically update the patient's virtual medical records (such as, e.g., patient charts) based on the recorded audio/visual data, and thereby reduce the need to upload data from personal devices or digital microscope, etc. in traditional techniques.

Examples of Automatically Updating Virtual Medical Records with Recorded Data

Currently, medical images of a patient are managed and stored by the hospital's picture archiving and communication system (PACS). To add new medical images of the patient, an HCP needs to email the new images to the hospital's PACS system. However, this technique of updating the patient's record may be unreliable because images may be accidentally attached to a wrong person or may be lost in an email.

The wearable device described herein can provide a faster and more accurate way for updating the patient's medical record (such as, e.g., the patient chart). The wearable device can identify a patient's file that may need to be updated. For example, the wearable device can receive a selection of the patient's file by an HCP (such as, e.g., a doctor). The wearable device can also identify the patient using facial recognition, voice recognition, or other biometric information of the patient. Advantageously, by using the various identity verification techniques described herein, the wearable device can reduce the likelihood that a patient's data is accidentally attached to another patient's file.

Once the wearable device identifies the patient, the wearable device can open the patient's file for updates. Accordingly the patient's file becomes accessible to the HCP while the patient is interacting with the HCP. As the HCP is capturing audio/visual data associated with the patient, these data may be attached to the patient's file in near real-time. The wearable device of the HCP can communicate with a healthcare database management system to save the updates to the patient's file. Advantageously, in some embodiments, by automatically updating the patient's file while the patient is interacting with an HCP, the HCP does not have to email the images back and forth with the PACS (or another HCP); thereby reducing the likelihood that the images are lost. In addition, the update to the patient's file can occur during the patient's visit/interaction which can reduce the delays in updating the patients' records.

In certain implementations, when a patient's medical record is open for view or editing, multiple users of the wearable devices can collectively view and update the virtual medical records. As further described with reference to FIGS. 17-20, a first user of the wearable device can update the medical records while a second user of the wearable device can view the updated virtual medical records as the first user is updating the medical records. The wearable device can provide and store an indication of each user's interaction with a virtual medical record and who is accessing the virtual medical record (e.g., the access log described above). For example, the wearable device can show a first user's virtual avatar and the word "editing" near a set of images in the virtual medical records. The wearable device can also show a second user's name and the word 'viewing" near the set of images.

Figure 16:
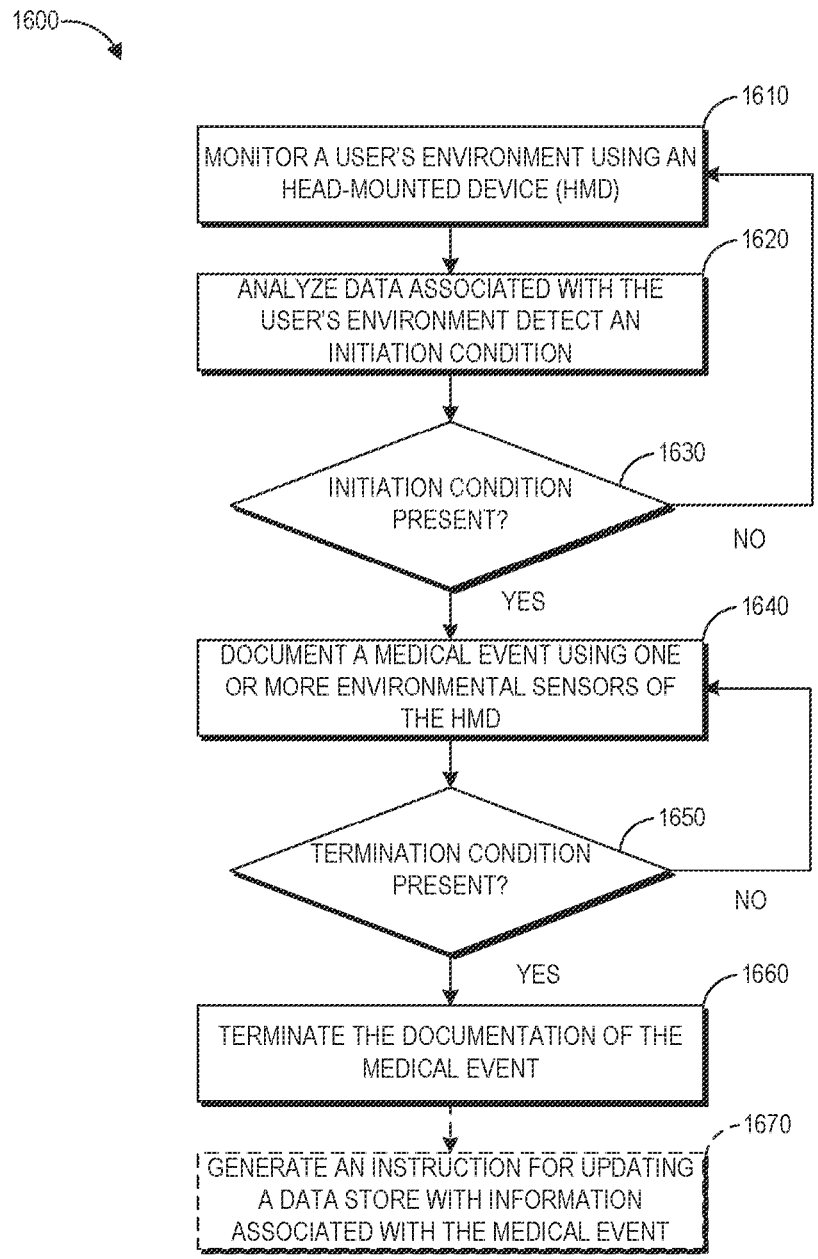
FIG. 16 is a flowchart that shows an example process for documenting a medical event by a healthcare provider (HCP).

Example Processes of Documenting an Interaction Between a Patient and a Healthcare Provider FIG. 16 is a flowchart that shows an example process 1600 for documenting a medical event by a wearable device. The medical event may include an interaction between an HCP and a patient, an exam or procedure performed on the patient, or a portion of the interaction/exam/procedure, etc. The process 1600 can be performed by a wearable device. The user of the wearable device may be the HCP or the patient.

At block 1610, the wearable device monitors the user's environment. The wearable device can monitor the user's environment using one or more environmental sensors described herein. For example, the wearable device can acquire the sound of the user's environment using the microphone and can acquire the images of the user's environment outward-facing imaging system. The data acquired by the environmental sensors may include data associated with the user or the user's physical environment.

At block 1620, the wearable device analyzes data associated with the user's environment to detect an initiation condition. The data associated with the user's environment may include data acquired by the one or more environmental sensors, data stored on the wearable device, data retrieved from the remote data repository 280, etc. For example, the wearable device may use a speech recognition algorithm to detect words acquired in the audio data. The wearable device can also access keywords associated with the initiation condition from the healthcare database system 1220. The wearable device can determine whether the audio data includes the keywords associated with the initiation condition.

At block 1630, the wearable device can determine whether the initiation condition is present based on the analysis of the data at block 1620. If an initiation condition is not present, the process 1600 goes back to the block 1610 where the wearable device continuously monitors the environment.

If an initiation condition is detected, at block 1640, the wearable device may document a medical event using one or more environment sensors. For example, the wearable device can use the microphone 232 to record a conversation between the patient and the HCP. The wearable device can also use the outward-facing imaging system 464 to take a picture of the patient. The wearable device can process the audio and visual data to identify relevant information.

At block 1650, the wearable device may determine whether a termination condition is present. The wearable device can detect the termination condition based on the data associated with the user's environment. If the termination condition is not present, the wearable device can continuously document the medical event as shown in block 1640. If the termination condition is present, at block 1660, the wearable device may terminate the documentation of the medical event. For example, the wearable device may stop processing data acquired by the one or more environmental sensors, turn off an environmental sensor, instruct an environmental sensor to enter sleep mode, etc.

Optionally at block 1670, the wearable device can generate an instruction for updating a data store with the information associated with the medical event. The information associated with the medical event may include audio or visual data documenting a portion of the medical event or the entire medical event. The instruction can cause a healthcare database system to add the information associated with the medical event to the patient's virtual medical records. In some embodiments, the wearable device can update the data store while the wearable device is document the medical events. Additionally or alternatively, the wearable device can update the data store after the wearable device finishes documenting the medical event.

Examples of Sharing Medical Information Among Healthcare Providers

Figure 17:
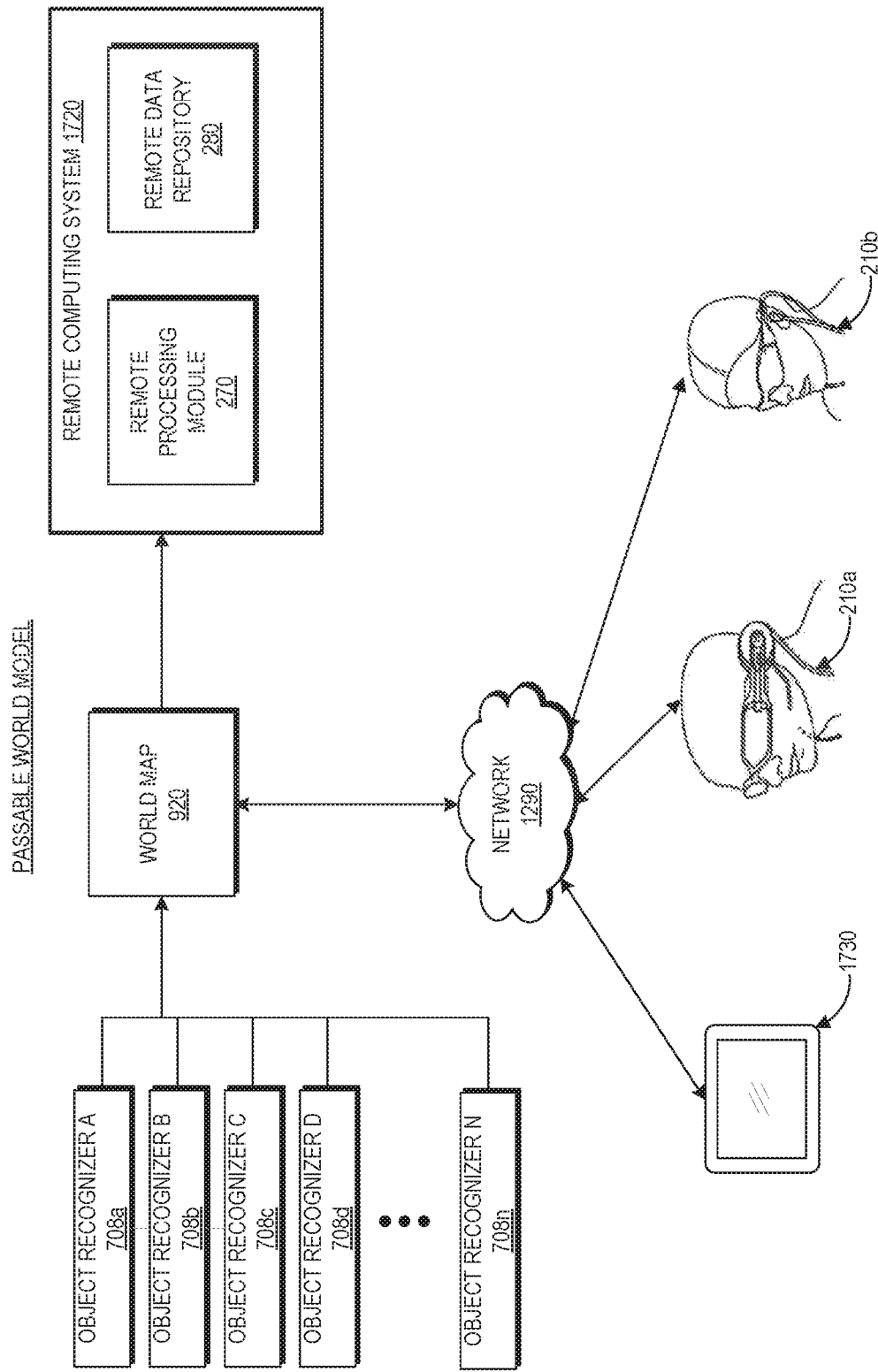
FIG. 17 schematically illustrates an overall system view depicting multiple devices interacting with each other.

FIG. 17 schematically illustrates an overall system view depicting multiple devices interacting with each other. The computing environment 1700 includes a user device 1730, and wearable devices 210a and 210b. The user device may be a wearable device (such as a wearable device), a computer, a mobile device, or any other devices alone or in combination.

The user device 1730 and the wearable devices 210a, 210b can communicate with each other through the network 1290 (shown in FIG. 12). In some embodiments, the user device 1730 and the wearable devices 210a, 210b can also communicate with another device (e.g., a medical device such as an ultrasound probe) that is connected with the wearable device via a wired or a wireless network. For example, an object recognizer 708 can analyze imagery captured by the wearable device and determine that a medical device (e.g., an ultrasound probe) is present. The wearable device may attempt to connect to the medical device (e.g., by listening for advertising events broadcast by the medical device) to imitate a communication link between the device and the wearable device. The computing environment 1700 can also include one or more remote computing systems 1720. The remote computing system 1720 may include server computer systems that are clustered and located at different geographic locations. In some implementations, the remote computing system 1720 may include an embodiment of the healthcare database system 1220 shown in FIG. 12. The computing device 1730 and the wearable devices 210a, 210b can communicate with the remote computing system 1720 via the network 1290.

The remote computing system 1720 can include the remote data repository 280 (also shown in FIG. 2) which can maintain information about physical and/or virtual worlds. The remote computing system 270 can also include a remote processing module 270 (also shown in FIG. 2). The remote processing module 270 can include one or more processors which can communicate with the user device 1730, the wearable devices 210a and 210b, and the remote data repository 280. In some implementations, at least a portion of the processing or storage can be provided by the local processing and data module 260 (as shown in FIG. 2).

The users of the wearable devices 210a, 210b and the user device 1730 can share information of an environment and interact with virtual and physical objects in the environment via the network. For example, a doctor may wear the wearable device 210a and perform a surgery on a patient in an operating room. The wearable device 210a can generate and display a virtual content screen to the doctor. The virtual content screen may include a first portion of the virtual content that only the doctor can view. The virtual content screen may also include a second portion of virtual content that other users in the room can view. The doctor may share some parts of the first portion or the entire first portion of the virtual content with other users. The wearable device 210a can image the patient and the doctor's surroundings using an outward-facing imaging system. The image acquired by the physician may be communicated to a medical student wearing the wearable device 210b outside of the operating room. In some embodiments, the medical student's wearable device 210b may receive the world map 920 associated with the operating room. The world map 920 may include virtual and physical objects in the operating room. For example, the medical student can perceive, via the 210b, the patient's virtual medical records and medical equipment in the operating room. In some situations, the user of the wearable device 210b and the user of the wearable device 210a can interact with virtual or physical objects in the world map 920. For example, both the doctor and the medical student (albeit in different locations) can examine a patient at the same time during the patient's visit to a clinic. Also, the examination conducted by the doctor can be documented in the patient's medical record. The record of the examination can be reviewed later by the user or another authorized user (e.g., as a case study for medical education).

The information of the world map 920 may be developed over time and may be based on the information collected by different user devices. In some embodiments, the world map may also be referred to herein as the world model. Models of virtual worlds may also be developed over time and be based on the inputs of different users. As described with reference to FIGS. 7 and 9, information acquired by the user devices may be used to construct a world map 920. Various object recognizers (e.g., 708a, 708b, 708c . . . 708n) may be used to recognize objects and tag images, as well as to attach semantic information to the objects. Additionally, the wearable devices 210a, 210b can identify and communicate with a medical device (e.g., an ultrasound probe) that is connected with the wearable devices 210a, 210b via a wired or a wireless network. These object recognizers may include the object recognizers 708a and 708n shown in FIG. 7.

The wearable device and the remote computing system 1720 can construct, update, and build a collection of images, points and other information using the information obtained from one or more wearable devices. For example, the wearable device may process raw information acquired and send the processed information to the remote computing system 1720 for further processing. The wearable device may also send the raw information to the remote computing system 1720 for processing. The wearable device may receive the processed information from the remote computing system 1720 and provide final processing before projecting to the user. The wearable device may also process the information obtained and pass the processed information to other wearable devices. The user device may communicate with the remote data repository 280 while processing acquired information. Multiple wearable devices and/or multiple server computer systems may participate in the construction and/or processing of acquired images.

The information on the physical worlds may be developed over time and may be based on the information collected by different user devices. Models of virtual worlds may also be developed over time and be based on the inputs of different users. Such information and models will sometimes be referred to herein as a world map or a world model. As described with reference to FIGS. 7 and 9, information acquired by the user devices may be used to construct a world map 920. Various object recognizers may be used to recognize objects and tag images, as well as to attach semantic information to the objects. These object recognizers may include the object recognizers 708a and 708n (also described in FIG. 7).

The remote data repository 280 can be used to store data and to facilitate the construction of the world map 920. A wearable device can constantly update information about the user's environment and receive information about the world map 920. The world map 920 may be created by the wearable device or in combination with another computing device. The remote wearable devices 210a, 210b, the user device 1730, and computing system 1720, alone or in combination, may construct and/or update the world map 920. For example, a wearable device may be in communication with the remote processing module 270 and the remote data repository 280. The wearable device may acquire and/or process information about the user and the user's environment. The remote processing module 270 may be in communication with the remote data repository 280 to process information about the user and the user's environment. The remote computing system 1720 can modify the information acquired by the wearable device 210a, such as, e.g., attaching access privileges a virtual object, enlarging a portion of the image acquired by the wearable device, extract relevant medical information from the image of the wearable device 210a, etc. The remote computing system 1720 can send the processed information to the wearable device 210a or another computing device.

Access Privileges

As described with reference to FIGS. 14A-17, to share medical information associated with the patient among users, the users can have access privilege to access the patient's medical record, or at least access privilege to access the medical information a first user is sharing with a second user. As described with reference to FIG. 12, the first wearable device can send a request to the second wearable device using the data sharing system 1238 to view the medical information. After the second wearable device receives the request from the first wearable device, the second wearable device may try to access the patient's medical record to access the medical information in the data store 1220. The patient system can also get a request from the first or second wearable device that the second user is trying to access the medical information. The patient system can then determine whether the second user has the access privilege to the medical information as described with reference to FIGS. 14A-14B. As described above, the access privileges can be specific to different portions of the patient medical record or for different users. For example, the patient may have read access to the full medical record but edit access to the patient and family history section. An HCP may have read access to the full medical record and edit access to the portion that is relevant to the HCP's specialty but not have edit access to portions specific to other HCP specialties (e.g., a cardiologist may have edit access to cardiac-related portions of the medical record but not to the patient's dental records).

Shared Medical Information

The medical information shared among users can be any interactions with a patient as described, for example, with reference to FIGS. 15-16. The medical information can include test results the user collects during a test on the patient or previously stored patient data or analysis (e.g., trends of the patient's health condition). In some embodiments, the first user can define what medical information he wants to share with the second user. For example, where the first user is seeing the patient, the first user can configure the access privileges of the second user such that only the image regarding the patient's left arm or other parts of the patient to the second user. The wearable device of the first user may share the observations by the first user (e.g., via images captured by the outward-facing imaging system) in real time to the wearable device of the second user.

Before the first wearable device of the first user shares medical information to the second wearable device, the first wearable device may prompt a notification to the first user asking whether the first user wants to edit the medical information being sent. The first wearable device can present to the first user showing the medical information to be shared. The first wearable device may give the first user options to modify the medical information, e.g., via poses or the user input device 466. The first user can also provide an indication to one or more other users with whom the first user wants to share the modified medical information. Based on the indication received from the first user's wearable device, the other users can accept the first user's "invitation" to share the medical information in the first user's environment.

In certain implementations, the first user can attach access privilege with the medical information. The first user can set some medical information as private so that the medical information will not be shared with other users. As one example, the first wearable device can observe (e.g., via the outward-facing imaging system) the patient's abdomen and the patient's face. The first wearable device can share the portion of the images related to the patient's abdomen to another physician to facilitate diagnosis of the illness. However, the first wearable device may be configured not to share the portion of the images having the patient's face to protect the patient's privacy. The access privilege associated with sharing medical information may be based on the viewer. For example, during a surgical procedure, content (virtual or physical) in the surgeon's field of view may be shared with everyone in the same operating room. However, only a subset of content may be shared with another user that is outside of the operating room. For example, physical content (e.g., as observed by the outward-facing imaging system) is shared with a student or a physician in the pathology lab, while the virtual content as seen by the surgeon is not shared with the student or the physician in the pathology lab.

Example Triggering Events for Sharing Medical Information

Wearable devices described herein can facilitate sharing medical information among multiple users. Using wearable devices in a healthcare environment can allow multiple users to access and view information for a medical procedure at the same time. By generating and displaying virtual content to users in real-time, wearable devices do not require users to walk around in the healthcare environment and view information on many pieces of equipment, such as monitors, displays, etc. The wearable devices can gather all the information into a centralized location and allow each user to view the same information or a modified version of the same information. For example, the users can view information about the patient's heart such as (heart rate or other statistics) via display 220 instead of finding such data from a medical device. The wearable device can further allow each user to manipulate or edit the information as needed. The updated information may automatically send to other users during a shared session.

As described with reference to FIG. 15, multiple users can view and update a patient's medical record if they have permissions. When a user is viewing a patient's medical record, the user may see the other users who are viewing the same patient record. The user can also see other information (e.g., file history) regarding the patient's medical record. For example, the user can see who has made updates in the patient's medical record. Accordingly, the users may get information about who else is "in" the patient's record.

A user can configure sharing of a virtual content screen which can be created based on information in the patient's record. The wearable device can display the virtual content screen within the user's field of view. The user can then edit or choose the information he wishes to view within the virtual content screen. The user can also configure which sections of the virtual content to share with other users. Additionally or alternatively, the user can also choose to replicate his field of view to other users. The other users can therefore perceive the virtual content screen alone or in combination with other virtual content in the field of view of the user.

The first wearable device can receive user instructions to share medical information with the second wearable device. The instructions can be provided upon detection of keywords, or may be provided via totem or gestures. For example, the first user may define the phrase "share medical information" as a trigger to cause his wearable device to share a virtual content screen (presented by the display 220) to the other user's wearable device. As another example, the trigger may be an actuation of a button or a hand gesture. When the first user pushes a button on a totem associated with the first wearable device or he taps his right thumb on his left hand, the wearable device can share a virtual content screen presented by the first wearable device to other users' wearable devices.

The second user's wearable device can generate a notification asking whether the second user wants to accept the first user's request to share the medical information or whether the second user would like to participate in a sharing session where the second user can share a virtual experience with the first user via their respective wearable devices. The second user's wearable device may present information shared by the first user in response to receiving the indication from the second user to participate in the sharing session.

In some embodiments, advantageously, the wearable device can analyze data that the environment sensors have collected and can determine a trigger for a sharing session based on the analysis of data gathered from the environment sensors. For example, the wearable device can determine whether there are other devices in the proximity (e.g., by using computer vision techniques to analyze acquired images or by communicating with the nearby devices). If nearby devices are discovered, the wearable device of a user may provide a notification to the user asking whether the user wants to share some medical information with the other devices.

The trigger for sharing information can also be based on interactions associated with a user. For example, the wearable device can analyze an interaction between the user of the wearable device and a patient. The wearable device can detect the presence of a trigger for a sharing session if the wearable device determines the interaction needs the participation of another user. For example, if the wearable device determines that the user is performing a surgery on the patient's liver and the user makes notes or comments that the disease on the liver might be cancerous, the wearable device may generate an alert displayed to the user asking whether he wants to share the image of the liver to another user (e.g., a physician in a pathology lab) who will analyze the tumor (described below with reference to FIG. 19). As another example, a wearable device can analyze data collected in previous interactions to determine whether a trigger for sharing information is present. For example, the wearable device of a physician can analyze data related to the patient's past visit and find that a specialist is recommended for diagnosing the patient's illness. The wearable device can accordingly share some of the patient's medical information with the specialist after the patient's visit. The wearable device of the physician can also share the information related to the patient (e.g., as perceived by the physician) during the patient's next visit so that both the physician and the specialist can diagnose the patient's illness.

In some embodiments, virtual content to be shared among multiple users can include patient parameters such as the patient's blood pressure, brain activity (e.g., the patient is awake), temperature, etc. The parameters may be collected by medical devices or the user's wearable device. The medical devices can communicate with the wearable device via a wired or wireless network, so that the wearable device can receive the patient parameters from the medical devices. The wearable device of a user can collect data and analyze from multiple external devices in proximity (e.g., a heart monitor, an anesthesia monitor, etc.) via internet, Bluetooth, wireless sharing capabilities. The wearable device can then present and display parameters from all the devices onto a centralized platform to the user. The wearable device can act as a centralized platform to display parameters from all the external devices connected (physically or wirelessly) with the patient. In some embodiments, as later described with reference to FIG. 23, the wearable device may determine the location of the user (e.g., by analyzing location data from GPS sensors). After analyzing the data the environmental sensors collect, the wearable device may provide a notification to the user asking whether he wants to share the medical information with one or more other users. For example, if the wearable device determines the user is in an operating room and there are other users in the operating room, the wearable device can provide an option to the user to share the medical information he perceives with other users in the same operating room. If the user allows all other users in the operating room to view his field of view, the wearable device of the other users may present virtual content screens comprising the user's field of view for a shared experience.

Timing of Sharing Medical Information

The sharing of medical information among users can occur shortly after the request to share or can be delayed until a later time. For example, the wearable device of a user may receive a request to share what he sees in his field of view in real time with the other users. In another example, the wearable device may receive a request of the user to share what he saw in his field of view for a period of time in the past (e.g., five minutes ago) to other users. The user may define specific time duration or a start/end time using his wearable device. In some embodiments, if multiple users are accessing the patient's medical record at the same time, the wearable devices for one or more of the users can generate notifications indicating that there is another user actively viewing the patient's medical record. The wearable system may provide an access lock on the medical record to prevent two (or more) users from editing the record at the same time, to provide for medical record integrity. In other situations, the wearable system can allow multiple users to edit a medical record at the same time, and the wearable system may synchronize the edits done by different users to maintain consistency.

Methods of Sharing Medical Information

The wearable device of a user can also configure how medical information will be shared with other users. For example, the user (who may be an HCP or a patient) may establish that he wants to email a specific part of the patient's medical record to the second user at a specific time (e.g., 12 AM on Friday, Jan. 6, 2017). The wearable device, at 12 AM on Friday, Jan. 6, 2017, can send the other users an email containing the specific part of the patient's medical record. The email may include any information the user wants to share with the other users, including any documentations of interactions, notes or comments, test results, etc. The email may include metadata to record which party initiated the exchange, timestamps, and so forth.

In some embodiments, the wearable device may generate and display shared virtual content (e.g., via the display 220) to the user; and the user may edit or modify the information in the virtual content. For example, the second user's wearable device can present a virtual content the second user, which contains the same information as the virtual content perceived by the first user. If the first user's wearable device receives a modification to the virtual content from the first user, the same modification can be communicated to the second user's wearable device and can be reflected by the second user's wearable device. In this example, the first user and the second user's wearable devices may provide an indication that there is another user actively "in" the same patient file.

A wearable device can be configured to share only a portion of the content perceived by the user. For example, the wearable device of a first user can identify a second user to share the information perceived by the first user. The wearable device of the first user can receive a request from the second user's wearable device to share the content. The wearable device can determine access privilege of the second user and only share the portion of the information in the first user's FOV to which the second user has access. The second user's wearable device can accordingly present to the second user a subset of information in the first user's FOV.

The wearable device can also share and record the data received from medical devices. In some embodiments, while receiving data from a medical device, the wearable device can present (e.g., via the display 220) to the user medical information associated with the data retrieved from the external medical devices. For example, the wearable device can present a patient's electrocardiograph (ECG) as the wearable device receives the data from the corresponding monitoring device attached to the patient. The data (or a subset of the data) can be shared with other users using the techniques described herein. The user can also edit the medical information before sharing it with the other users.

Figure 18:
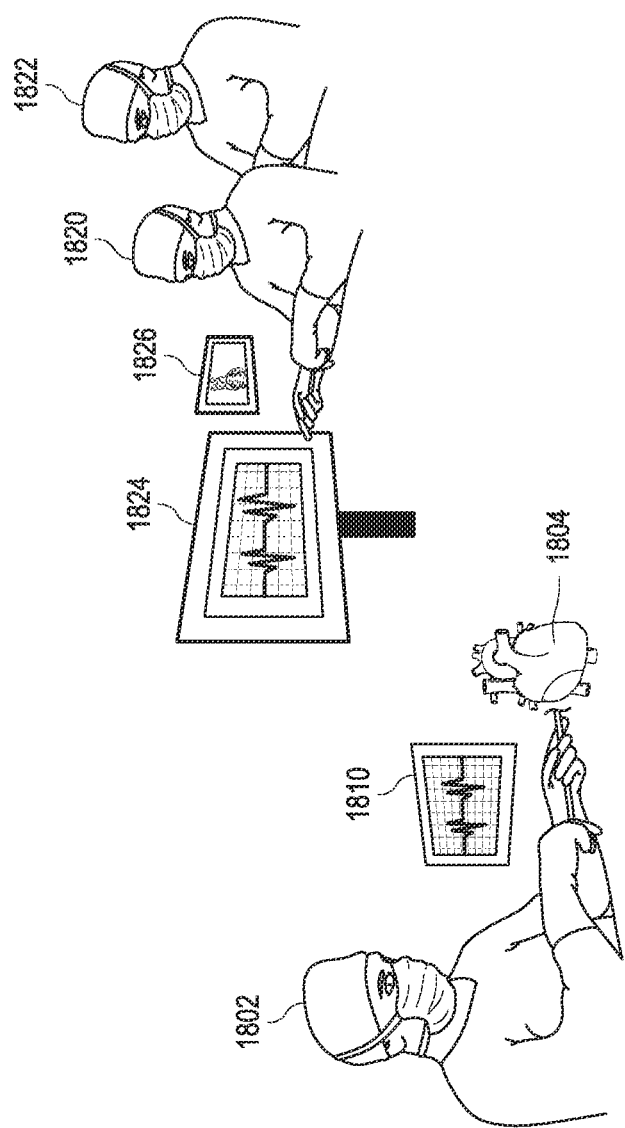
FIG. 18 illustrates an example of sharing medical information among multiple healthcare providers.

FIG. 18 illustrates an example of sharing medical information among multiple users, which may be performed under the computing environment 1700 described with reference to FIG. 17. In the example in FIG. 18, a surgeon 1802 is operating on a patient's heart 1804. The surgeon 1802 can be assisted by two nurses 1820 and 1822. The operating room may also include one or more medical devices (e.g., an ECG/EKG machine) monitoring the real time conditions of the heart 1804 or other physiological parameters of the patient. The medical device can output the patient's heart condition to a physical display 1824.

In this example, the surgeon 1802, and the two nurses 1820, 1822 can wear their respective wearable devices. The surgeon 1802 can see the patient's heart 1804 through the wearable device, while the two nurses 1820 and 1822 can perceive the physical display 1824 via the wearable device. However, the surgeon 1802 may not be able to perceive the physical display 1824 as it is not in his field of view, and the two nurses 1820, 1822 may not perceive the heart 1804 which is outside of the field of view of the two nurses 1820, 1822.

Advantageously, as illustrated in FIG. 18, the surgeon 1802 and the two nurses 1820, 1822 can share their respective field of views with each other via the wearable devices. For example, the surgeon 1802 and the two nurses 1820, 1822 can participate in a sharing session. The surgeon 1802 can perceive the virtual screen 1810 which includes information displayed by the physical screen 1824, which is inside of the two nurses' field of view but is outside of the surgeon's 1802 field of view. Information on the virtual screen 1810 can be rendered based on images captured by the outward-facing imaging systems of a wearable device worn by the nurse 1820 or 1822. In some situations, the medical device can also be in communication with the wearable device via wired or wireless communication channels, and the wearable device can present the patient's conditions in real-time via the virtual screen 1810.

The surgeon 1802 can also share at least a portion of his field of view with the nurses 1820, 1822. For example, the wearable device of the surgeon 1802 can communicate images of the heart 1804 as observed by the outward-facing imaging system to the wearable devices of the nurses 1820, 1822.

In some implementations, the nurses or the surgeon may provide an indication to the wearable devices to initiate a sharing session with other people in the room. For example, upon receiving an indication from the nurse 1802 or 1804 (or upon detecting any other triggering events discussed above), the nurse's wearable device may send a request to the surgeon's wearable device to share what the nurses are seeing on the surgical monitor to the surgeon's wearable device. Upon receiving the request from the nurse's wearable device, the surgeon's wearable device may present the virtual content screen 1810 (e.g., to show information perceived by the nurses on the physical display 1824) to the surgeon while the surgeon 1802 is operating on the patient. The virtual content screen 1810 can contain information associated with the data that the medical device collects at real time. Accordingly, the surgeon's wearable device can give the surgeon 1802 real time medical information about the situation of the patient's heart as shown in the ECG monitor, even though such ECG monitor is not physically in the surgeon's 1802 field of view.

The surgeon's wearable device can generate alerts to the surgeon during the operation if the surgeon's wearable device determines, based on environment information (such as, e.g., information received from the medical devices in the operating room), there is an abnormality in the patient's heart. In some embodiments, the surgeon's wearable device may not generate and display a virtual screen 1810 showing the real time medical information about the situation of the patient's heart if the ECG monitor shows that the condition of the patient's heart is normal. The surgeon's wearable device may only generate and display a virtual content screen to the surgeon 1804 when there is an abnormality in the patient's heart based on the information on the surgical monitor. The surgeon 1802 or the nurses 1820, 1822 can configure settings for viewing information outside of the field of view on their respective wearable devices. For example, the surgeon 1802 or the nurse 1802,1822 can configure a setting such that the nurse's wearable device only shares the information on the physical display screen 1824 with the surgeon 1802 when there is an abnormality in the patient's heart data. In some cases, the nurse's wearable device alone or in combination with the remote computing system 1720 can analyze the data collected from one or more medical devices and determine whether or not there is an abnormality.

As another example, the surgeon can share the image of the patient's heart 1804 with the nurses 1820 and 1824 based on the presence of a triggering event. The surgeon's wearable device may send a request to the nurses' wearable device to share the image of the heart. The nurse's wearable device, upon receiving request from the surgeon's wearable device, can present the virtual content screen 1826 showing images of the patient's heart 1804 as seen by the surgeon.

Although the example in FIG. 18 is described with reference to ECG/EKG data, the wearable device can also present other types of medical information on virtual screen(s). For example, the virtual screen 1810 may also include medical information of the patient's other parameters collected by the other devices, such as the patient's blood pressure, brain activity, temperature, etc. The nurses 1820 and 1822 in the example of FIG. 18 can also be any other type of users, such as other surgeons, medical interns, residents, students, patients, etc. The surgeon's wearable device (or another user's wearable device) may also record the operation for later review by an authorized user (e.g., the surgeon himself, the patient, the patient's primary healthcare provider, etc.). In the example of FIG. 18, the surgeon 1802 is performing a heart surgery. In other examples, a first healthcare provider can do any type of medical procedures (or any types of interaction with the patient as illustrated in FIG. 15). Further, the nurses 1820 and 1822 need not be located in the operating room in which the surgeon is operating. For example, the nurses could be located in an adjacent room. In another example, the surgeon may share information on the heart with a consulting physician or a pathologist, each of whom may be located remotely from the operating room (e.g., elsewhere in the hospital or in an entirely separate geographic location).

Management of Medical Information

As described with reference to FIGS. 15 and 18, the first user can make notes or comments when his device is documenting an interaction with the patient. The first user can share the notes or comments with the second user as well through their devices. The first user can also instruct his wearable device to keep the notes or comments private. In some embodiments, the first user may share the notes or comments with the second user while he is making the notes or comments through their devices. As described with reference to FIG. 15, while interacting with the patient, the wearable device can take an image of the patient. The user may have the option to send a request to the wearable device to enlarge the image or edit the image. In editing the image, the user may virtually separate parts of the image, flag different positions of the image, remove several parts of the image, etc.

Figure 19:
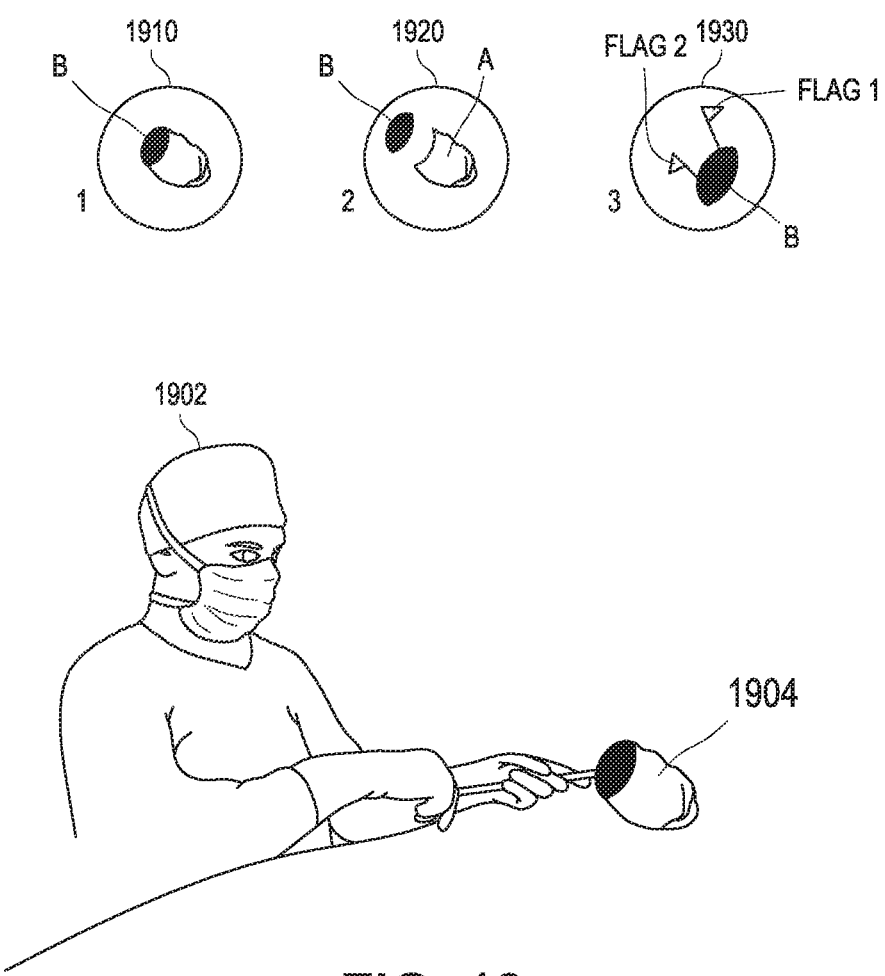
FIG. 19 illustrates an example of adding virtual content to images taken during a medical procedure.

FIG. 19 illustrates an example of adding virtual content to images taken during a medical procedure. Advantageously, in some embodiments, the wearable device can improve efficiency in a medical procedure by allowing the user to send medical information (e.g., image information, camera orientation, location of the image or the procedure, time, etc.) to other users while the medical procedure is in progress or after the medical procedure. For example, the wearable device can send the tumor orientation in a tumor resection procedure to a pathology lab. The wearable device can also send information to a different location, group, or lab for additional assessment or analysis. The medical information may include images of specific organs, symptoms, etc. In some implementations, the wearable device can allow a recipient or the sender to mark the medical information in a virtual environment so that no physical marks are needed. For example, rather than marking on a physical sample of a tumor, a doctor in the pathology lab can mark an image (e.g., a 2D or 3D image) of the tumor during an operation occurring in a hospital remote from the pathology lab.

The wearable device can also facilitate an efficient and non-invasive method to analyze medical information. For example, during a tumor resection, a physician typically places physical flags in the tumor to indicate which direction is the up. Advantageously, the wearable system can be configured such that a user can add virtual flags (alone or in combination with texts or other visuals) to the tumor. The wearable device can then send the virtual content (e.g., an image of the tumor with virtual markers) to the patient's chart or to another user, such as a pathology lab, using internet, Bluetooth, wireless sharing capabilities, which provides a faster way to transfer the information (e.g., as opposed to mailing the sample to the radiologist) and a non-invasive way to mark the physical sample (e.g., poking of the tumor is not needed).

To share content perceivable by the first user to a second user, the wearable device can share a virtual screen perceived by the first user to the wearable device of the second user. The virtual screen may include information (e.g., texts, drawings, comments, annotation of physical or virtual objects) inputted by the first user. For example, a surgeon in an operating can share his virtual screen with a radiologist while he is looking at a tumor on a patient. The surgeon can mark regions of the tumor on the virtual screen and communicate such marks to the radiologist. The wearable device can also save the virtual content with virtual markers in the patient's medical record and send a notification to the users in another location that their attention is needed. For example, the wearable device can put virtual flags on a virtual tumor image to indicate which direction is in a fiducial direction (e.g., upward), the orientation of the camera that captured the image, contextual information (e.g., notes or commentary from the surgeon relating to the image, a body part such as the tumor, and so forth), etc. The wearable device can send the virtual tumor image with the virtual flags directly users in a pathology lab by sharing virtual content. The wearable device can also update the virtual tumor image with the virtual flags in the patient's medical record and send a notification to the users in the pathology lab. Upon receiving the information from the surgeon, the users in the pathology lab can also make additional annotations as virtual content using their respective wearable devices. Such additional annotations can also be communicated to the surgeon's wearable device.

In the example of FIG. 19, a surgeon 1902 is performing a medical procedure on a patient's organ 1904. The surgeon 1902 may determine that the organ 1904 contains some abnormality. The wearable device of the surgeon 1904 may take an image of the organ 1904. After taking the image, the wearable device to generate and display a first virtual content screen 1910 containing the image of the organ. The surgeon may determine that the organ 1904 contains two parts: a normal part and an abnormal part that needs to be removed. The surgeon may mark in the first virtual content screen 1910 a part A (the normal part) and a part B (the abnormal part). To confirm the positions of the resection, the surgeon 1902 may instruct (either by key words, totem or gesture activation) his wearable device to virtually separate part A and part B of the image 1910. Upon receiving the request to virtually separate the part A and the part B, the surgeon's wearable device may process and analyze the data in the image. The surgeon's wearable device may then generate and display a second virtual content screen 1920 to the surgeon 1902 where the surgeon's wearable device shows the part A and the part B are separated, which may assist in the examination or resection of the abnormal part.

The wearable device can also allow a user to manipulate the image of the tumor. For example, the surgeon 1902 can instruct his wearable device (e.g., using hand gestures or voice command) to enlarge the image of the abnormal part B. Upon receiving such instructions, the surgeon's wearable device may generate and display an image of the abnormal part B as shown in the virtual screen 1930. Based on this enlarged image, the surgeon can better determine which positions he should remove the part B from the organ 1904. The surgeon can also input comments or markers associated the tumor. For example, the surgeon may place two flags (flag 1 and flag 2) on an image of the tumor as shown in the virtual screen 1930. The flag 1 and the flag 2 can indicate, for example, direction or orientation of the tumor, positions of resection, locations of abnormalities, direction of the part B with respect to the body (e.g., flag 1 is at an anterior position relative to flag 2), etc.

In some implementations, the surgeon can also share the image of the tumor with another user of a wearable device. The surgeon, to confirm the positions of the flag 1 and the flag 2, can share the information in the first, the second, or the third virtual screens to a second user. The second user can be a pathologist who will analyze the abnormal part B. The surgeon can save the three virtual content screens in the patient's medical record and the second user can then view the virtual content screens in the patient's medical report. The surgeon can also share the three virtual content screens with the second user as illustrated above with reference to FIG. 18. The surgeon may also have the option to send the three virtual content screens to the second user in real-time as the surgeon is performing the surgeon. In some embodiments, advantageously, when the surgeon 1902 has made certain remarks (e.g., placing the flags 1 and 2), the surgeon's wearable device may send the surgeon 1902 a notification asking whether the surgeon wants to send the virtual screens or annotations to another user.

As another example, the wearable device of the surgeon 1902 may generate and show virtual content of the area the surgeon is working on. The virtual content screens 1910, 1920, and 1930 may show the area being operated on during a surgery at different points in time. For example, the first virtual screen 1910 may show the organ 1904 before the abnormality is removed. The second virtual screen 1920 may show the organ 1904 after the surgeon removes the abnormal part: it includes a Part A (the normal part) and a part B (the removed abnormal part). The surgeon can then enlarge the abnormal part B on the third virtual screen and virtually flag the parts where the surgeon wants to conduct more tests on. For example, the flag 1 and flag 2 may indicate the parts that the surgeon wants pathology tests to be performed on. As another example, flags 1 and 2 can indicate the orientation of the tumor (such as, e.g., by indicating the upward direction associated with the tumor). The surgeon can share the first, the second, or the third virtual content screens with a second user (e.g., a pathologist). By sharing one or more of these screens, the second user can have more context on where in the organ the abnormal part B came from, how the organ or abnormality were positioned in the patient's body, whether or where additional resection of an organ may be needed, etc. when he conducts the pathology test. Also, the use of virtual flags can help preserve the integrity of the abnormal part before analysis, because an actual, physical flag is not placed into the abnormal part B.

Even though in the example of FIG. 19, only the surgeon is editing or flagging the virtual image, in some embodiments, multiple users, when sharing the first, the second, or the third virtual content screens, can edit or flag the image. Various edits and flagging by different users can be recorded in the patient's medical record and other users can automatically get the updated images. For example, the flag 1 or 2 may be placed by another physician who receives the image of the tumor provided by the surgeon.

Figure 20:
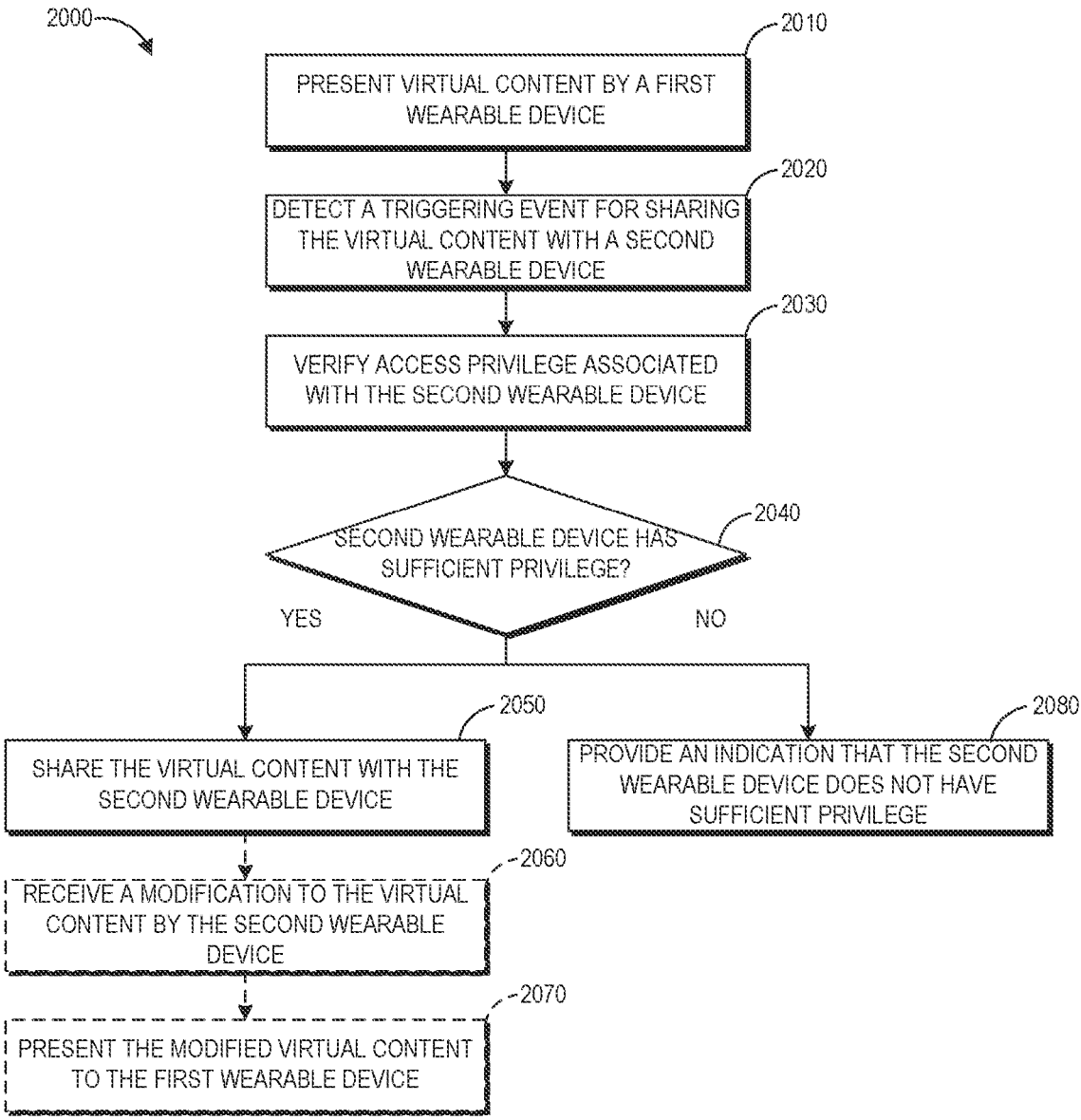
FIG. 20 is a flowchart that illustrates an example process of sharing virtual content between multiple healthcare providers.

FIG. 20 is a flowchart that illustrates an example process 2000 of sharing virtual content between multiple users. The example process 2000 can be performed by the wearable system 200 described herein. For example, the example process 2000 can be performed by the local processing and data module 260 of one or more wearable devices alone or in combination with the remote processing module 270.

At block 2010, the process 2000 presents virtual content by a first wearable device of a first user. The first user's wearable device may present virtual content to the first user. The virtual content may be presented via one or more virtual screens.

At block 2020, the process 2000 detects a triggering event for sharing the virtual content with a second user via a second wearable device. The trigger event may be a request by the first user to share the virtual content with another user or may be a request by the second user to view the information perceivable by the first user. The request may be key words, input on a totem, or a gesture. The triggering event may also be based on a condition in the first or the second user's environment. For example, content sharing may be triggered in response to a detection of an emergency of a patient (e.g., such as, e.g., a sudden bleeding or an anomaly in the heart rate).

At block 2030, the process 2000 verifies an access privilege associated with the second user. The verification of the access privilege may be conducted by the data security management system 1212 shown in FIG. 12. The access privilege may be verified by the healthcare database system 1220 which can verify the second user's access privilege based on the second user's profile associated with a medical record. In certain implementations, the patient may control who has access to his medical records. The patient can set up the access rules at the healthcare database system 1220 for verifications. The patient system may also itself verify the access privilege of the second wearable device.

At block 2040, the process 2000 can determine whether the second wearable device has sufficient access privilege for accessing the virtual content. For example, the first or the second wearable device can receive an indication from the healthcare database system 1220 on whether the second user has an access privilege to the virtual content. If the second user has access privilege to the virtual content, the process 2000 moves to block 2050 where the virtual content, as perceived by the first wearable device, is shared with the second user's wearable device. In some situations, the first user can indicate what part of the virtual content (e.g., a specific part of the virtual content, or the entire virtual content) he wants to share with the second user's wearable device. The second user's wearable device can generate and display a second virtual content screen showing the virtual content received from the first wearable device.

At optional block 2060, the second wearable device can receive a modification to the virtual content. The second user can modify the virtual content in the second virtual content screen and the second user's wearable device can record such modification. Such modification can be communicated to the first wearable device.

At optional block 2070, the first wearable device can present the modified virtual content to the first user. The second user's wearable device may update the modified virtual content in the patient's medical record and send a notification to the first user about the modification. The first user's wearable device can then update the first virtual content screen to show the modified virtual content to the first user.

If the second user does not have access privilege to the virtual content as determined at the block 2040, the process 2000 can provide an indication to the first user's wearable device that the second user does not have an access privilege to the virtual content at a block 2080. The process 2000 may also send, to the patient of the medical record, an indication that the second user was trying to access the virtual content. The indication to patient system may include the user's name, the information associated with the virtual content. The process 2000 may store this incident of denied access in the patient's medical report.

Although some examples in FIGS. 18-20 describe sharing virtual content or displaying virtual content using a virtual content screen, the wearable devices can display and share virtual content in the 3D space using any types of techniques. The virtual content is not required to be rendered on a virtual content screen. The virtual content can appear as a different type of virtual object or have other graphical appearances which do not appear to be part of the virtual content screen.

Examples of Accessing and Presenting Virtual Content Based on Contextual Information The wearable device can present virtual content based on contextual information. Contextual information can include information associated with a user of a wearable device, such as, e.g., a location of the user, a pose of the user, an emotional state of the user, a level of access privileges, etc. Contextual information can also include information associated with the user's environment, such as, e.g., a physical object, a virtual object, a person in the user's environment, etc.

The wearable device can determine contextual information based on data acquired by one or more environmental sensors, data accessed from the remote data repository 280 or the healthcare database system 1220, in combination or the like. For example, the wearable device can analyze data acquired by the outward-facing imaging system 464 using one or more object recognizers to identify physical objects or persons in the user's environment. The one or more object recognizers can apply various computer vision algorithms (including, for example, face recognition algorithms or object recognition algorithms) to identify the physical objects. As another example, the wearable device can determine the pose of the user using the IMUs and determine the location of the user using data acquired from a GPS.

The wearable device can access virtual content and present the virtual content on the 3D display based on contextual information. The virtual content may include information from a patient's virtual medical records, or virtual information specific to a location. The virtual content may also include an alert. The alert may include a visual focus indicator, a message, a sound, etc., alone or in combination. The focus indicator may be near the physical or virtual content that triggered the alert. The alert message can include a brief description explaining the event that triggered the alert. Examples of presenting virtual content based on contextual information are further described with reference to FIGS. 21-24.

Contextual Information Associated with the User's Environment

A wearable device of an HCP may recognize a person in the surroundings based on data acquired by one or more environmental sensors. For example, the wearable device can recognize a person (e.g., a patient) using techniques (such as e.g., face recognition, voice recognition, etc.) described with reference to FIGS. 12 and 14A. The wearable device can present the patient's information on the 3D display. For example, the wearable device can present patient specific information such as, e.g., the patient's name, procedure, diagnosis, anatomical site being operated, medications, and so forth. Advantageously, in some embodiments, the wearable device can improve the efficiency and increase the quality of patient care by recognizing the patient's identity using facial recognition techniques and present patient specific information accordingly. For example, physicians often have to deal with many patient charts in their office. With facial recognition, the physicians can look at the patient and automatically perceive the patient's information without needing to interact with the patient. In some embodiments, the facial recognition is used in conjunction with data acquired from the outward-facing imaging system. For example, the wearable device can identify a patient chart based on an image acquired by the outward facing imaging system and determine that the patient identified in the patient chart is the same patient recognized with the face recognition technique. As another example, the wearable device can check the patient's identity determined with face recognition against the scheduling information of an operating room to make sure that an HCP of the wearable device will be (or is) operating on the correct patient.

Figure 21:
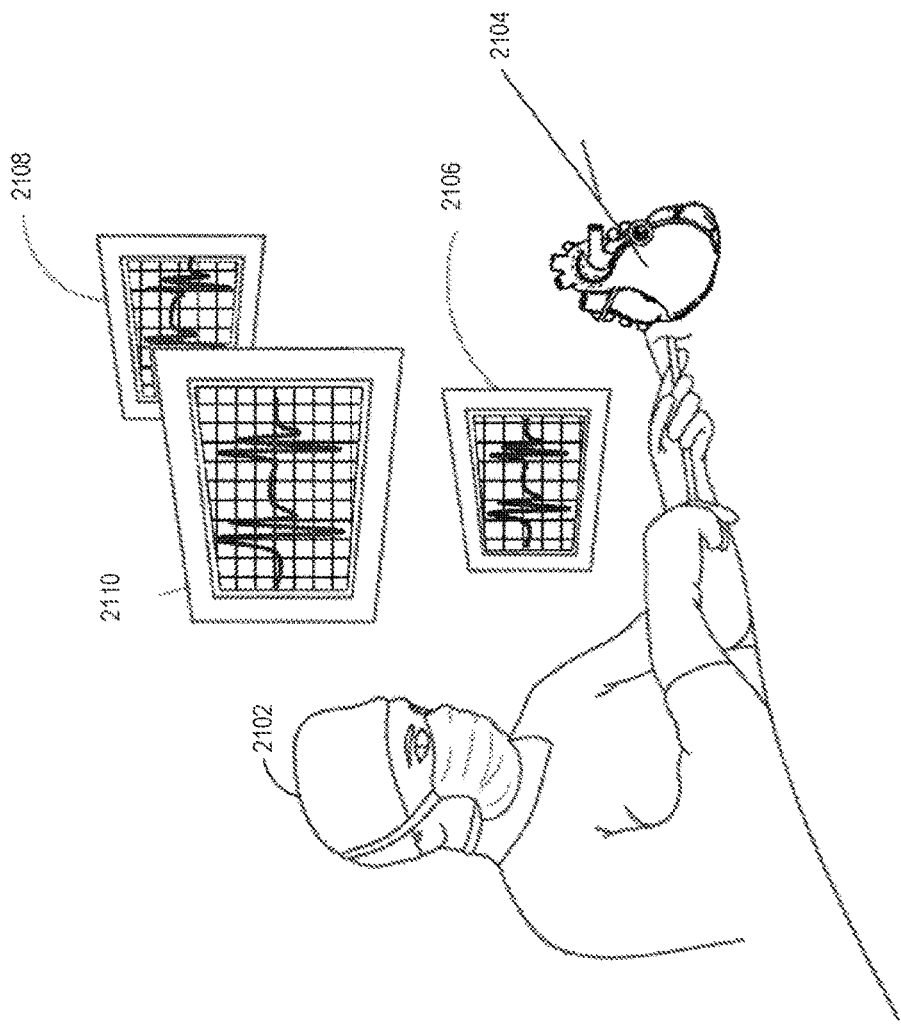
FIGS. 21, 22A, 22B, and 23 illustrate examples of presenting virtual content based on contextual information.

FIG. 21 illustrates an example of presenting virtual content based on contextual information associated with a user's environment. In this example, a surgeon 2102 can wear a wearable device. The wearable device can identify the patient based on facial recognition techniques. The wearable device can retrieve the virtual medical records associated with the patient. The wearable device can present relevant portions of the virtual medical records on the 3D user interface as shown by the virtual objects 2106, 2108, and 2110.

The wearable device can determine the type of the surgery based on the patient's virtual medical records or information associated with the operating room. In this example, the wearable device can determine that the surgeon 2102 is performing a minimally invasive heart surgery based on the scheduling information of the operating room. Accordingly, the wearable device can present a model 2104 of the patient's heart in the 3D space to help the surgeon 2102 to identify the relevant regions which the surgeon should operate on. The wearable device can also present the patient's physiological data, such as the respiratory rate on the virtual object 2108 and the ECG data on the virtual object 2110, as well as present patient's personal information such as his age, medical history, allergies, etc., on the virtual object 2106.

Additionally or alternatively, the wearable device of an HCP can recognize a portion of the user's body, such as a limb or an organ, based on data acquired from the outward-facing imaging system. The wearable device can access virtual medical records to determine whether the HCP is operating on the correct part of the user's body. The wearable device can present an alert if the HCP is about to operate or is operating on the wrong part of the user's body.

Figure 22A:
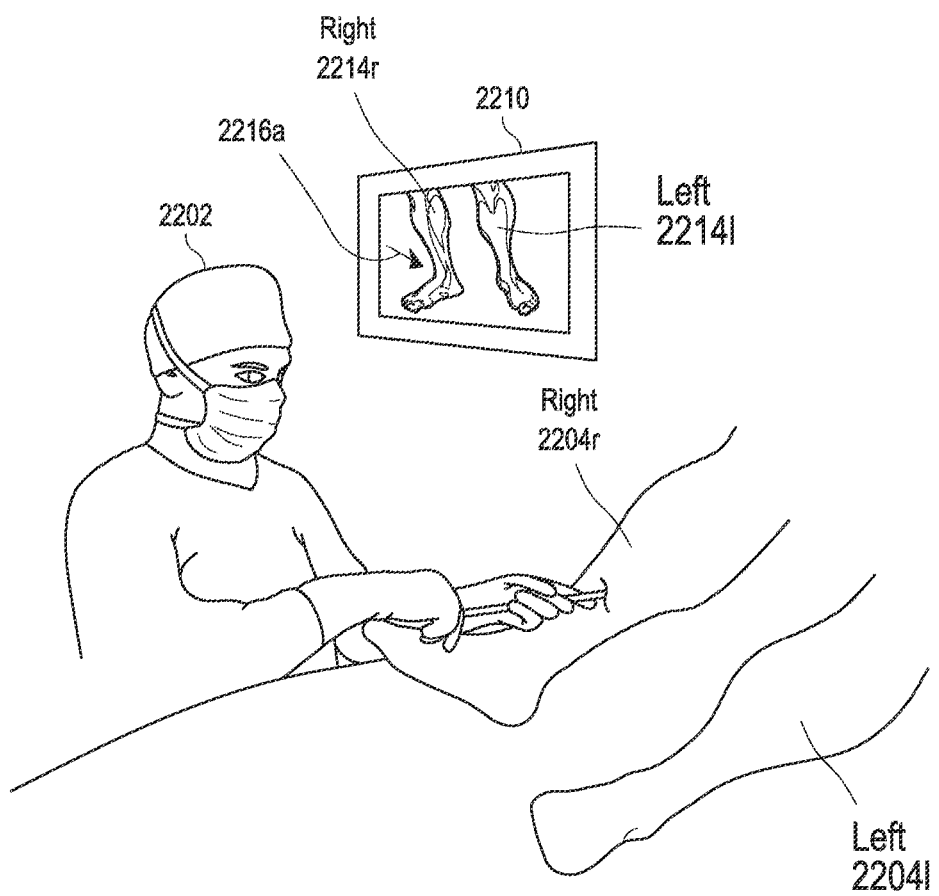
Figure 22B:
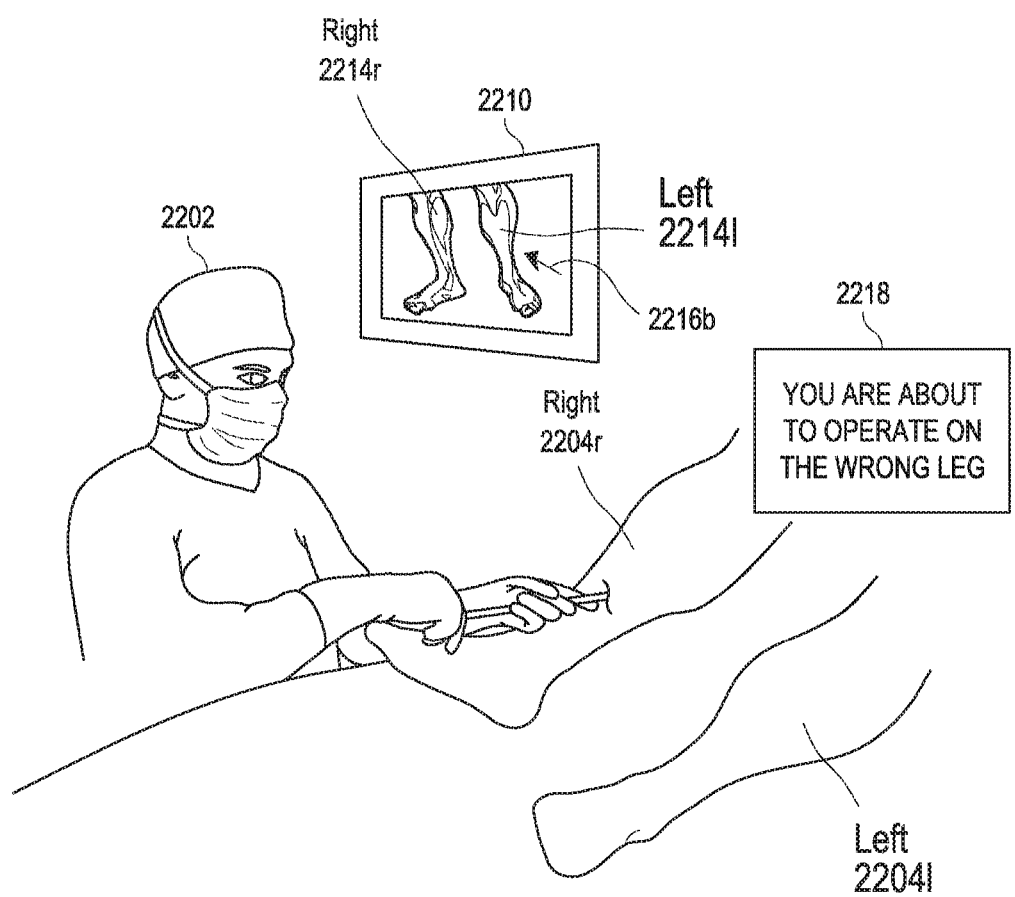

FIGS. 22A and 22B illustrate an example of presenting an alert based on contextual information associated with a user's environment. In the example of FIG. 22A, a surgeon 2202 is in an operating room. The surgeon 2202 can perceive, via the wearable device, the virtual object 2210 which includes an image of the patient's legs 2214r, 2214l. As described with reference to FIG. 21, based on the contextual information, the wearable device of the surgeon can determine information relating to the type of operation the surgeon is going to perform on the patient. For example, the wearable device can access the scheduling information of the operating room and determine that the surgery scheduled for the patient involves a procedure on the patient's right leg 2204r. The wearable device can access the patient's medical record to confirm that the operation should be performed on the right leg 2204r. The wearable device can present to the surgeon a focus indicator (in the virtual object 2210) indicating the correct leg for operation is the right leg 2204r. For example, in FIG. 22A, the wearable device displays an arrow 2216a pointing at the image 2214r of the patient's right leg, which provides a visual indication to the surgeon 2202 as to which is the correct leg for the operation.

The wearable device can monitor the surgeon's interaction with the patient. Based on the data acquired by the outward-facing imaging system 464, the wearable device can detect that the surgeon 2202 is holding a scalpel 2204. In the example in FIG. 22A, the scalpel is operating on the right leg 2204r, which is the correct leg.

In contrast to the example shown in FIG. 22A, in the example shown in FIG. 22B the patient's left leg 2204l is the correct leg for the operation (as indicated by the arrow 2216b pointing to the left leg 2214l in the virtual object 2210). In this example, the wearable device determines that the scalpel is operating on the right leg 2204r or that the scalpel is moving toward the patient's right leg 2204r. For example, the outward-facing imaging system of the wearable device can image the patient's lower limbs and use computer vision techniques to identify the patient's limbs, the position of the surgeon's hands, the presence and location of the scalpel in the surgeon's hands, etc. The wearable device can determine that the surgeon is about to operate (or is operating) on the patient's right leg 2204r, which is not the correct leg for the surgery in FIG. 22B. The wearable device can present a visual alert warning 2218 that the surgeon 2202 should not operate on the right leg 2204r. The alert may include a message which informs the surgeon 2202 that he is about to operate on the wrong leg. The alert warning 2218 can be presented to appear near the patients' left leg 2204l to emphasize that the left leg 2204l is the correct leg. In other embodiments, the alert warning 2218 may be displayed over the patient's right leg 2204r, thereby at least partially occluding the surgeon's view of the incorrect leg, which provides an additional visual indication to the surgeon that there may be a problem occurring. In some embodiments, the alert also includes a recommended measure to correct the surgeon's mistake (such as, e.g., a reminder that the surgeon should operate on the left leg 2204l). Additionally or alternatively, the alert may include a focus indicator. For example, the arrow 2216b may change color (e.g., from green to red) or starts to flash which can emphasize that the left leg 2204l is the correct leg. The alert warning 2218 may be accompanied by an audible alert, for example, the speaker system of the wearable device may play the message shown in FIG. 22 to help ensure that the surgeon does not continue attempting to operate on the incorrect leg of the patient. Although this example describes a procedure on the leg of the patient, this is for illustration and is not intended to limit the scope of the alert warning described herein. Further, the use of the alert is not limited to surgery and can be provided in wearable devices used by other HCPs (e.g., to alert an examining physician that he is attempting to examine a skin rash on the patient when she actually complained about left hip pain (see, e.g., FIG. 15)).

Contextual Information Associated with a User

Contextual information can include information specific to a user of a wearable device. Because multiple users may use the same wearable device, the wearable device may need to verify the user's identity in order to determine contextual information specific to the user. The wearable device can use various techniques of described with reference to FIGS. 14A and 14B to determine and verify the identity of the user. As an example, the wearable device can create and store user profiles in the medical data store 1222. When the wearable device is actuated by a user, the wearable device can obtain the user's biometric information or require the user to provide certain inputs for verifying of the user's identity. Based on the biometric information or the user inputs, the wearable device can access an appropriate profile to determine the access privileges of the user. The profile can include information about the user, such as, e.g., his name, date of birth, graduate school name, graduate year, specialty, hospital information, access privileges, etc.

Advantageously, in some embodiments, the profile includes the user's voice characteristics or eye characteristics (e.g., the iris or retina pattern) of the user. The wearable device can collect and analyze the person's eye characteristics based on data acquired by the inward-facing imaging system 462 (e.g., an eye-tracking camera). For example, an image of the person's eye can be segmented to identify the iris and then an iris code can be generated, which uniquely identifies the person. The wearable device can match the eye characteristics collected by the wearable device with the eye characteristics in the profile. If the wearable device determines there is a match, the wearable device can determine that the user's identity has been verified. If the wearable device does not find a match, the wearable device can generate an alert indicating that the user is not authorized to use the wearable device. The user can then try a different identification method. In some embodiments, the wearable device may send notifications to one or more users who are authorized to use the wearable device. The notification can include the data, time, or location of the unauthorized access. The wearable device may also store the notifications regarding unauthorized access in the patient's medical record.

As an example of presenting virtual content based on the user's information, during an open heart surgery, an HCP's wearable device can analyze the HCP's pose (such as, e.g., the direction of gaze) to determine the object that the HCP is currently interacting with. For example, if the HCP is staring at a window of the operating room for an extended period of time (e.g., 5 minutes, 10 minutes, etc.) rather than the heart, the wearable device may determine that the user is distracted. As a result, the wearable device can generate an alert to bring the HCP's focus back to the surgery. In some embodiments, the wearable device compiles all alerts during the surgery and generates a report.

As another example of presenting virtual content based on the user's information, the wearable device can determine that the user is a receptionist whose job duty involves scheduling appointments. Accordingly, the wearable device can automatically present an appointment scheduling tool on the 3D user interface. However, when a doctor uses the same wearable device, the wearable device may present the doctor's weekly schedule rather than the tool for scheduling the appointment.

Figure 23:
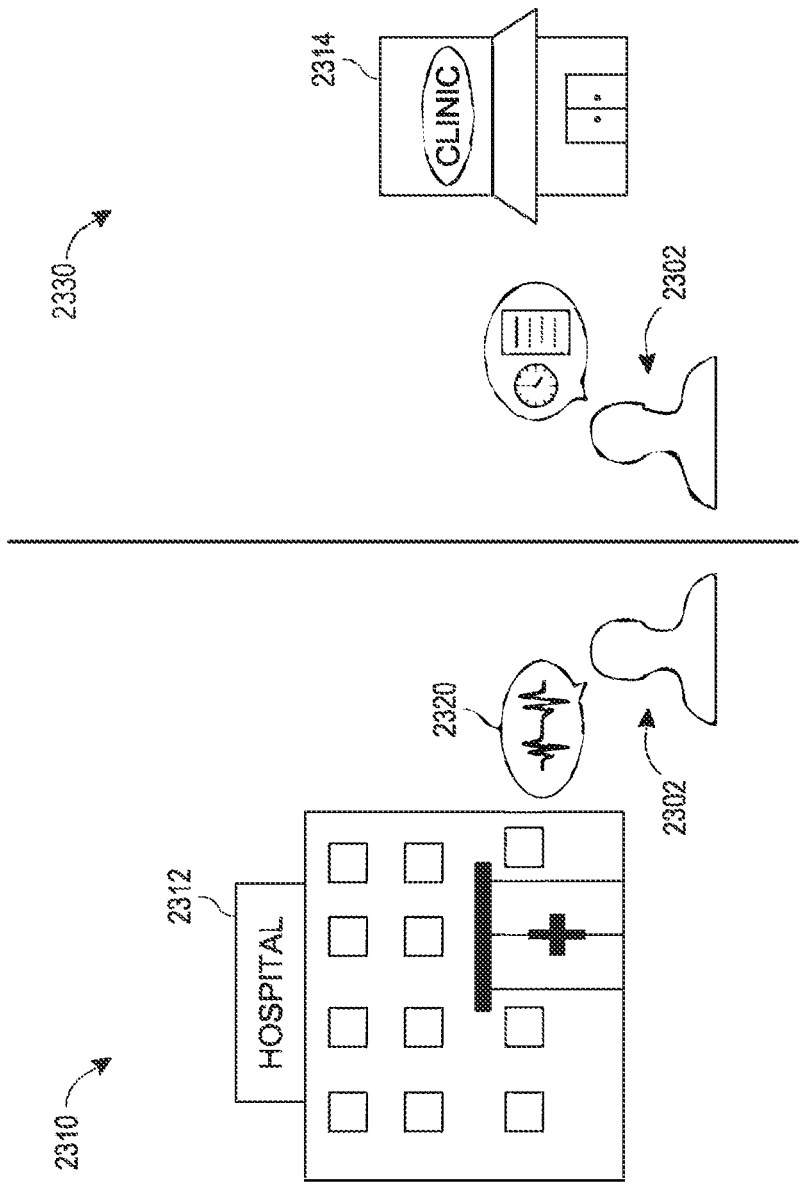

FIG. 23 illustrates an example of presenting virtual content based on a user's location. The user's location may be determined based on one or more environmental sensors of the wearable device. For example, the wearable device can determine the user's location based on data acquired by a GPS. The wearable device can also determine the user's location based on images acquired by the outward-facing imaging system. For example, the wearable device can detect a building using a computer vision algorithm. The wearable device can further determine that the building is a hospital because the image includes a sign with the word "hospital" or other characteristic landmark.

FIG. 23 shows two scenes 2310 and 2330. The location of the scene 2310 is a hospital 2312 while the location of the scene 2330 is a clinic 2314. The user 2302 wears a wearable device in both scenes.

As an example, the user 2302 may be a patient. In the scene 2310, the wearable device's location sensors (such as, e.g., GPS) can acquire the patient's location data. The wearable device can process the location data and determine that the user is at the hospital 2312. The wearable device can access the patient's virtual medical records, for example, by communicating with the healthcare database system 1220. The wearable device can analyze the patient's virtual medical records, and determine that the patient has an operation scheduled at the hospital 2312. Accordingly, the wearable device can present a building map of the hospital 2312 which includes a route to the operating room. As the doctor moves inside of the building, the wearable device can analyze the data acquired by the outward-facing imaging system 464 (or the GPS data) of the wearable device to determine the doctor's position inside the hospital and update the route information accordingly. The wearable device can also present the operating room's information 2320 on the 3D display. For example, the wearable device can present information on the procedure, such as, e.g., the risks of the procedure on the 3D display.

In the scene 2330, the wearable device can determine that the patient is at the clinic 2314 based on the user's location information. The wearable device can accordingly display the patient's scheduling information at the clinic 2314, such as, e.g., the time of the appointment and the physician that the patient will see at the clinic 2314.

As another example, the user 2302 may be a doctor who works at the hospital 2312 and the clinic 2314. When the doctor is at the hospital 2312, the wearable device can determine that the doctor will perform a surgery at operation room A. Accordingly, the wearable device can present information of operating room A (such as e.g., medical equipment that is in the operating room). The wearable device can also present a map or route information from the doctor's current location to the operating room A. The wearable device can also inform the patient that the doctor will operate on. The patient information may be stored on the hospital's network (e.g., the hospital's server), in a file cabinet, or in the healthcare database system 1220. The wearable device can automatically identify the storage location of the patient's files and access the files from the storage location. In some embodiments, where the patient's files were stored in a file cabinet, the wearable device may provide an indication of the location of the patient's file to help the doctor to find the patient's file.

When the doctor turns his wearable device on at the clinic 2314, the wearable device can detect that the doctor's current location is the clinic 2314 (rather than the hospital 2312). The wearable device can communicate with a clinic's database to retrieve relevant information of the doctor's cases, such as, e.g., the patients whom the doctor will see, the procedures that the doctor will perform in the clinic, exam rooms, voicemail messages received to the clinic after business hours, etc. The wearable device can obtain the relevant information by communicating with the clinic's cloud network using Bluetooth or wireless technologies. The information of the doctor's cases may be uploaded to the cloud network by an assistant from the day before.

As another example of presenting virtual content based on location information, the wearable device can monitor a user's environment and that the user has entered into a specific operating room in a hospital. The wearable device can access the world map 920 (such as, e.g., an internal surgical unit map) associated with this particular operating room to determine the objects associated with the operating room. The world map of this operating room may be created and updated by multiple users. Details on updating and building a world map are described with reference to FIGS. 9 and 17. The wearable device can also display default parameters for this particular operating room, such as, e.g., time and patient for the next procedure, and so on. The wearable device can access the nurse's schedule uploaded to the hospital network to determine the default parameters of this particular operating room.

Figure 24:
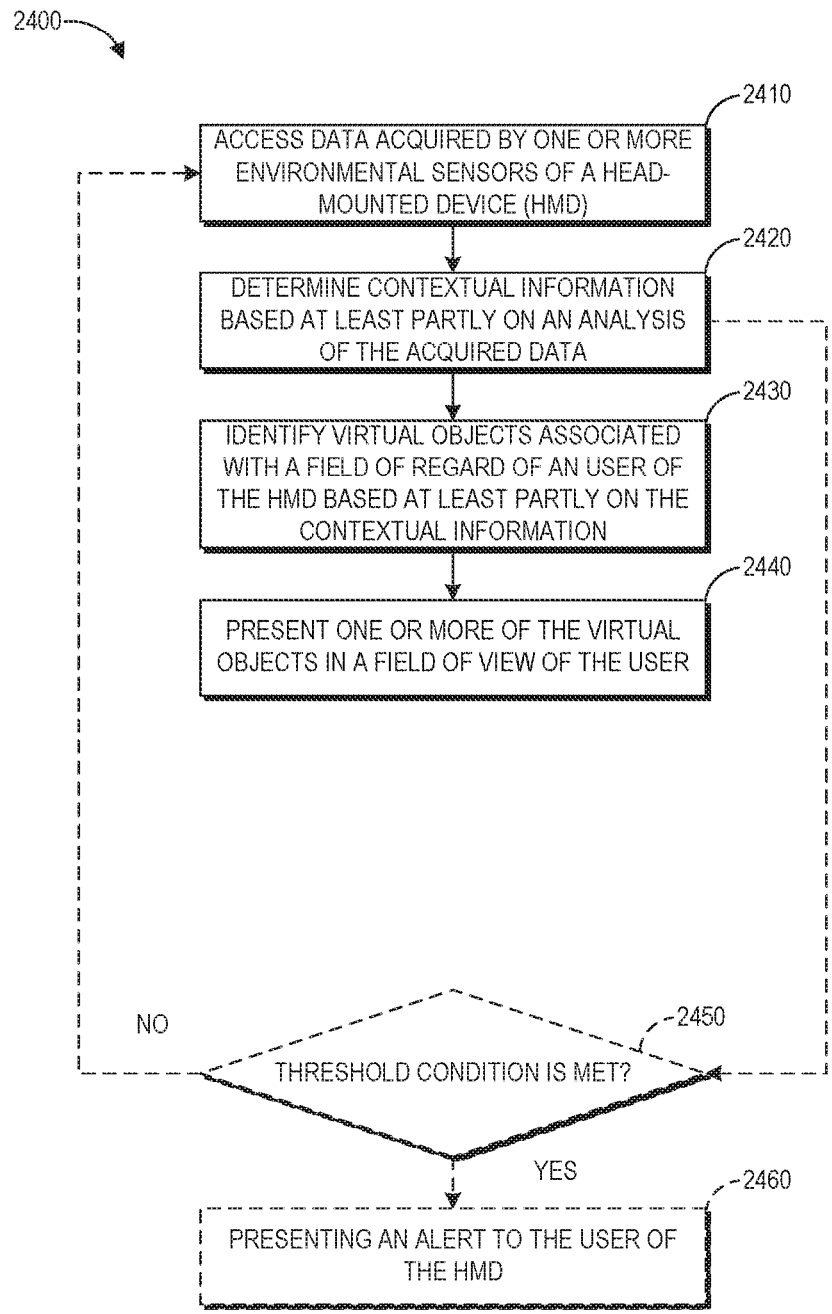
FIG. 24 is a flowchart that illustrates an example process of accessing and presenting virtual content based on contextual information.

Example Processes of Accessing and Presenting Virtual Content Based on Contextual Information FIG. 24 is a flowchart that illustrates an example process 2400 of accessing and presenting virtual content based on contextual information. The process 2400 may be performed by a wearable device.

At block 2410, the wearable device accesses data acquired by one or more environmental sensors of a wearable device. The acquired data may include data associated with the user or the user's environment.

At block 2420, the wearable device determines contextual information based at least on an analysis of the data acquired by the one or more environmental sensors. The contextual information may include information associated with an HCP, a patient, virtual medical record, an exam or operating room, objects in the exam or operating room, a location of the user of the wearable device, interactions between the user and the patient, etc. In some embodiments, the wearable device can also access data in the remote data repository 280 or the healthcare database system 1220 and determine contextual information based on the accessed data.

At block 2430, the wearable device identifies virtual objects associated with a FOR for a user of the wearable device based at least partly on the contextual information. The virtual objects may include the virtual content shared among users, past test results in a patient's medical record, documentations of interactions between users and the patient, the user's scheduling information, etc. For example, the wearable device can determine a current location of the user and identify the virtual objects associated with the current location.

At block 2440, the wearable device can present one or more of the virtual objects in the user's FOV. For example, when a doctor is at a hospital, the virtual objects associated with the doctor FOR may include the map of the hospital (or a route to a location) and the doctor's schedule of the day. However, the wearable device may present only the doctor's schedule of the day in the FOV. If the doctor wants to view the map of the hospital, the doctor can actuate the user input device 466 or use a pose.

Optionally, the wearable device can determine, based on the contextual information, whether a threshold condition for generating an alert is met at block 2450. The threshold condition may include a mistake in a medical procedure. For example, the wearable device can determine that standard steps of a surgery that is performed on a patient. The standard steps may include processes A, B, and C. The wearable device can monitor the surgeon's actions and detect that the surgeon has skipped the process B. In response to the detection that the process B is missing, the wearable device can determine that the threshold condition is met. As another example, the wearable device can determine that the threshold condition is met when the surgeon's scalpel is less than a threshold distance to the patient's left leg 2204*l* when the operation should be on the patient's right leg 2204*r*.

If the threshold condition is met, at optional block 2460, the wearable device can present an alert to the user of the wearable device. The alert may include a focus indicator or an alert message indicating the mistake, the threshold condition, or a corrective measure of the mistake, etc.

If the threshold condition is not met, the process 2400 goes back to the block 2410.

Examples of Tracking Medical Instruments

An HCP may need to track medical instruments involved in a medical procedure or exam. Instrument tracking can include counting medical instruments involved in a surgery/exam or knowing whether a foreign object (e.g., a medical instrument) enters or exits a sterile region of the patient. Knowing whether a correct medical instrument has been used or whether a medical instrument is at the correct position is very important to avoid medical malpractice and to improve the quality of the medical care. For example, a surgeon may request a certain instrument, but a different one is handed to him by a nurse. As a result, the surgeon may use the wrong instrument on the patient which can cause a medical accident. As another example, a patient may be closed up with foreign objects (such as, e.g., a gauze, a medical rag, a cellphone, etc.) from his operation if instruments are miscounted.

To ameliorate these problems, current techniques include counting (such as, e.g., by a nurse) all instruments that have entered into the operating room and ensure that the instruments (and their locations/functions) have been properly accounted for at the end of surgery. However, instrument tracking in medical procedures is a tedious task for nurses. In addition, current techniques are prone to errors because multiple HCPs (e.g., multiple surgeons, nurses, etc.) may be involved in an operation. It may be difficult to take into account everyone's actions and usages of the medical instruments. Furthermore, the environment of the operating room may be high stress, time sensitive, and exhausting to the HCPs. Therefore, the HCPs may accidently forget some of the medical instruments in the operating room.

To avoid these problems and to improve existing techniques, the wearable device can use one or more environmental sensors to identify medical instruments in a user's environment and determine whether the medical instrument is at the correct position (rather than for example, inside the patient's abdomen after a surgery). The wearable device can also determine whether the correct medical instrument has entered into a sterile field based on the data acquired by one or more sensors.

Examples of Identifying and Tracking a Medical Instrument

A wearable device can use data acquired by one or more environmental sensors alone or in combination with data stored in the remote data repository 280 to identify a foreign object (e.g., a medical instrument) and determine semantic information associated with the foreign object. For example, a wearable device can use the outward-facing imaging system 464 to obtain an image of the user's environment. The object recognizers 708 can detect a medical instrument in the image. The wearable device can also communicate with the remote data repository 280 (or use the local processing data module 260) to determine semantic information associated with the detected medical instrument, such as, for example, a name, a type, a use, a function of the instrument, whether the instrument is in a set of instruments, etc.

The wearable device can also use one or more optical sensors for identifying the medical instrument. For example, a medical instrument may include an optical label such as, e.g., a quick response code (QR) or a barcode. The optical label may be placed on an exterior surface of the medical instrument. The optical label may encode the identity of the medical instrument (such as, e.g., an identifier associated with the medical instrument). The optical label may also encode semantic information associated with the medical instrument. The one or more optical sensors of the wearable device can scan the optical label. The wearable device can parse the information encoded in the optical label. In some embodiments, the wearable device can communicate with a remote data repository 280 to obtain additional information of the optical label. For example, the wearable device can extract an identifier of the medical instrument and communicate with the remote data repository to get the semantic information of the medical instrument. The wearable device may also incorporate or utilize electromagnetic tracking sensors to track the location of objects in the environment.

In addition or in alternative to an optical label, the medical instrument may also have an electromagnetic label, such as, e.g., an RFID tag. The electromagnetic label can emit signals that can be detected by the wearable device. For example, the wearable device may be configured to be able to detect signals with certain frequencies. In some implementations, the wearable device can send a signal to the medical instrument. Based on the feedback received from the medical instrument, the wearable device can identify the medical instrument. The wearable device may communicate with the medical instrument via a wired or a wireless network.

In some embodiments, when the wearable device identifies a medical instrument, the wearable device may provide a focus indicator near the medical instrument. For example, the wearable device can identify a gauze next to the physician and display a green halo around the gauze. The wearable device can assign the focus indicator based on the semantic information of the medical instrument. For example, the wearable device can assign a green halo around the gauze while assigning a blue halo around a scalpel.

The wearable device can track the position of a medical instrument based on the data acquired by one or more environmental sensors. For example, the wearable device can determine the position of the medical instrument overtime based on data acquired by the outward-facing imaging system 464. As an example, the wearable device can identify a scalpel in a tray at time 1 and identify the same scalpel in a surgeon's hand at a later time. Advantageously, in some embodiments, instrument tracking may be achieved based on data collected from multiple wearable devices because each wearable device may have a limited FOV and cannot observe the whole operating room. For example, a scalpel may appear in a tray at time 1 based on an image acquired by the nurse's wearable device. The position of the scalpel may later be updated to be the surgeon's hand based on an image acquired by the surgeon's wearable device even though the nurse's wearable device might not perceive that the surgeon has picked up the scalpel.

Although the examples are described with reference to identifying and tracking medical instruments, similar techniques can also be applied to other physical objects, such as a cellphone, a pen, etc.

Examples of Identifying an Object in a Sterile Region

Figure 25:
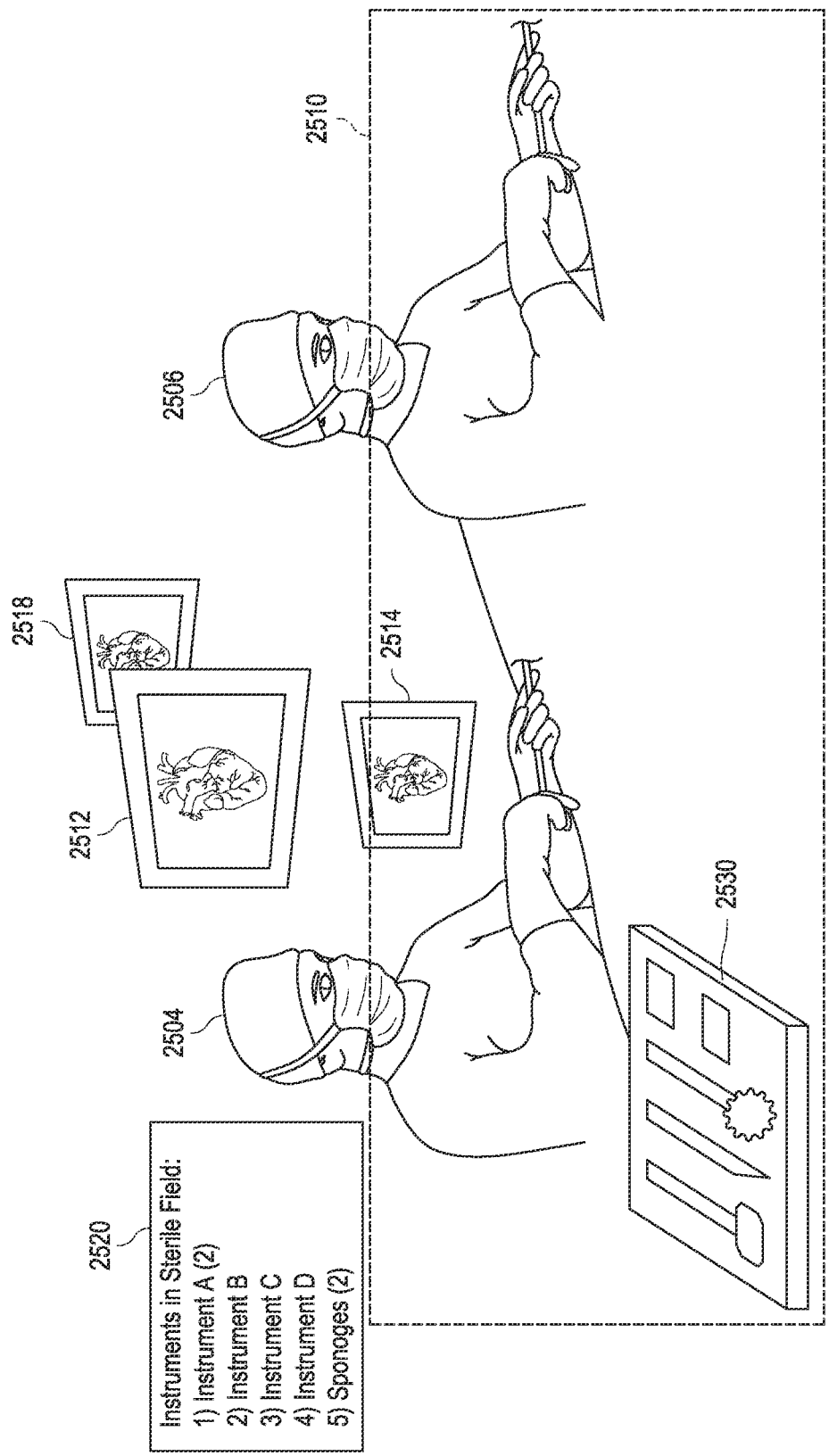
FIG. 25 schematically illustrates an example of a medical procedure occurring in an operating room have a sterile region.

FIG. 25 schematically illustrates an example of a medical procedure occurring in an operating room having a sterile region 2510. In this example, two surgeons 2504 and 2506 are involved in the procedure. The two surgeons may wear their respective wearable devices while performing the surgery.

The sterile region (also referred to as sterile field) 2510 may be a user-defined area in a physical environment or in the user's FOR. The sterile region 2510 may be associated with a region of the patient (or the operating room) that was disinfected prior to the surgery. For example, the sterile region 2510 may be the region that will be or is cut open in a surgery.

The wearable device can present a world map 920 of the operating room to an HCP (such as, e.g., the surgeon 2504, 2506, a nurse, or another HCP). The HCP can mark, on the world map 920 which region in the operating room is the sterile region 2510. In some embodiments, the wearable device can automatically access the patient's virtual medical records or the information associated with the surgery to determine the sterile region. A portion of the sterile region 2510 may overlap with a portion of the surgeon's 2504 FOV or a portion of the surgeon's 2506 FOV.

The surgeon 2504 can perceive virtual objects 2520, 2512, 2514, 2518 as well as medical instruments 2530 in his FOR. In this example, the medical instruments 2530 are also in the sterile region 2510 which may be part of the surgeon's 2504 FOR. The virtual objects 2512, 2514, 2518 may be associated with the patient's virtual medical record, the patient's physiological data (such as heart rate, respiratory rate, etc.), information associated with the surgery (such as, e.g., the steps of the surgeon, an enlarged view of the organ that is being operated on, etc.), and so on. The virtual object 2520 includes a list of medical instruments 2530 in the sterile region 2510. Medical instruments 2530 can include 2 instruments A, 1 instrument B, 1 instrument C, 1 instrument D, and 2 sponges.

The surgeon 2504 can perceive in his FOV at least a subset of the virtual and physical objects in his FOR. For example, while the surgeon 2504 is operating on the patient, the surgeon 2504 can perceive the virtual object 2514 and the two sponges via the 3D user interface of his wearable device. The wearable device can monitor the physical objects in the FOV. For example, the wearable device of the surgeon 2504 can constantly scan for recognized objects in the surgeon's 2504 FOV. The wearable device can also scan for new objects entering into the FOV. For example, during the procedure, the surgeon can bring a scalpel inside the FOV. The wearable device can detect that the scalpel has entered into his FOV. If this scalpel was not previously identified by the wearable device, the wearable device can use computer vision techniques or scan the optical/electromagnetic label associated with the scalpel to recognize that a new object has entered the FOV.

Examples of Confirming a Correct Medical Instrument is Used

The wearable device can confirm whether a medical instrument entering into the sterile region (or an FOV of a HCP) is the correct medical instrument. The wearable device can perform such confirmation based on data acquired by one or more environmental sensors. For example, the wearable device can collect audio data using the microphone 232. The wearable device of an HCP can analyze the audio data to identify a medical instrument mentioned in the audio data. The wearable device can also monitor the objects entering into the HCP's FOV and determine whether the medical instrument entered into the FOV matches the medical instrument identified in the audio data. If the medical instrument entered into the FOV does not match the medical instrument identified in the audio data, the wearable device can provide an alert to the HCP. The alert may be a focus indicator. The focus indicator may be displayed around the non-matching medical instrument entered into the FOV. The alert may also be an alert message which can include a brief description explaining that a non-matching medical instrument has entered into the FOV. For example, the alert may include the name of the non-matching medical instrument and the correct medical instrument requested, and a statement the wrong medical instrument has entered into the FOV. The alert may be presented on the 3D virtual user interface of the wearable device or be presented via the speaker 240 of the wearable device.

As an example, the surgeon 2504 may ask a nurse to hand him a scalpel in a surgery. The nurse, however, hands over a pair of scissors. The wearable device can identify the word "scalpel" using speech recognition and determine that the doctor has requested a scalpel. The wearable device can also detect the pair of scissors handed over by the nurse using computer vision techniques. Because the pair of scissors is not the scalpel requested by the surgeon, the wearable device can provide a red halo around the pair of scissors indicating that the pair of scissors is not the correct medical instrument.

The wearable device can also confirm whether the correct medical instrument has entered into the FOV or the sterile region based on data acquired from the environmental sensors and data accessed from the remote data repository 280 (or data from local processing & data module 260). The remote data repository 280 may include information on a set of surgical instruments that are used in a certain type of surgery. The information on the set of surgical instruments may include the type, name, quantity, position, function, etc., of the surgical instruments used in the type of surgery. Information about the instrument can also be uploaded to the patient chart (e.g., which stent was used, which implant was inserted with part number and manufacturer information, etc.). Such information can be added to the procedure file in the patient's medical records.

The wearable device can determine a type of surgery that will be or is being performed on the patient based on the patient's virtual medical records. The wearable device can identify the set of surgical instruments associated with the type of surgery based on the data stored in the remote data repository 280. The wearable device can also identify the surgical instruments in the sterile region based on the acquired images and determine whether the sterile region includes a surgical instrument that does not belong to the identified set of surgical instrument. During a surgery, the wearable device can continuously monitor the objects entering into (or exiting) the sterile region or FOVs of the respective surgeons 2504, 2506, update the list of surgical instruments on the virtual object 2520, and alert the surgeons 2504, 2506 if a wrong surgical instrument has entered into the sterile region (or the FOVs).

As an example, a set of surgical instruments for an appendectomy may include various scissors, forceps, retractors, gallipots, kidney dishes, towel clamps, etc. The medical instruments 2530 in the sterile region 2510 shown in FIG. 25 may include 2 scissors, one forceps, one retractor, and 1 bone curette. The wearable device can present the list of surgical instruments in the sterile region 2510 as shown by the virtual object 2520. However, the bone curette is not in the set of surgical tools for appendectomy. As a result, the wearable device can provide an alert to the surgeon 2504 indicating that the bone curette has entered the sterile region 2510. For example, the wearable device can show the phrase "bone curette" in a different color on the virtual object 2520. In response to the alert message, the surgeon can remove the bone curette from the sterile region 2510. Once the wearable device observes that the bone curette has been moved to the outside of the sterile region, the wearable device can remove the phrase "bone curette" from the virtual object 2520.

Examples of Tracking and Counting Medical Instruments in the Sterile Region

The wearable device can track the objects entering and exiting the sterile region 2510 using one or more environmental sensors and local processing and data module 260. In some embodiments, the wearable device can also communicate with the remote processing module 270 and the remote data repository 280 to track and count medical instruments.

For example, the wearable device can keep a list of medical instruments in the sterile region 2510. If a wearable device detects that a medical instrument enters into the sterile region, the wearable device can add the medical instrument to the list. If a medical instrument is removed from the sterile region, the wearable device can deduct the removed medical instrument from the list. The wearable device can present a current list of instruments in the sterile region using the virtual object 2520 shown in FIG. 25. In some implementations, the wearable device can display one or more focus indicators showing the medical instrument that is currently being used by the user is in (or out of) the sterile region.

Data associated with tracking the medical instruments may be analyzed to determine whether all the instruments entering into the sterile region have been properly accounted for. For example, the wearable device can determine whether all medical instruments in the sterile region have exited the sterile region. For the medical instruments that did not exit the sterile region, the wearable device can determine whether they should be left within the sterile region. As an example, based on the tracking data, the wearable device may identify that a piece of gauze and a surgical thread are still in the sterile region at the end of the surgery. The wearable device can further determine that the position of the surgical thread is proper because the surgical suture is used to hold body tissues together after the surgery. The position of the piece of gauze, however, is not proper because it should not be left inside of the patient's body after the surgeon closes the patient. As a result, the wearable device may provide an alert to the surgeon 2504 indicating that the piece of gauze is still in the sterile region.

Multiple wearable devices may be used to collectively maintain the accuracy of which medical instruments have entered or exited the sterile region 2510. For example, the remote computing system 1720 (shown in FIG. 17) can maintain a list of instruments in the sterile field (as shown by the virtual object 2520). The remote computing system 1720 can update the list of instruments based on data acquired by the wearable device of the surgeon 2504 and the wearable device of the surgeon 2506. Instrument tracking based on data from multiple wearable devices may be beneficial because multiple users may bring the medical instrument into or out of the sterile field. In addition, the FOV of a user's wearable device may cover only a portion of the sterile region 2510 and may not be able to track every object in the sterile region 2510. Furthermore, when a user may look away from the sterile region 2510 or leaves the operating room, other users that are interacting with the sterile region 2510 can continue to track the medical instruments entering or exiting the sterile region 2510.

Although the examples are described with reference to medical instruments, similar techniques can also be used for identifying, tracking, and confirming other physical objects. For example, the wearable device can identify a cellphone and track the position of the cellphone to make sure that the cellphone is not accidentally left inside of the patient's body. Furthermore, although the examples are described using sterile region, similar techniques can also be used for monitoring and tracking objects other regions, such as, e.g., the operating room or the FOV of an HCP.

Example Processes of Tracking Medical Instruments

Figure 26:
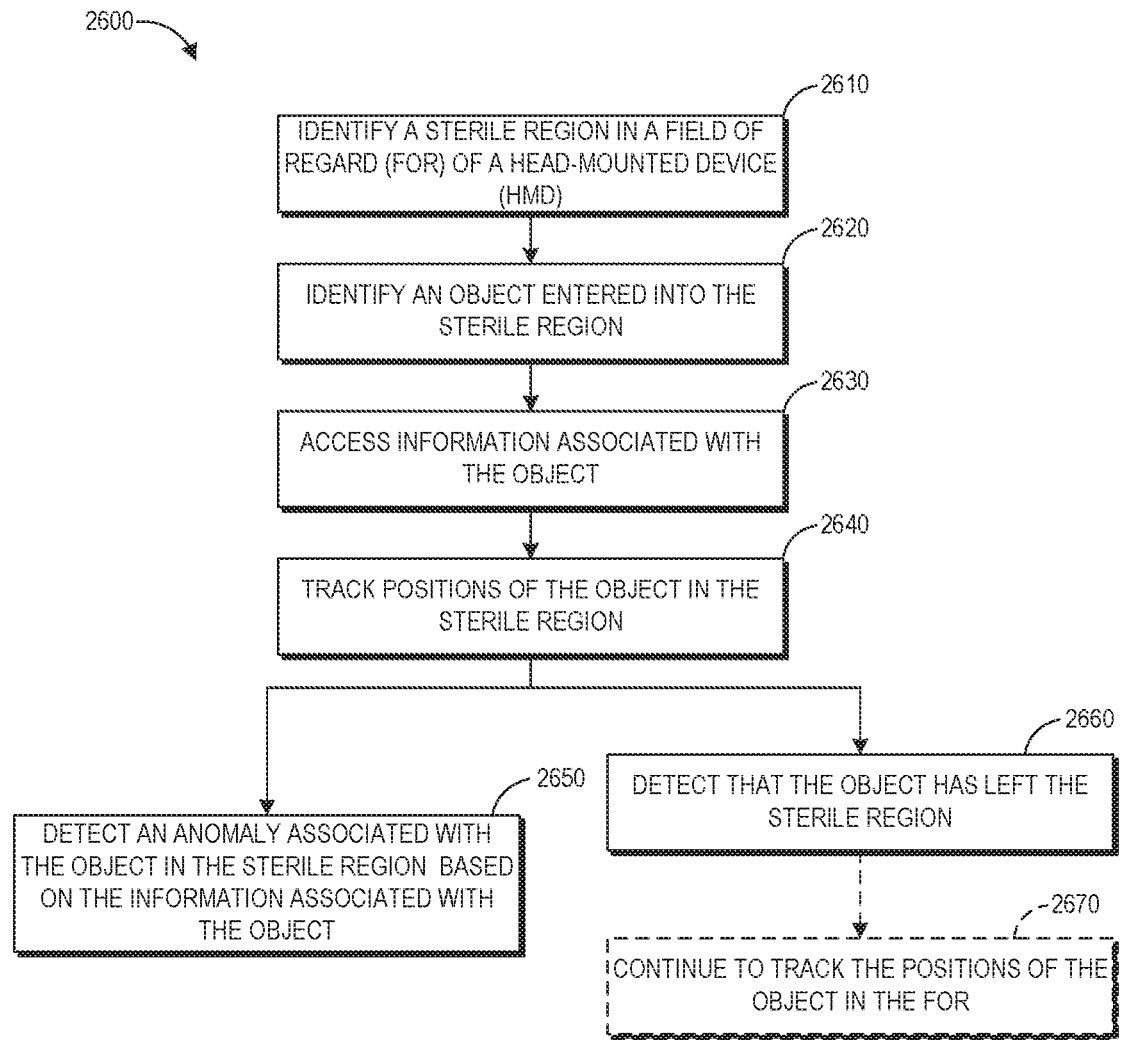
FIG. 26 is a flowchart that illustrates an example process of tracking medical objects in a sterile region.

FIG. 26 is a flowchart that illustrates an example process 2600 of tracking medical objects in a sterile region. The example process 2600 may be performed by the wearable device 210 alone or in combination with the remote computing system 1720. The wearable device 210 may be a wearable device.

At block 2610, wearable device identifies a sterile region in a FOR associated with the wearable device. The sterile region can be determined based on data obtained from an external database, such as, e.g., the database system 1220 or the remote data repository 280. For example, the sterile region may be determined based on the hospital protocols associated with an operating room, the type of surgery performed on the patient, the patient's body, etc. The sterile region can also be marked by an HCP.

At block 2620, the wearable device can identify an object entered into the sterile region. The wearable device can use data acquired from one or more environmental sensors to identify the object For example, the wearable device can detect the object using computer vision algorithms or scan an optical label associated with the object.

At block 2630, the wearable device can access information associated with the object. The wearable device can communicate with the remote data repository 280 or the healthcare database management system 1220 to determine semantic information associated with the object. For example, the information associated with the object may include the name of the object, the type of the object, the position of the object, etc.

At block 2640, the wearable device can track the positions of the object in the sterile region. For example, the wearable device can use computer vision algorithm to detect that a scalpel has been moved from a tray to a surgeon's hand.

The wearable device can keep a record of all the objects entering into the sterile region and exiting the sterile region. For example, the wearable device can maintain a list of objects that are currently in the sterile region. At block 2650, the wearable device can detect an anomaly associated with the object in the sterile region. The wearable device can make the detection based on the information associated with the object or information associated with the medical procedure (such as the type of the surgery, surgical instruments required for the surgery, etc.) For example, the wearable device can determine whether the sterile region includes a medical instrument that is unrelated to the surgery being performed by the user of the wearable device. The wearable device can also determine whether the user of the wearable device has received a surgical instrument which was not requested.

Additionally or alternatively, at block 2660, the wearable device can detect that the object has left the sterile region. For example, the wearable device can detect instruments A, B, and C in a first image of the sterile region. However, in the second image of the sterile region, the wearable device only detects instruments B and C. Accordingly, the wearable device can determine that the instrument A has left the sterile region and remove the instrument A from the list of objects that are currently in the sterile region.

Optionally, at block 2670, the wearable device can continue to track the position of the object in the FOR of the wearable device even though the object has left the sterile region. For example, the wearable device can determine whether a needle has been properly disposed by tracking the position of the needle.

ADDITIONAL ASPECTS

In a 1st aspect, a wearable device configured to present virtual healthcare content to a wearer, the wearable device comprising: a display configured to present virtual content to the wearer, at least a portion of the display being transparent and disposed at a location in front of a wearer's eye when the wearer wears the wearable device such that the transparent portion transmits light from a portion of the environment in front of the wearer to the wearer's eye to provide a view of the portion of the environment in front of the wearer; and a hardware processor in communication with the display, the hardware processor programmed to: receive an access privilege associated with at least a portion of a patient medical record for a patient; access, based at least in part on the access privilege, the at least a portion of the patient medical record; and instruct the display to present to the wearer virtual content relating to the at least a portion of the patient medical record.

In a 2nd aspect, the wearable device of aspect 1, wherein the wearable device comprises an inward-facing imaging system configured to capture an eye image an eye of the wearer, and the processor is programmed to: analyze the eye image to determine a biometric identification element; and receive a confirmation that the biometric identification element matches an authorized biometric identification element for the wearer.

In a 3rd aspect, the wearable device of aspect 2, wherein the biometric identification element comprises an iris scan or a retinal scan.

In a 4th aspect, the wearable device of any one of aspects 1-3, wherein the wearable device further comprises a sensor to determine a location of the wearer, and the access privilege is based at least partly on the location of the wearer.

In a 5th aspect, the wearable device of any one of aspects 1-4, wherein the wearable device further comprises an environmental sensor, and the hardware processor is programmed to: obtain environmental data from the environmental sensor; recognize a data capture trigger from the obtained environmental data; and initiate data capture from at least one data capture element disposed on the wearable device.

In a 6th aspect, the wearable device of aspect 5, wherein the environmental sensor comprises a microphone, the environmental data comprises an audio recording, and the data capture trigger comprises a spoken initiation command.

In a 7th aspect, the wearable device of aspect 5 or aspect 6, wherein the environmental sensor comprises an outward-facing imaging system, the environmental data comprises images of the environment, and the data capture trigger comprises a gesture made by the wearer.

In an 8th aspect, the wearable device of any one of aspects 5-7, wherein the hardware processor is programmed to recognize a data termination trigger from the obtained environmental data and terminate data capture from the at least one data capture element.

In a 9th aspect, the wearable device of any one of aspects 5-8, wherein the data capture element comprises a microphone or an outward-facing imaging system.

In a 10th aspect, the wearable device of any one of aspects 1-9, wherein the hardware processor is programmed to: display a virtual user interface to the wearer, the virtual user interface comprising functionality to permit the wearer to:

input data to the at least a portion of the patient medical record; update the at least a portion of the patient medical record; organize the at least a portion of the patient medical record; or save changes to the at least a portion of the patient medical record.

In an 11th aspect, the wearable device of any one of aspects 1-10, wherein the hardware processor is programmed to communicate the at least a portion of the patient medical record to a data store.

In a 12th aspect, the wearable device of aspect 11, wherein the data store is external to the wearable device, and the communication is over a wireless network.

In a 13th aspect, a healthcare computing environment comprising: the wearable device of any one of aspects 1-12; a healthcare database system comprising: a network interface configured to communicate with the wearable device; non-transitory data storage configured to store the patient medical record.

In a 14th aspect, The healthcare computing environment of aspect 13, wherein the wearable device is configured to be worn by the patient, the environment further comprising: a healthcare provider (HCP) wearable device that comprises: a second display configured to present virtual content to the HCP, at least a portion of the display being transparent and disposed at a location in front of a HCP's eye when the HCP wears the HCP wearable device such that the transparent portion transmits light from a portion of the environment in front of the HCP to the HCP's eye to provide a view of the portion of the environment in front of the HCP; an environmental sensor; and a second hardware processor in communication with the second display, the second hardware processor programmed to include: an object recognizer configured to analyze data from the environmental sensor; and a data management system configured to permit the HCP to access the at least a portion of the patient medical record.

In a 15th aspect, the wearable device of any one of aspects 1-14, wherein the access privilege comprises a read privilege or an edit privilege.

In a 16th aspect, the wearable device of any one of aspects 1-15, wherein the hardware processor is programmed to store attempts to access the at least a portion of the patient medical record in an access log.

In a 17th aspect, the wearable device of any one of aspects 1-16, wherein the hardware processor is programmed to verify an identity of the wearer.

In an 18th aspect, the wearable device of aspect 17, wherein, to verify the identity of the wearer, the hardware processor is programmed to utilize an iris code or a retinal scan.

In a 19th aspect, The wearable device of any one of aspects 17 or 18, wherein, in response to the identity of the wearer not being verified, the hardware processor is programmed to deny access to the at least a portion of the patient medical record.

In a 20th aspect, the wearable device of any one of aspects 17-19, wherein, in response to the identity of the wearer not being verified, the hardware processor is programmed to cease display of the portion of the patient medical record.

In a 21st aspect, a method of monitoring a user's environment in a healthcare setting, the method comprising: under control of a wearable device comprising a display configured to present virtual content to the user of the wearable device, an environmental sensor, and a hardware processor in communication with the display and the environmental sensor: analyzing data acquired by the environmental sensor to detect an initiation condition; determining that the initiation condition is present; documenting a healthcare event using the environmental sensor to provide healthcare documentation; analyzing the data acquired by the environmental sensor to detect a termination condition; determining that the termination condition is present; and ceasing the documentation of the healthcare event using the environmental sensor.

In a 22nd aspect, the method of aspect 21, wherein the environmental sensor comprises a microphone or an outward-facing imaging system.

In a 23rd aspect, the method of claim 21 or claim 22, wherein the environmental sensor comprises a first environmental sensor and a second environmental sensor that is different from the first environmental sensor, and analyzing the data acquired by the environmental sensor to detect an initiation condition comprises analyzing data acquired by the first environmental sensor; and documenting the healthcare event using the environmental sensor comprises documenting the healthcare event using the second environmental sensor.

In a 24th aspect, the method of any one of aspects 21-23, wherein the environmental sensor comprises an outward-facing imaging system, and documenting the healthcare event comprises capturing a video record of the healthcare event.

In a 25th aspect, the method of any one of aspects 21-24, wherein the environmental sensor comprises a microphone, and documenting the healthcare event comprises capturing an audio record of the healthcare event.

In a 26th aspect, the method of aspect 25, wherein documenting the healthcare event comprises: analyzing the audio recording to determine information spoken by a patient about a patient condition.

In a 27th aspect, the method of any one of aspects 21-26, further comprising communicating at least a portion of the healthcare documentation to a data store.

In a 28th aspect, the method of any one of aspects 21-27, further comprising updating a patient medical record to include at least a portion of the healthcare documentation.

In a 29th aspect, a wearable device configured to present virtual healthcare content to a wearer, the wearable device comprising: a display configured to present virtual content to the wearer, at least a portion of the display being transparent and disposed at a location in front of a wearer's eye when the wearer wears the wearable device such that the transparent portion transmits light from a portion of the environment in front of the wearer to the wearer's eye to provide a view of the portion of the environment in front of the wearer; and a hardware processor in communication with the display, the hardware processor programmed to: detect a triggering event for sharing virtual healthcare content with a second wearable device; verify the second wearable device has an access privilege sufficient to present the virtual healthcare content; if the second wearable device has sufficient access privilege, share the virtual healthcare content with the second wearable device; and if the second wearable device has insufficient access privilege, present an indication to the wearer that the second wearable device has insufficient access privilege.

In a 30th aspect, the wearable device of aspect 29, wherein the hardware processor is programmed to: receive a modification of the virtual healthcare content made by the second wearable device; and present the modified virtual healthcare content to the wearer of the wearable device.

In a 31st aspect, the wearable device of aspect 29 or 30, wherein the virtual healthcare content comprises a patient medical record.

In a 32nd aspect, the wearable device of any one of aspects 29-31, wherein the virtual healthcare content comprises information obtained from a medical device.

In a 33rd aspect, the wearable device of any one of aspects 29-32, wherein the virtual healthcare content comprises an image of a portion of a patient.

In a 34th aspect, the wearable device of any one of aspects 29-33, wherein the hardware processor is programmed to accept wearer input to modify the virtual healthcare content.

In a 35th aspect, a wearable device configured to present virtual healthcare content to a wearer, the wearable device comprising: a display configured to present virtual content to the wearer, at least a portion of the display being transparent and disposed at a location in front of a wearer's eye when the wearer wears the wearable device such that the transparent portion transmits light from a portion of the environment in front of the wearer to the wearer's eye to provide a view of the portion of the environment in front of the wearer; an environmental sensor configured to obtain environmental data about an environment of the wearer; and a hardware processor in communication with the display and the environmental sensor, the hardware processor programmed to: access the environmental data obtained by the environmental sensor; determine contextual information based at least partly on the environmental data; identify a virtual object associated with a field of view (FOV) of the wearer of the wearable device based at least partly on the contextual information; and present virtual content relating to the virtual object in the FOV of the wearer of the wearable device.

In a 36th aspect, the wearable device of aspect 35, wherein the environmental sensor comprises a microphone, an outward-facing imaging system, an inward-facing eye-tracking system, a bar code reader, or a GPS sensor.

In a 37th aspect, the wearable device of aspect 35 or aspect 36, wherein the contextual information comprises a location of the wearer, a pose of the wearer, an emotional state of the wearer, a level of access privileges, a symptom or a condition of a patient in the FOV of the wearer, or an identity of a patient in the FOV of the wearer.

In a 38th aspect, the wearable device of any one of aspects 35-37, wherein the contextual information comprises information associated with a physical object in the wearer's environment or a virtual object presented to the wearer.

In a 39th aspect, the wearable device of any one of aspects 35-38, wherein the environmental sensor comprises an imaging system, and to determine the contextual information the hardware processor is programmed to analyze images captured by the imaging system using a computer vision algorithm, a facial recognition algorithm, or a neural network.

In a 40th aspect, the wearable device of any one of aspects 35-39, wherein the virtual content comprises a portion of a patient medical record, an alert, a focus indicator, or a message.

In a 41st aspect, the wearable device of any one of aspects 35-40, wherein the hardware processor is programmed to: determine whether the contextual information passes a threshold condition; if the threshold condition is passed, display updated virtual content to the wearer of the wearable device.

In a 42nd aspect, the wearable device of any one of aspects 35-41, wherein: the contextual information comprises information about medical instruments used during a medical procedure on a patient, and the virtual content comprises information relating to location of the medical instruments.

In a 43rd aspect, the wearable device of aspect 42, wherein the virtual content further comprises an alert indicating that a medical instrument remains in the body of the patient.

In a 44th aspect, the wearable device of aspect 42 or aspect 43, wherein the virtual content comprises an alert that a medical instrument in the FOV of the wearer is inappropriate or unrequested for the medical procedure.

In a 45th aspect, the wearable device of any one of aspects 35-44, wherein the contextual information comprises information about a patient body part.

In a 46th aspect, the wearable device of aspect 45, wherein the virtual content comprises a virtual flag associated with the patient body part.

In a 47th aspect, the wearable device of any one of aspects 35-46, wherein the hardware processor is further programmed to communicate the virtual content to a data repository.

In a 48th aspect, the wearable device of any one of aspects 35-47, wherein the hardware processor is further programmed to update a patient medical record with the virtual content.

In a 49th aspect, a wearable device configured to present virtual healthcare content to a wearer, the wearable device comprising: a display configured to present virtual content to the wearer, at least a portion of the display being transparent and disposed at a location in front of a wearer's eye when the wearer wears the wearable device such that the transparent portion transmits light from a portion of the environment in front of the wearer to the wearer's eye to provide a view of the portion of the environment in front of the wearer; an environmental sensor configured to obtain environmental data about an environment of the wearer; and a hardware processor in communication with the display and the environmental sensor, the hardware processor programmed to: identify a sterile region in a field of regard (FOR) of the wearable device; identify an object entered into the sterile region; access information associated with the object; and track a position of the object in the sterile region.

In a 50th aspect, the wearable device of aspect 49, wherein the hardware processor is further programmed to detect an anomaly associated with the object in the sterile region based at least partly on the information associated with the object.

In a 51st aspect, the wearable device of aspect 50, wherein the hardware processor is programmed to present an alert to the wearer based at least partly upon the detection of the anomaly.

In a 52nd aspect, the wearable device of any one of aspects 49-51, wherein the hardware processor is programmed to detect that the object has left the sterile region.

In a 53rd aspect, the wearable device of any one of aspects 49-52, wherein the hardware processor is programmed to present to the wearer virtual content associated with the object.

In a 54th aspect, the wearable device of aspect 53, wherein the virtual content comprises a list of objects present in the sterile region.

In a 55th aspect, the wearable device of aspect 54, wherein the list further includes positions of the objects.

In a 56th aspect, the wearable device of any one of aspects 49-55, wherein the environmental sensor comprises a microphone, an outward-facing imaging system, a bar code reader, or an electromagnetic tracking system.

In a 57th aspect, a wearable system for managing medical information, the wearable system comprising: a head-mounted display (HMD) comprising a display configured to present virtual content to a user; one or more environmental sensors configured to obtain data associated with the user's environment; a hardware processor in communication with the display and the one or more environmental sensors, and programmed to: monitor the user's environment via the one or more environmental sensors; detect an initiation condition based at least partly on first data acquired by the one or more environmental sensors; document at least a portion of an interaction with a patient via an environmental sensor in response to the detection of the initiation condition, wherein the portion of the interaction comprises second data acquired by the environmental sensor; analyze the second data to extract relevant medical information related to the interaction with the patient based on contextual information; and initiate storage of the relevant medical information to a healthcare database system.

In a 58th aspect, the wearable system of aspect 57, wherein the one or more environmental sensors comprise at least an outward-facing camera or a microphone.

In a 59th aspect, the wearable system of aspect 57 or 58, wherein to analyze the second data to extract relevant medical information, the hardware processor is programmed to: determine an audio stream spoken by the patient or the user of the wearable system; convert the audio stream to a text; and parse the text to identify phrases describing the patient's medical condition or history.

In a 60th aspect, the wearable system of any one of aspects 57-59, wherein to initiate storage of the relevant medical information, the hardware processor is programmed to: verify the patient's identity based at least partly on the data acquired by the one or more environmental sensor; and update a medical record stored in the healthcare database with the relevant medical information captured from the interaction between the patient and the user.

In a 61 st aspect, the wearable system of any one of aspects 57-60, wherein the hardware processor is further programmed to: detect a triggering event for sharing healthcare information with a second wearable system; determine an access privilege associated with the second wearable system; and cause at least a portion of the healthcare information to be communicated to the second wearable system in response to a determination that the second wearable system has the access privilege.

In a 62nd aspect, the wearable system of aspect 61, the hardware processor is programmed to provide an indication to the second wearable system in response to a determination that the second wearable system has insufficient access privilege.

In a 63rd aspect, the wearable system of aspect 61 or 62, wherein the access privilege associated with the second wearable system is configured by the patient.

In a 64th aspect, the wearable system of any one of aspects 61-63, wherein the healthcare information comprises at least a portion of a field of view (FOV) of the user as captured by an outward-facing camera.

In a 65th aspect, the wearable system of any one of aspects 61-64, wherein the hardware processor is programmed to share the healthcare information and an annotation associated with the healthcare information with the second wearable system.

In a 66th aspect, the wearable system of any one of aspects 57-65, wherein the contextual information comprises at least one of a location of the user, a pose of the user, a level of access privilege of the user, a symptom or a condition of the patient in the FOV of the user, or an identity of the patient in the FOV of the user.

In a 67th aspect, the wearable system of any one of aspects 57-66, wherein the hardware processor is further programmed to cause the head-mounted display to present virtual content to the user related to the interaction with the patient.

In a 68th aspect, the wearable system of aspect 67, wherein the virtual content comprises at least one of a portion of a patient medical record or information related to the patient's physiological parameters received from a medical device.

In a 69th aspect, the wearable system of aspect 67 or 68, wherein the contextual information comprises information about medical instruments used during a medical procedure on a patient, and the virtual content comprises information relating to location of the medical instruments.

In a 70th aspect, the wearable system of aspect 69, wherein the virtual content comprises an alert that a medical instrument in the FOV of the user is inappropriate or unrequested for a medical procedure.

In a 71st aspect. a method for managing medical information, the method comprising: under control of a hardware processor: monitoring a user's environment based on data acquired by a wearable device comprising an environmental sensor; detecting an initiation condition based at least partly on first data acquired by the wearable device; documenting an interaction between a patient and a healthcare provider (HCP) via the environmental sensor of the wearable device in response to the detection of the initiation condition, wherein the interaction comprises second data acquired by the environmental sensor; analyzing the second data to extract relevant medical information related to the interaction with the patient based on contextual information; and initiating storage of the relevant medical information to a healthcare database system.

In a 72nd aspect, the method of aspect 71, wherein the environmental sensor comprises a microphone, and analyzing the second data to extract relevant medical information comprises: acquiring, via the microphone, an audio stream spoken by the patient or the HCP; converting the audio stream to a text; and parsing the text to identify phrases describing the patient's medical condition or history.

In a 73rd aspect, the method of aspect 71 or 72, wherein initiating storage of the relevant medical information comprises: verifying the patient's identity based at least partly on the data acquired by the wearable device; and updating a medical record stored in the healthcare database with the relevant medical information captured from the interaction between the patient and the HCP.

In a 74th aspect, the method of any one of aspects 71-73, further comprising: detecting a triggering event for sharing healthcare information with a second wearable device; determining an access privilege associated with the second wearable device; and causing at least a portion of the healthcare information to be communicated to the second wearable device in response to a determination that the second wearable device has the access privilege.

In a 75th aspect, the method of aspect 74, wherein the access privilege associated with the second wearable device is configured by the patient.

In a 76th aspect, the method of aspect 74 or 75, wherein the healthcare information comprises at least a portion of a field of view (FOV) of the user as captured by an outward-facing imaging system.

In a 77th aspect, the method of aspect 76, further comprising sharing the healthcare information and an annotation associated with the healthcare information with the second wearable system.

In a 78th aspect, the method of any one of aspects 71-77, wherein the contextual information comprises at least one of a location of the user, a pose of the user, a level of access privilege of the user, a symptom or a condition of the patient in the FOV of the user, or an identity of the patient in the FOV of the user.

In a 79th aspect, the method of any one of aspects 71-78, further comprising causing the wearable device to display, via a head-mounted display, virtual content comprising at least one of a portion of a patient medical record or information related to the patient's physiological parameters received from a medical device.

In an 80th aspect, the method of aspect 79, wherein the virtual content comprises an alert that a medical instrument in the FOV of the user is inappropriate or unrequested for a medical procedure.

In an 81st aspect, a first wearable device for managing medical information, the first wearable device comprising: an outward-facing imaging system configured image an environment of a user; a head-mounted display configured to present virtual content to the user; and a hardware processor programmed to: monitor objects in a user's environment via data received from the outward-facing imaging system; determine objects in the user's field of view as perceived through the head-mounted display; detect a triggering event for a sharing session with a second wearable device, wherein the sharing session comprises sharing at least first information associated with a first physical object in the user's field of view with a second wearable device, wherein the first information is outside of a field of view of the second wearable device; communicate the first information to the second wearable device; receive virtual content from the second wearable device wherein the virtual content comprises second information associated with a second physical object which is outside of the user's field of view; and present the virtual content received from the second wearable device to the user via the head-mounted display.

In an 82nd aspect, the first wearable device of aspect 81, wherein the hardware processor is further programmed to: receive an annotation associated with the first physical object in the user's field of view via the first wearable device, and wherein to communicate the first information to the second wearable device, the hardware processor is programmed to communicate the annotation and an image of the first object to the second wearable device.

In an 83rd aspect, the first wearable device of aspect 82, wherein the annotation comprises one or more virtual flags placed on a portion of a patient's body part, wherein the one or more virtual flags indicate an orientation of the portion of the patient's body part.

In an 84th aspect, the first wearable device of any one of aspects 81-83, wherein the sharing session is part of an interaction between the user and a patient, and the hardware processor is further programmed to: document at least a portion of the interaction between the user and the patient using at least one of the outward-facing imaging system or a microphone; identify relevant medical information from the interaction; and update a medical record of the patient with the relevant medical information.

In an 85th aspect, a method for managing medical information, the method comprising: under control of a first wearable device comprising an outward-facing imaging system, a hardware processor, and a head-mounted display: monitoring objects in a user's environment via the outward-facing imaging system; determining objects in the user's field of view as perceived through the head-mounted display; detecting a triggering event for a sharing session with a second wearable device, wherein the sharing session comprises sharing at least first information associated with a first physical object in the user's field of view with a second wearable device, wherein the first information is outside of a field of view of the second wearable device; communicating the first information to the second wearable device; receiving virtual content from the second wearable device wherein the virtual content comprises second information associated with a second physical object which is outside of the user's field of view; and presenting the virtual content received from the second wearable device to the user via the head-mounted display.

In an 86th aspect, the method of aspect 85, further comprising: receiving an annotation associated with the first physical object in the user's field of view via the first wearable device, and wherein communicating the first information to the second wearable device comprises communicating the annotation and an image of the first object to the second wearable device.

In an 87th aspect, the method of aspect 86, wherein the annotation comprises one or more virtual flags placed on a portion of a patient's body part, wherein the one or more virtual flags indicate an orientation of the portion of the patient's body part, an orientation of a camera that captured the image, or contextual information associated with the image or the portion of the patient's body part.

In an 88th aspect, the method of any one of aspects 85-87, wherein the sharing session is part of an interaction between the user and a patient and the method further comprises: documenting the interaction between the user and the patient using at least one of the outward-facing imaging system or a microphone; identifying relevant medical information from the interaction; and updating a medical record of the patient with the relevant medical information.

In an 89th aspect, the method of any one of aspects 85-88, further comprising: verifying an access privilege of the second wearable device; and sharing at least a portion of the first information to which the access privilege of the second wearable device is sufficient.

In a 90th aspect, the method of aspect 89, wherein the access privilege is managed by a patient whose medical information is being shared between the first wearable device and the second wearable device.

In a 91st aspect, a wearable device comprising: an outward-facing camera configured to image a field of regard (FOR) of a user, the FOR comprising a portion of the environment around the user that is capable of being perceived by the user via the wearable device; a head-mounted display configured to present virtual content to the user, wherein at least a portion of the display is transparent such that the transparent portion transmits light from a portion of the environment in front of the wearer to the wearer's eye to provide a view of the portion of the environment in front of the wearer; a hardware processor in communication with the display and the environmental sensor, the hardware processor programmed to: determine a sterile region in the FOR, wherein the sterile region comprises an area that is disinfected prior to a medical procedure; analyze data acquired by the outward-facing camera to identify a physical object entered into the sterile region; access information associated with the physical object; track a position of the physical object in the sterile region via the data acquired by the outward-facing camera; and cause the head-mounted display to present virtual content associated with the medical procedure.

In a 92nd aspect, the wearable device of aspect 91, wherein the sterile region comprises at least a portion of the patient's body.

In a 93rd aspect, the wearable device of aspect 91 or 92, wherein a boundary of the sterile region is delineated by a user of the wearable device via hand gestures.

In a 94th aspect, the wearable device of any one of aspects 91-93, wherein the information associated with the physical object comprises at least one of a function of the physical object or a type of the medical procedure.

In a 95th aspect, the wearable device of any one of aspects 91-94, wherein the hardware processor is further programmed to detect an anomaly associated with the physical object in the sterile region based at least partly on the information associated with the physical object.

In a 96th aspect, the wearable device of aspect 95, wherein the detected anomaly comprises a determination that the physical object is unrequested or inappropriate for the medical procedure, and wherein the hardware processor is programmed to present an alert to the wearer based at least partly upon the detected anomaly.

In a 97th aspect, the wearable device of any one of aspects 91-96, wherein the hardware processor is further programmed to determine whether the physical object has left the sterile region.

In a 98th aspect, the wearable device of any one of aspects 91-97, wherein the virtual content associated with the medical procedure comprises a list of medical instructions for the medical procedure.

In a 99th aspect, the wearable device of any one of aspects 91-98, wherein the virtual content further comprises a focus indicator indicating one or more medical instructions that are in the sterile region based at least partly on the tracking of the physical object.

In a 100th aspect, a method comprising: under control of a hardware processor: determining a sterile region in a field of regard (FOR) of a user of a wearable device, wherein the FOR comprising a portion of the environment around the user that is capable of being perceived by the user via the wearable device; analyzing data acquired by an outward-facing camera of the wearable device to identify a physical object entered into the sterile region; accessing information associated with the physical object; tracking a position of the physical object in the sterile region based on the data acquired by the outward-facing camera; and causing a visual indication to be provided by a head-mounted display of the wearable device, where the visual indication is associated with the position of the physical object.

In a 101st aspect, the method of aspect 100, wherein the sterile region comprises at least a portion of the patient's body.

In a 102nd aspect, the method of aspect 100 or 101, wherein the information associated with the physical object comprises at least one of a function of the physical object or a type of the medical procedure.

In a 103rd aspect, the method of any one of aspects 100-102, further comprising detecting an anomaly associated with the physical object in the sterile region based at least partly on the information associated with the physical object.

In a 104th aspect, the method of any one of aspects 100-103, wherein the detected anomaly comprises a determination that the physical object is unrequested or inappropriate for the medical procedure, and the method further comprises presenting an alert to the wearer based at least partly upon the detected anomaly.

In a 105th aspect, the method of any one of aspects 100-104, further comprising: determining whether the physical object has left the sterile region; and in response to a determination that the physical object has left the sterile region, decrease a count associated with the physical object, wherein the count represents a number of the physical object that is in the sterile region.

In a 106th aspect, the method of any one of aspects 100-105, wherein the virtual indication comprises a list of physical objects in the sterile region.

Additional Considerations

Each of the processes, methods, and algorithms described herein and/or depicted in the attached figures may be embodied in, and fully or partially automated by, code modules executed by one or more physical computing systems, hardware computer processors, application-specific circuitry, and/or electronic hardware configured to execute specific and particular computer instructions. For example, computing systems can include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some implementations, particular operations and methods may be performed by circuitry that is specific to a given function.

Further, certain implementations of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities can be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto can be performed in other sequences that are appropriate, for example, in serial, in parallel, or in some other manner. Tasks or events may be added to or removed from the disclosed example embodiments. Moreover, the separation of various system components in the implementations described herein is for illustrative purposes and should not be understood as requiring such separation in all implementations. It should be understood that the described program components, methods, and systems can generally be integrated together in a single computer product or packaged into multiple computer products. Many implementation variations are possible.

The processes, methods, and systems may be implemented in a network (or distributed) computing environment. Network environments include enterprise-wide computer networks, intranets, local area networks (LAN), wide area networks (WAN), personal area networks (PAN), cloud computing networks, crowd-sourced computing networks, the Internet, and the World Wide Web. The network may be a wired or a wireless network or any other type of communication network.

The systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure. Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. No single feature or group of features is necessary or indispensable to each and every embodiment.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted can be incorporated in the example methods and processes that are schematically illustrated. For example, one or more additional operations can be performed before, after, simultaneously, or between any of the illustrated operations. Additionally, the operations may be rearranged or reordered in other implementations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A wearable system for managing medical information, the wearable system comprising:
    a head-mounted display (HMD) comprising a display configured to present virtual content to a user;
    one or more environmental sensors configured to obtain data associated with the user's environment;
    a hardware processor in communication with the display and the one or more environmental sensors, and programmed to:
        monitor the user's environment via the one or more environmental sensors;
        detect an initiation condition based at least partly on first data acquired by the one or more environmental sensors;
        document at least a portion of an interaction with a patient via an environmental sensor in response to the detection of the initiation condition, wherein the portion of the interaction comprises second data acquired by the one or more environmental sensors;

analyze the second data to extract relevant medical information related to the interaction with the patient based on contextual information; and initiate storage of the relevant medical information to a healthcare database system, wherein the display of the HMD is configured to present the virtual content with varying amounts of light ray divergence corresponding to a plurality of different depth planes, wherein the hardware processor is further programmed to:
identify a medical instrument mentioned in audio data obtained from the one or more environmental sensors, wherein the audio data is associated with the interaction with the patient, and cause the HMD to present the virtual content to indicate a physical object in a field of view (FOV) of the user as perceived through the HMD based on whether the physical object in the FOV of the user matches the medical instrument identified in the audio data, wherein the virtual content comprises an alert based on determining that the physical object in the FOV of the user does not match the medical instrument identified in the audio data.

2. The wearable system of claim 1, wherein the one or more environmental sensors comprise at least an outward-facing camera or a microphone.

3. The wearable system of claim 1, wherein to analyze the second data to extract the relevant medical information, the hardware processor is programmed to:
determine an audio stream spoken by the patient or the user of the wearable system, wherein the audio data is included in the audio stream;
convert the audio stream to a text; and
parse the text to identify phrases describing the patient's medical condition or history.

4. The wearable system of claim 1, wherein to initiate storage of the relevant medical information, the hardware processor is programmed to:
verify the patient's identity based at least partly on at least one of the first data or the second data acquired by the one or more environmental sensors; and
update a medical record stored in the healthcare database system with the relevant medical information captured from the interaction between the patient and the user.

5. The wearable system of claim 1, wherein the hardware processor is further programmed to:
detect a triggering event for sharing healthcare information with a second wearable system;
determine an access privilege associated with the second wearable system; and
cause at least a portion of the healthcare information to be communicated to the second wearable system in response to a determination that the second wearable system has the access privilege.

6. The wearable system of claim 5, wherein the hardware processor is further programmed to provide an indication to the second wearable system in response to a determination that the second wearable system has insufficient access privilege.

7. The wearable system of claim 5, wherein the access privilege associated with the second wearable system is configured by the patient.

8. The wearable system of claim 5, wherein the healthcare information comprises at least a portion of the FOV of the user as captured by an outward-facing camera.

9. The wearable system of claim 5, wherein the hardware processor is further programmed to share the healthcare information and an annotation associated with the healthcare information with the second wearable system.

10. The wearable system of claim 1, wherein the contextual information comprises at least one of a location of the user, a pose of the user, a level of access privilege of the user, a symptom or a condition of the patient in the FOV of the user, or an identity of the patient in the FOV of the user.

11. The wearable system of claim 1, wherein the hardware processor is further programmed to cause the HMD to present second virtual content to the user related to the interaction with the patient.

12. The wearable system of claim 11, wherein the second virtual content comprises at least one of a portion of a patient medical record or information related to the patient's physiological parameters received from a medical device.

13. The wearable system of claim 11, wherein the contextual information comprises information about one or more medical instruments used during a medical procedure on a patient, and wherein the second virtual content comprises information relating to location of the one or more medical instruments.

14. The wearable system of claim 13, wherein the second virtual content comprises an alert that the medical instrument in the FOV of the user is inappropriate or unrequested for a medical procedure.

15. A method for managing medical information, the method comprising:
under control of a first wearable device comprising an outward-facing imaging system, a hardware processor, and a head-mounted display (HMD):
monitoring physical objects in a user's environment via the outward-facing imaging system;
determining physical objects in the user's field of view (FOV) as perceived through the HMD;
detecting a triggering event for a sharing session with a second wearable device, wherein the sharing session comprises sharing at least first information associated with a first physical object in the user's FOV with a second wearable device, wherein the first physical object is outside of a FOV of the second wearable device;
communicating the first information to the second wearable device;
receiving virtual content from the second wearable device, wherein the virtual content comprises second information associated with a second physical object which is outside of the user's FOV; and
presenting the virtual content received from the second wearable device to the user via the HMD, wherein the HMD is configured to present the virtual content with varying amounts of light ray divergence corresponding to a plurality of different depth planes,
wherein the method further comprises, under control of the first wearable device:
identifying a medical instrument mentioned in audio data obtained from a microphone during an interaction between the user and a patient, wherein the audio data is associated with the interaction with the patient, and
presenting the virtual content to indicate the first physical object in the user's FOV, as perceived through the HMD, based on whether the first physical object matches the medical instrument identified in the audio data, wherein the virtual content comprises an alert based on determining that the first physical object in the FOV of the user does not match the medical instrument identified in the audio data.

16. The method of claim 15, further comprising: receiving an annotation associated with the first physical object in the user's FOV via the first wearable device, and wherein communicating the first information to the second wearable device comprises communicating the annotation and an image of the first physical object to the second wearable device.

17. The method of claim 16, wherein the annotation comprises one or more virtual flags placed on a portion of a patient's body part, wherein the one or more virtual flags indicate an orientation of the portion of the patient's body part, an orientation of a camera that captured the image, or contextual information associated with the image or the portion of the patient's body part.

18. The method of claim 15, wherein the sharing session is part of an interaction between the user and a patient, and the method further comprises:

documenting the interaction between the user and the patient using at least one of the outward-facing imaging system or the microphone;

identifying relevant medical information from the interaction; and updating a medical record of the patient with the relevant medical information.

19. The method of claim 15, further comprising:

verifying an access privilege of the second wearable device; and sharing at least a portion of the first information to which the access privilege of the second wearable device is sufficient.

20. The method of claim 19, wherein the access privilege is managed by a patient whose medical information is being shared between the first wearable device and the second wearable device.

* * * * *